US012760094B2

(12) United States Patent
Wisniewski

(10) Patent No.: US 12,760,094 B2
(45) Date of Patent: Oct. 13, 2026

(54) METHODS AND COMPOSITIONS FOR TREATING CEREBRAL AMYLOID ANGIOPATHY

(71) Applicant: NEW YORK UNIVERSITY, New York, NY (US)

(72) Inventor: Thomas Wisniewski, Staten Island, NY (US)

(73) Assignee: NEW YORK UNIVERSITY, New York, NY (US)

( * ) Notice: Subject to any disclaimer, the term of this patent is extended or adjusted under 35 U.S.C. 154(b) by 934 days.

(21) Appl. No.: 17/819,059

(22) Filed: Aug. 11, 2022

(65) Prior Publication Data

US 2023/0087558 A1 Mar. 23, 2023

Related U.S. Application Data

(60) Provisional application No. 63/255,038, filed on Oct. 13, 2021, provisional application No. 63/232,609, filed on Aug. 12, 2021.

(51) Int. Cl.

*A61P 25/00* (2006.01)
*A61P 25/28* (2006.01)
*C07K 16/28* (2006.01)
*A61K 39/00* (2006.01)

(52) U.S. Cl.

CPC .............. *C07K 16/28* (2013.01); *A61P 25/28* (2018.01); *A61K 2039/505* (2013.01); *C07K 2317/565* (2013.01)

(58) Field of Classification Search

CPC .............. C07K 16/28; C07K 2317/565; C07K 16/2848; C07K 2317/34; C07K 2317/622; C07K 2317/54; C07K 2317/55; C07K 14/745; C07K 19/00; C07K 2317/21; C07K 2317/70; C07K 2317/73; C07K 2319/01; C07K 2319/33; C07K 2319/70; C07K 7/06; C07K 7/08; C07K 14/005; C07K 2317/24; A61P 25/28; A61P 35/00; A61P 7/02; A61P 9/00; A61P 31/04; A61P 31/10; A61P 31/12; A61P 37/04; A61K 2039/505

See application file for complete search history.

(56) References Cited

U.S. PATENT DOCUMENTS 8,753,631 B2 * 6/2014 Karpatkin .............. C07K 19/00 514/13.8

OTHER PUBLICATIONS

Donner et al, Sci Signal 9:ra52, 1-16, 2016.*
Hoecke et al, J Trans Med 17:54, 1-14, 2019.*
Paul, Fundamental Immunology, 3rd Edition, 1993, pp. 292-295.*
Colman P. M., Research in Immunology, 145:33-36, 1994.*
Maccallum et al, J. Mol. Biol., 262, 732-745, 1996.*
Pascalis et al, Journal of Immunology, 2002, vol. 169, pp. 3076-3084.*
Casset et al, Biochemical and Biophysical Research Communications, 2003, vol. 307, pp. 198-205.*
Holm et al, Molecular Immunology, 2007, vol. 44, pp. 1075-1084.*
Cummings et al., "Alzheimer's Disease Drug Development Pipeline: 2020," Alzheimer's Dementia 6:e12050 (2020).
Lacorte et al., "Safety and Efficacy of Monoclonal Antibodies for Alzheimer's Disease: A Systematic Review and Meta-Analysis of Published and Unpublished Clinical Trials," Journal of Alzheimer's Disease 87:101-129 (2022).

* cited by examiner

*Primary Examiner* — Mark Halvorson

(74) *Attorney, Agent, or Firm* — Troutman Pepper Locke LLP (Rochester)

(57) ABSTRACT

The present application discloses a method of inhibiting the onset of cerebral amyloid angiopathy (CAA) and associated conditions in a subject including administering, to a subject at risk of developing CAA, an antibody-based molecule that binds to GPIIIa49-66 on activated platelets, under conditions effective to inhibit formation of platelet micro-clots, thereby inhibiting the onset of CAA and associated conditions. Also described is a method of reducing cerebral vascular platelet micro-clots in a subject in need thereof and a combination therapeutic that includes an antibody-based molecule that binds to GPIIIa49-66 on activated platelets, and an Alzheimer's disease therapeutic.

13 Claims, 32 Drawing Sheets

Specification includes a Sequence Listing.

```
                                   SEQUENCE LISTING


Sequence total quantity: 23
SEQ ID NO: 1          moltype = AA  length = 5
FEATURE               Location/Qualifiers
source                1..5
                      mol_type = protein
                      organism = synthetic construct
SEQUENCE: 1
SYAMS                                                5

SEQ ID NO: 2          moltype = AA  length = 17
FEATURE               Location/Qualifiers
source                1..17
                      mol_type = protein
                      organism = synthetic construct
SEQUENCE: 2
SITSTGMETR YADSVKG                                   17

SEQ ID NO: 3          moltype = AA  length = 7
FEATURE               Location/Qualifiers
source                1..7
                      mol_type = protein
                      organism = synthetic construct
SEQUENCE: 3
GKSHFDY                                              7

SEQ ID NO: 4          moltype = AA  length = 118
FEATURE               Location/Qualifiers
source                1..118
                      mol_type = protein
                      organism = synthetic construct
SEQUENCE: 4
MAEVQLLESG GGLVQPGGSL RLSCAASGFT FSSYAMSWVR QAPGKGLEWV SSITSTGMET  60
RYADSVKGRF TISRDNSKNT LYLQMNSIRA EDTAVYYCAK GKSHFDYWGQ GTLVTVSS    118

SEQ ID NO: 5          moltype = AA  length = 11
FEATURE               Location/Qualifiers
source                1..11
                      mol_type = protein
                      organism = synthetic construct
SEQUENCE: 5
RASQSISSYL N                                         11

SEQ ID NO: 6          moltype = AA  length = 7
FEATURE               Location/Qualifiers
source                1..7
                      mol_type = protein
                      organism = synthetic construct
SEQUENCE: 6
TASFLQS                                              7

SEQ ID NO: 7          moltype = AA  length = 9
FEATURE               Location/Qualifiers
source                1..9
                      mol_type = protein
```

```
                        organism = synthetic construct
SEQUENCE: 7
QQRKSYPRT                                                  9

SEQ ID NO: 8            moltype = AA  length = 109
FEATURE                 Location/Qualifiers
source                  1..109
                        mol_type = protein
                        organism = synthetic construct
SEQUENCE: 8
TDIQMTQSPS SISASVGDRV TITCRASQSI SSYLNWYQQK PGKAPKLLIY TASFLQSGVP  60
SRFSGSGSGT DFTLTISSLQ PEDFATYYCQ QRKSYPRTFG QGTKVEIKR              109

SEQ ID NO: 9            moltype = DNA  length = 354
FEATURE                 Location/Qualifiers
source                  1..354
                        mol_type = other DNA
                        organism = synthetic construct
SEQUENCE: 9
atggccgagg tgcagctgtt ggagtctggg ggaggcttgg tacagcctgg ggggtccctg  60
agactctcct gtgcagcctc tggattcacc tttagcagct atgccatgag ctgggtccgc  120
caggctccag ggaagcctgg gctgtgggtc tcatctatta ctagtacggg tatggagaca  180
cgttacgcag actccgtgaa gggccggttc accatctcca gagacaattc caagaacacg  240
ctgtatctgc aaatgaacag cctgagagcc gaggacacgg ccgtatatta ctgtgcgaaa  300
ggtaagtcgc attttgacta ctggggccag ggaaccctgg tcaccgtctc gagc        354

SEQ ID NO: 10           moltype = DNA  length = 327
FEATURE                 Location/Qualifiers
source                  1..327
                        mol_type = other DNA
                        organism = synthetic construct
SEQUENCE: 10
acggacatcc agatgaccca gtctccatcc tccctgtctg catctgtagg agacagagtc  60
accatcactt gccgggcaag tcagagcatt agcagctatt taaattggta tcagcagaaa  120
ccagggaaag cccctaagct cctgatctat actgcatcct tttgcaaag tggggtccca  180
tcaaggttca gtggcagtgg atctgggaca gatttcactc tcaccatcag cagtctgcaa  240
cctgaagatt ttgcaactta ctactgtcaa cagcggaagt cgtatcctag gacgttcggc  300
caagggacca aggtggaaat caaacgg                                      327

SEQ ID NO: 11           moltype = AA  length = 18
FEATURE                 Location/Qualifiers
source                  1..18
                        mol_type = protein
                        organism = synthetic construct
SEQUENCE: 11
CAPESIEFPV SEARVLED                                        18

SEQ ID NO: 12           moltype = DNA  length = 21
FEATURE                 Location/Qualifiers
source                  1..21
                        mol_type = other DNA
                        organism = synthetic construct
SEQUENCE: 12
tcgttttgtc gttttgtcgt t                                    21

SEQ ID NO: 13           moltype = DNA  length = 22
FEATURE                 Location/Qualifiers
source                  1..22
                        mol_type = other DNA
                        organism = synthetic construct
SEQUENCE: 13
tgactgtgaa cgttcgagat ga                                   22

SEQ ID NO: 14           moltype = DNA  length = 20
FEATURE                 Location/Qualifiers
source                  1..20
                        mol_type = other DNA
                        organism = synthetic construct
SEQUENCE: 14
tccatgacgt tcctgacgtt                                      20

SEQ ID NO: 15           moltype = DNA  length = 20
FEATURE                 Location/Qualifiers
source                  1..20
                        mol_type = other DNA
                        organism = synthetic construct
SEQUENCE: 15
cgcgcgcgcg cgcgcgcgcg                                      20
```

-continued

```
SEQ ID NO: 16          moltype = DNA  length = 20
FEATURE                Location/Qualifiers
source                 1..20
                       mol_type = other DNA
                       organism = synthetic construct
SEQUENCE: 16
tccatgccgt tcctgccgtt                                              20

SEQ ID NO: 17          moltype = DNA  length = 17
FEATURE                Location/Qualifiers
source                 1..17
                       mol_type = other DNA
                       organism = synthetic construct
SEQUENCE: 17
gcggcgggcg cgcgccc                                                 17

SEQ ID NO: 18          moltype = DNA  length = 17
FEATURE                Location/Qualifiers
source                 1..17
                       mol_type = other DNA
                       organism = synthetic construct
SEQUENCE: 18
ctcccagcgt gcgccat                                                 17

SEQ ID NO: 19          moltype = DNA  length = 24
FEATURE                Location/Qualifiers
source                 1..24
                       mol_type = other DNA
                       organism = synthetic construct
SEQUENCE: 19
tcgtcgtttt gtcgttttgt cgtt                                         24

SEQ ID NO: 20          moltype = DNA  length = 20
FEATURE                Location/Qualifiers
source                 1..20
                       mol_type = other DNA
                       organism = synthetic construct
SEQUENCE: 20
tccatgacgt tcctgatgct                                              20

SEQ ID NO: 21          moltype = AA  length = 40
FEATURE                Location/Qualifiers
source                 1..40
                       mol_type = protein
                       organism = synthetic construct
SEQUENCE: 21
DAEFRHDSGY EVHHQKLVFF AEDVGSNKGA IIGLMVGGVV                        40

SEQ ID NO: 22          moltype = DNA  length = 20
FEATURE                Location/Qualifiers
source                 1..20
                       mol_type = other DNA
                       organism = synthetic construct
SEQUENCE: 22
ccaggtcccc agtccaaatc                                              20

SEQ ID NO: 23          moltype = DNA  length = 20
FEATURE                Location/Qualifiers
source                 1..20
                       mol_type = other DNA
                       organism = synthetic construct
SEQUENCE: 23
aatgccaggg agcctttgtt                                              20
```

METHODS AND COMPOSITIONS FOR TREATING CEREBRAL AMYLOID ANGIOPATHY

This application claims the benefit of U.S. Provisional Patent Application Ser. Nos. 63/232,609, filed Aug. 12, 2021, and 63/255,038, filed Oct. 13, 2021, which are hereby incorporated by reference in their entirety.

This invention was made with government support under grant numbers AG066512 and AG060882 awarded by National Institutes of Health (NIH). The government has certain rights in the invention.

FIELD

The present disclosure is directed to methods and compositions for treating cerebral amyloid angiopathy.

BACKGROUND

Alzheimer's disease (AD) is the most common cause of dementia among the elderly, affecting approximately 50 million people currently and with projections being ~150 million affected by 2050 ("2021 Alzheimer's Disease Facts and Figures," *Alzheimers Dement.* 17:327-406 (2021) and Scheltens et al., "Alzheimer's Disease," *Lancet* 397:1577-90 (2021)). Currently, there are no effective pharmacological means to treat or slow down this progression. AD is characterized by two dominant pathological hallmarks (Scheltens et al., "Alzheimer's Disease," *Lancet.* 397:1577-90 (2021); Reiss et al., "Alzheimer's Disease: Many Failed Trials, So Where Do We Go From Here?," *J. Investig. Med.* 68:1135-40 (2020)). One is the abnormal deposition of endogenous β-amyloid (Aβ) peptides ($A\beta_{1-40}$ and $A\beta_{1-42}$) in the brain parenchyma forming senile plaques and in the walls of cerebral vessels producing cerebral amyloid angiopathy (CAA) (Kirschner et al., "X-ray Diffraction From Intraneuronal Paired Helical Filaments and Extraneuronal Amyloid Fibers in Alzheimer Disease Indicates Cross-beta Conformation," *Proc. Natl. Acad. Sci. USA* 83:503-7 (1986); Selkoe, "Alzheimer's Disease: Genes, Proteins, and Therapy," *Physiol. Rev.* 81:741-66 (2001); LaFerla et al., "Intracellular Amyloid-beta in Alzheimer's Disease," *Nat. Rev. Neurosci.* 8:499-509 (2007); Busciglio et al., "Generation of Beta-amyloid in the Secretory Pathway in Neuronal and Nonneuronal Cells," *Proc. Natl. Acad. Sci. USA* 90:2092-6 (1993); Shepherd et al., "Expression of Amyloid Precursor Protein in Human Astrocytes In Vitro: Isoform-specific Increases Following Heat Shock," *Neuroscience* 99:317-25 (2000); and Simons et al., "Amyloidogenic Processing of the Human Amyloid Precursor Protein in Primary Cultures of Rat Hippocampal Neurons,". *J Neurosci.* 16:899-908 (1996)). The other is the intracellular accumulation of the microtubule associated protein tau in its hyperphosphorylated form resulting in the formations of neurofibrillary tangles (NFT) in neurons.

A substantial body of studies indicates that vascular damage and dysfunction, such as reduction of cerebral blood flow (CBF) and blood-brain barrier (BBB) disturbances, could be one of the earliest events contributing to the onset and progression of AD (Sochocka et al., "Vascular Oxidative Stress and Mitochondrial Failure in the Pathobiology of Alzheimer's Disease: A New Approach to Therapy," *CNS Neurol. Disord. Drug Targets* 12:870-81 (2013)). Vascular dysregulation has been linked with CAA. The presence of CAA and its severity is an independent factor for dementia (Smith E E., "Cerebral Amyloid Angiopathy as a Cause of Neurodegeneration," *J. Neurochem.* 144:651-8 (2018) and Jang et al., "Clinical Significance of Amyloid β Positivity in Patients With Probable Cerebral Amyloid Angiopathy Markers," *Eur. J. Nucl. Med. Mol. Imaging* 46:1287-98 (2019)). Almost 100% of AD patients have CAA, and in about a third of these patients it is rated as severe CAA (Smith E E., "Cerebral Amyloid Angiopathy as a Cause of Neurodegeneration," *J. Neurochem.* 144:651-8 (2018) and Weber et al., "Cerebral Amyloid Angiopathy: Diagnosis and Potential Therapies," *Expert Rev. Neurother.* 18:503-13 (2018)). The presence of CAA promotes the onset of AD symptoms (Boyle et al., "Cerebral Amyloid Angiopathy and Cognitive Outcomes in Community-Based Older Persons," *Neurology* 85:1930-6 (2015)) and is associated with faster cognitive decline in non-cognitively impaired (NCI) individuals (Boyle et al., "Cerebral Amyloid Angiopathy and Cognitive Outcomes in Community-Based Older Persons," *Neurology* 85:1930-6 (2015) and Bos et al., "Cerebrovascular and Amyloid Pathology in Predementia Stages: The Relationship With Neurodegeneration and Cognitive Decline," *Alzheimers Res. Ther.* 9:101 (2017)). The presence of CAA is also associated with tau pathology (Smith, "Cerebral Amyloid Angiopathy as a Cause of Neurodegeneration," *J. Neurochem.* 144:651-8 (2018); Malek-Ahmadi et al., "Cerebral Amyloid Angiopathy, and Cognitive Decline in Early Alzheimer's Disease," *J. Alzheimer's Dis.* 74:189-97 (2020); Sweeney et al., "Vascular Dysfunction—The Disregarded Partner of Alzheimer's Disease," *Alzheimers Dement.* 15:158-67 (2019); Merlini et al., "Tau Pathology-dependent Remodelling of Cerebral Arteries Precedes Alzheimer's Disease-related Microvascular Cerebral Amyloid Angiopathy," *Acta Neuropathol.* 131:737-52 (2016); Williams et al., "Relationship of Neurofibrillary Pathology to Cerebral Amyloid Angiopathy in Alzheimer's Disease," *Neuropathol. Appl. Neurobiol.* 31:414-21 (2005)). Hyperphosphorylated tau deposits have been report to be significant more likely to be found in areas of the brain affected by CAA (Williams et al., "Relationship of Neurofibrillary Pathology to Cerebral Amyloid Angiopathy in Alzheimer's Disease," *Neuropathol. Appl. Neurobiol.* 31:414-21 (2005)). A recent study showed that AD individuals with CAA were more likely to develop severe NFT pathology relative to those without CAA (Malek-Ahmadi et al., "Cerebral Amyloid Angiopathy, and Cognitive Decline in Early Alzheimer's Disease," *J. Alzheimer's Dis.* 74:189-97 (2020)). These findings indicate that the presence of CAA is an important factor influencing the severity of tau-related pathology. Therefore, identifying vascular risk factors that facilitate CAA lesions is potentially useful for the early diagnosis and treatment of AD patients.

Epidemiological studies link atherosclerosis with an increased risk for dementia and AD (Hofman et al., "Atherosclerosis, Apolipoprotein E, and Prevalence of Dementia and Alzheimer's Disease in the Rotterdam Study," *Lancet* 349:151-4 (1997); Roher et al., "Circle of Willis Atherosclerosis is a Risk Factor for Sporadic Alzheimer's Disease," *Arterioscler. Thromb. Vasc. Biol.* 23:2055-62 (2003)). However, whether these processes in the vasculature initiate the pathologic process of Aβ aggregation and accelerate tau pathology is still uncertain. Atherosclerosis is a chronic progressive vascular disease and is often accompanied by sustained platelet activation, increased platelet numbers, and the formation of platelet thrombi (Wang et al., "Cholesterol in Platelet Biogenesis and Activation," *Blood* 127:1949-53 (2016)). Platelets play an important role in CAA pathogenesis, in addition to their fundamental role in arterial thrombosis and hemostasis. Platelets contain high concentrations of amyloid precursor protein (APP) in their alpha granules (~1.1±0.3 μg/$10^8$ platelets), and express all of the enzymes which are required to process APP into Aβ peptides. In human blood, ~90% Aβ peptides are from platelets (Chen et al., "Platelets Are the Primary Source of Amyloid Beta-peptide in Human Blood," *Biochem. Biophys. Res. Commun.* 213:96-103 (1995); Bush et al., "The Amyloid Precursor Protein of Alzheimer's Disease is Released by Human Platelets," *J. Biol. Chem.* 265:15977-83 (1990); Van Nostrand et al., "Protease Nexin-II (Amyloid Beta-protein Precursor): A Platelet Alpha-granule Protein," *Science* 248: 745-8 (1990); Rosenberg et al., "Altered Amyloid Protein Processing in Platelets of Patients With Alzheimer Disease," *Arch. Neurol.* 54:139-44 (1997); Baskin et al., "Platelet APP Isoform Ratios Correlate With Declining Cognition in AD," *Neurology* 54:1907-9 (2000)). Platelets from AD patients showed abnormalities of platelet morphology and APP metabolism (Padovani et al., "Amyloid Precursor Protein in Platelets: A Peripheral Marker for the Diagnosis of Sporadic AD," *Neurology* 57:2243-8 (2001)). Moreover, platelet-derived AP can pass through the human cerebrovascular endothelial cell layers isolated from the brains of patients with AD (Davies et al., "Beta Amyloid Fragments Derived From Activated Platelets Deposit in Cerebrovascular Endothelium: Usage of a Novel Blood Brain Barrier Endothelial Cell Model System," *Amyloid* 7:153-65 (2000)), and these secreted Aβ peptides are similar to those found in amyloid plaques of AD patients (Scheuner et al., "Secreted Amyloid Beta-protein Similar to That in the Senile Plaques of Alzheimer's Disease is Increased In Vivo by the Presenilin 1 and 2 and APP Mutations Linked to Familial Alzheimer's Disease," *Nat Med.* 2:864-70 (1996)).

Platelet adhesion under conditions of high shear stress, as occurs in stenotic atherosclerotic arteries, is pivotal to the development of arterial thrombosis. Evidence shows that platelets are 300-500 times more concentrated in blood clots than in non-clotted blood (Kucheryavykh et al., "Platelets Are Responsible for the Accumulation of β-amyloid in Blood Clots Inside and Around Blood Vessels in Mouse Brain After Thrombosis," *Brain Res. Bull.* 128:98-105 (2017)). The formation of platelet-associated amyloid aggregates in cerebral vessels may compromise cerebral blood flow and hence neuron survival and function, leading to cognitive decline. In addition, platelets from this AD model have been documented to be normal in number and glycoprotein expression, but are more adherent to matrices such as fibrillar collagen, von Willebrand factor (vWF), fibrinogen, and fibrillary amyloid peptides compared to platelets from age-matching wild-type (WT) mice (Canobbio et al., "Increased Platelet Adhesion and Thrombus Formation in a Mouse Model of Alzheimer's Disease," *Cell Signal. England* 28:1863-71 (2016)).

It would be desirable, therefore, to identify additional therapeutic agents that can be used to diminish the release of platelet-associated amyloid aggregates and the formation of amyloid plaques.

The present disclosure is directed to overcoming these and other deficiencies in the art.

SUMMARY

A first aspect of the present disclosure is directed to a method of inhibiting the onset of cerebral amyloid angiopathy (CAA) and associated conditions in a subject. This method includes administering, to a subject at risk of developing CAA, an antibody-based molecule that binds to GPIIIa49-66 on activated platelets, under conditions effective to inhibit formation of platelet micro-clots, thereby inhibiting the onset of CAA and associated conditions.

A second aspect of the present disclosure is directed to a method of reducing cerebral vascular platelet micro-clots in a subject in need thereof. This method includes administering, to the subject having cerebral vascular platelet micro-clots, an antibody-based molecule that binds to GPIIIa49-66 on activated platelets, under conditions effective to dissolve and clear the cerebral vascular platelet micro-clots.

A third aspect of the present disclosure is directed to a combination therapeutic that includes an antibody-based molecule that binds to GPIIIa49-66 on activated platelets, and an Alzheimer's disease therapeutic.

The accompanying Examples demonstrate that atherosclerosis contributes to AD is via its effects on blood coagulation and chronic formation of platelet micro-clots, which sequester and enrich numerous activated platelets, thus allowing a massive release of Aβ peptides (directly, or cleaved from released APP) and the conversion of soluble Aβ40 into fibrillar Aβ aggregates at the surface of platelet micro-clots. This demonstration was tested in a well characterized triple transgenic (3×Tg) mouse model of Alzheimer's disease, which is one of the few models with both Aβ and tau-related deposits (Oddo et al., "Triple-transgenic Model of Alzheimer's Disease With Plaques and Tangles: Intracellular Abeta and Synaptic Dysfunction," *Neuron* 39:409-21 (2003); Drummond et al., "Alzheimer's Disease: Experimental Models end Reality," *Acta. Neuropathol.* 133: 155-75 (2017), each of which is hereby incorporated by reference in its entirety). The triple transgenic (3×Tg) AD mice were subjected to a high-fat diet (HFD) at 3 months of age, which corresponds to early adulthood in humans. After 9 months treatment, HFD-treated 3×Tg mice exhibited worse memory deficits accompanied by blood hypercoagulation, thrombocytosis, and chronic platelet activation. Procoagulant platelets from HFD-treated 3×Tg mice actively induced the conversion of soluble Aβ40 into fibrillar Aβ aggregates, associated with increased expression of integrin $\alpha IIb\beta_3$ and clusterin. At 9 months and older, platelet-associated fibrillar Aβ aggregates were observed to obstruct cerebral blood vessels in HFD-treated 3×Tg mice. HFD-treated 3×Tg mice exhibited a greater cerebral amyloid angiopathy (CAA) burden and a disrupted blood-brain barrier, as well as more extensive neuroinflammation, tau hyperphosphorylation and neuron loss. Disaggregation of preexisting platelet micro-clots with humanized GPIIIa49-66 scFv Ab (A11) significantly reduced platelet-associated fibrillar Aβ aggregates in vitro, and improved both vascular permeability and locomotor ability of mouse in vivo. In this model, Aβ aggregation is found not only in brain parenchyma but also in cerebral vessel walls (Drummond et al., "Alzheimer's Disease: Experimental Models end Reality," *Acta. Neuropathol.* 133:155-75 (2017); Grammas et al., "A New Paradigm for the Treatment of Alzheimer's Disease: Targeting Vascular Activation," *J. Alzheimers. Dis.* 40:619-30 (2014), each of which is hereby incorporated by reference in its entirety). The findings described herein confirm that a major contribution of atherosclerosis to AD pathology is via its effects on blood coagulation and the formation of platelet-mediated Aβ aggregates that compromise cerebral blood flow and therefore neuronal function, which leads to cognitive decline.

BRIEF DESCRIPTION OF THE DRAWINGS

FIG. 1A depicts treatment protocols to induce atherosclerosis in 3×Tg mice: N, normal chow; H, High-fat diet. FIG. 1B shows serum total cholesterol (TC) in 12-month-old 3×Tg mice after different treatment (n=14/group). FIG. 1C shows representative images of en face oil red O staining of artery plaque area in thoracic-abdominal aorta (TA) of 12-month-old 3×Tg mice after different treatment. FIG. 1D depicts quantification of the plaque area of TA by ImageJ version 1.50i (n=5/group). FIG. 1E shows body weight after different treatment (n=14/group). FIG. 1F shows a diagram of methods for hippocampus-dependent contextual fear conditioning. After training, mice were allowed to explore 3 minutes in shock chamber (Contextual test). FIG. 1G shows freezing responses of both HFD-treated 3×Tg mice (n=9) and normal chow-treated mice (n=12) during cued fear conditioning. Each dot or square represents one individual. Data are expressed as mean±SD, unpaired Student t-test, two-tailed. ***p<0.001, n.s., not significant.

FIGS. 2A-2C show mouse tail bleeding times (FIG. 2A), peripheral blood platelet counts (FIG. 2B), and mean platelet volume (MPV) (FIG. 2C) in 12-month-old HFD-treated 3×Tg mice, normal chow-treated mice, and B6129S wild-type (WT) mice (n=14/group). FIG. 2D shows serum IL-6 levels in 12-month-old 3×Tg mice after different treatment (n=11-12/group). FIG. 2E shows qRT-PCR analysis of thrombopoietin (Tpo) mRNA from livers of 12-month-old 3×Tg mice after different treatment (n=5/group). The relative quantity of Tpo mRNA was normalized to that of the housekeeping gene Gapdh using the ΔΔCt method. FIG. 2F shows serum TPO levels in 12-month-old 3×Tg mice after different treatment (n=12/group). FIG. 2G depicts representative images of bone marrow smear in 12-month-old 3×Tg mice after different treatment. 1, red blood cell (RBC); 2, lymphocyte (LBC); 3, megakaryocytes (Meg). FIG. 2H shows a summary of the mechanism of HFD treatment-induced thrombocytosis in 3×Tg mice. Each dot or square represents one individual. Data are expressed as mean±SD, unpaired Student t-test, two-tailed. *p<0.05, p<0.01, *p<0.001, n.s., not significant.

FIGS. 3A-3C depict the expression of platelet integrin $\alpha_{IIb}\beta_3$ determined by flow cytometry (FIG. 3A) and Western blot (FIGS. 3B, 3C) in B6129S wild-type (WT) (n=2), normal chow-treated (N) 3×Tg mice (n=2), and high-fat diet-treated (H) 3×Tg mice (n=3). FIGS. 3D-3E show increased clusterin (CLU) expression in platelets from HFD-treated 3×Tg mice. Levels of CLU in platelets from 12-month-old 3×Tg mice after different treatment were determined by Western blotting. The relative quantity of CLU proteins is normalized to that of GAPDH and expressed as mean±SD (n=4/group). FIG. 3F depicts representative images of Congo red staining-positive Aβ fibril formation in cultures of mouse platelets from different treatment incubated with soluble Aβ40 (50 μg/ml) for 48 h at 37° C. Scale bar, 50 μm. FIG. 3G shows quantification of the number of fibrillar Aβ aggregates (n=3/group). In FIG. 3H, analysis of Aβ fibrils adhere to platelet from HFD-treated 3×Tg mice by immunofluorescence staining. Platelets (staining with anti-GPIba); Aβ (staining with anti-Aβ1-16). Scale bar, 50 μm. Data are expressed as mean±SD, unpaired Student t-test, two-tailed. p<0.01, *p<0.001, n.s., not significant. These experiments were repeated independently at least three times.

FIGS. 4A-4B show quantification of parenchymal amyloid numbers (FIG. 4A), and CAA amyloid numbers (FIG. 4B) using Congo red stainings. FIG. 4C shows representative images of Congo red staining-positive micro-clots in different sized cerebrovascular vessels of HFD-treated 3×Tg mice at 9 months and older. Scale bar, 50 μm. FIG. 4D shows representative immunofluorescence images of the colocalization of platelet thrombi and vascular Aβ plaques in cerebral vessels of HFD-treated 3×Tg mice. Overlay of Aβ immunofluorescence and GPIbα is shown in merge. Scale bar, 20 μm. In FIGS. 4E-4G the levels of reactive oxygen species (ROS) (FIG. 4E), glutathione (GSH) (FIG. 4F), and endostatin (ET) (FIG. 4G) in mouse brains were determined by sandwich ELISA. Each dot or square represents one individual (n=11~13/group). Data are expressed as mean±SD, unpaired Student t-test, two-tailed. *p<0.001, **p<0.0001, n.s., not significant.

FIG. 5A shows representative TEM images of mouse brain vessels in 12-month-old B6129S wild-type (WT) mice, normal chow (N)-treated-3×Tg mice, and HFD-treated (H)-3×Tg mice. Box, cerebral vascular endothelium. Arrowhead, endothelial tight junction. Arrow, disrupted endothelial tight junction. Scale bar, 2 μm (upper panels) and 500 nm (lower panels). FIG. 5B shows representative images showing cerebral vascular permeability through simple visualization of brain sections under the excitation of 550 nm by fluorescence microscope. Scale bar, 20 μm. Evans blue is a diazo salts fluorescent dye with high affinity for albumin, and Evans blue bound albumin presents red fluorescence under the excitation of 550 nm. FIG. 5C shows quantification of Evans blue extravasated in brain tissues as described in the methods. Each symbol represents one individual (n=5/group). Data are expressed as mean±SD, unpaired Student t-test, two-tailed. ****p<0.0001, n.s., not significant.

FIG. 6A shows representative images of glial fibrillary acidic protein (GFAP) immunoreactivity in pyramidal layer and subiculum of mouse brain sections. FIGS. 6B-6C show quantification of GFAP intensity in pyramidal layer (FIG. 6B) and subiculum (FIG. 6C) of mouse brain sections (n=10~12/group). Each dot or square represents one individual. Data are expressed as mean±SD, unpaired Student t-test, two-tailed. **p<0.01.

FIG. 7A shows representative immunohistochemical images of tau hyperphosphorylation (p-S396) in different hippocampal subregions (CA1, CA3, and DG). Scale bar, 200 μm (overall pictures) and 50 μm (enlarged pictures in the lower right corner of the overall pictures), respectively. FIG. 7B shows western blotting results of Tau and p-Tau in brain tissues of different-treated 3×Tg mice. FIG. 7C shows that the relative quantity of p-Tau proteins is normalized to that of Tau and expressed as mean±SD (n=4), unpaired Student t-test, two-tailed. ***p<0.001.

FIG. 8A shows representative immunohistochemical images of neurons at different hippocampal subregions stained with anti-NeuN antibody. Scale bar, 50 μm. FIG. 8B shows quantification of the numbers of NeuN-positive neurons at different hippocampal subregions (n=3/group). Data are expressed as mean±SD, unpaired Student t-test, two-tailed. p<0.01; *p<0.001; n.s., not significant.

FIG. 9A shows analysis of brain infarction area in post-ischemic stroke model. Mouse brains were dissected and were stained with red triphenyltetrazolium chloride (TTC). Each symbol represents one individual (n=4/group). FIG. 9B shows quantification of brain infarction area by ImageJ version 1.50i (n=4/group). Each dot or square represents one individual. FIG. 9C shows western blotting results of p-Tau in brain tissues of different-treated 3×Tg mice underwent the challenge of acute ischemic stroke. FIG. 9D shows that the relative quantity of p-Tau proteins is normalized to that of Tau and expressed as mean±SD (n=4), unpaired Student t-test, two-tailed. p<0.01; *p<0.001.

FIG. 10A depicts a representative photomicrograph showing that A11 dose-dependently inhibited fibrillar Aβ aggregate formation in the cultures of platelets from HFD-treated 3×Tg mice in culture with Aβ40 compared to irrelevant control scFv Ab. Scale bar, 20 μm. FIG. 10B shows quantification of the numbers of fibrillar Aβ aggregates (n=4 culture wells/dose). FIG. 10C shows body weight of HFD-treated 3×Tg mice after A11 or control scFv Ab treatment (n=8-9/group). FIGS. 10D-10I show mouse behavior analysis by homecage testing (n=8~9/group). FIG. 10J shows freezing responses of both A11 and control scFv Ab treatment during cued fear conditioning. FIG. 10K shows quantification of Evans blue extravasated in brain tissues of different groups. Each dot or square represents one individual. Data are expressed as mean±SD, unpaired Student t-test, two-tailed. *p<0.05; **p<0.01; n.s., not significant.

DETAILED DESCRIPTION

Figure 1A:
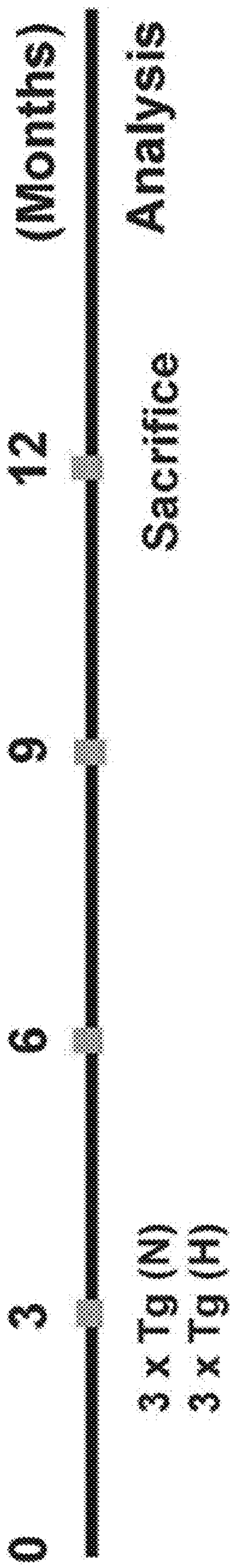
FIGS. 1A-1G show high-fat diet (HFD)-induced atherosclerosis facilitates memory deficits.

One aspect of the present disclosure is directed to a method of inhibiting the onset of cerebral amyloid angiopathy (CAA) and associated conditions in a subject. This method includes administering, to a subject at risk of developing CAA, an antibody-based molecule that binds to GPIIIa49-66 on activated platelets, under conditions effective to inhibit formation of platelet micro-clots, thereby inhibiting the onset of CAA and associated conditions.

Integrin αIIbβ3 (platelet glycoprotein GPIIb/IIIa) is a heterodimeric receptor of the integrin family expressed at high density (50,000-80,000 copies/cell) on the platelet membrane (Shattil et al., "Perspectives Series: Cell Adhesion in Vascular Biology. Integrin Signaling in Vascular Biology," *J. Clin. Invest.* 100 (1):1-5 (1997), which is hereby incorporated by reference in its entirety). In circulation it is normally in a resting state but is activated during platelet aggregation and adhesion, which in binding to fibrinogen and von Willebrand factor allows formation of a platelet aggregate or a mural thrombus on damaged vessel walls. GPIIIa(49-66) is a linear epitope of the integrin subunit β3 (GPIIIa), having the amino acid sequence of CAPESIEFPVSEARVLED (SEQ ID NO: 11) that is expressed on the surface of platelets (Morris et al., "Autoimmune Thrombocytopenic Purpura in Homosexual Men," *Ann. Intern. Med.* 96:714-717 (1982); Najean et al., "The Mechanism of Thrombocytopenia in Patients with HIV Infection," *J. Lab. Clin. Med.* 123(3):415-20 (1994), which are hereby incorporated by reference in their entirety).

The methods of the present disclosure involve administering, to a subject, an antibody-based molecule that binds to GPIIIa49-66 on activated platelets. In one embodiment, the antibody-based molecule is an antibody that is raised against GPIIIa49-66 or a binding fragment thereof. In another embodiment, the antibody-based molecule is an antibody that binds to at least a portion of GPIIIa49-66, where GPIIIa49-66 comprises the amino acid sequence of SEQ ID NO: 11 (CAPESIEFPVSEAREVLED).

Antibody-based molecules include, without limitation, full antibodies, epitope binding fragments of whole antibodies, and antibody derivatives. An epitope binding fragment of an antibody can be obtained through the actual fragmenting of a parental antibody (for example, a Fab or $(Fab)_2$ fragment). Alternatively, the epitope binding fragment is an amino acid sequence that comprises a portion of the amino acid sequence of such parental antibody. As used herein, a molecule is said to be a "derivative" of an antibody (or relevant portion thereof) if it is obtained through the actual chemical modification of a parent antibody or portion thereof, or if it comprises an amino acid sequence that is substantially similar to the amino acid sequence of such parental antibody or relevant portion thereof (for example, differing by less than 30%, less than 20%, less than 10%, or less than 5% from such parental molecule or such relevant portion thereof, or by 10 amino acid residues, or by fewer than 10, 9, 8, 7, 6, 5, 4, 3 or 2 amino acid residues from such parental molecule or relevant portion thereof).

As used herein, the term "antibody" is meant to include intact immunoglobulins derived from natural sources or from recombinant sources, as well as immunoreactive portions (i.e., binding portions) of intact immunoglobulins. The antibody that binds to GPIIIa49-66 on activated platelets as described in accordance with the methods herein may exist in a variety of forms including, for example, as a polyclonal antibody, monoclonal antibody, antibody fragments (e.g. Fv, Fab and $F(ab)_2$), as well as single chain antibody (scFv), chimeric antibody, and humanized antibody (Ed Harlow and David Lane, Using Antibodies: A Laboratory Manual (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA* 85:5879-5883 (1988); Bird et al., "Single-Chain Antigen-Binding Proteins," *Science* 242:423-426 (1988), which are hereby incorporated by reference in their entirety).

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain ($V_L$) and/or one constant domain ($C_L$). The heavy chain can also comprise one variable domain ($V_H$) and/or, depending on the class or isotype of antibody, three or four constant domains (CH1, CH2, CH3 and CH4). In humans, the isotypes are IgA, IgD, IgE, IgG and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hyper-variable or complementarity-determining regions (CDRs), are found in each of $V_L$ and $V_H$, which are supported by less variable regions called framework variable regions. Suitable antibodies for use in the methods described herein include IgG monoclonal antibodies as well as antibody fragments or engineered forms.

Also suitable for use in the methods described herein are fragments of antibodies (including Fab and $(Fab)_2$ fragments) that exhibit epitope-binding. Antibody fragments can be obtained, for example, by protease cleavage of intact antibodies. Single domain antibody fragments possess only one variable domain (e.g., $V_L$ or $V_H$). Examples of the epitope-binding fragments encompassed within the present invention include (i) Fab' or Fab fragments, which are monovalent fragments containing the $V_L$, $V_H$, $C_L$ and $C_H1$ domains; (ii) $F(ab')_2$ fragments, which are bivalent fragments comprising two Fab fragments linked by a disulfide bridge at the hinge region; (iii) Fd fragments consisting essentially of the $V_H$ and $C_H1$ domains; (iv) Fv fragments consisting essentially of a $V_L$ and $V_H$ domain, (v) dAb fragments (Ward et al., "Binding Activities Of A Repertoire Of Single Immunoglobulin Variable Domains Secreted From *Escherichia coli," Nature* 341:544-546 (1989) which is hereby incorporated by reference in its entirety), which consist essentially of a $V_H$ or $V_L$ domain and also called domain antibodies (Holt et al. "Domain Antibodies: Proteins For Therapy," *Trends Biotechnol.* 21(11):484-490 (2003), which is hereby incorporated by reference in its entirety); (vi) camelid or nanobodies (Revets et al. "Nanobodies As Novel Agents For Cancer Therapy," *Expert Opin. Biol. Ther.* 5(1):111-124 (2005), which is hereby incorporated by reference in its entirety), and (vii) isolated complementarity determining regions (CDR). An epitope-binding fragment may contain 1, 2, 3, 4, 5 or all 6 of the CDR domains of such antibody.

Such antibody fragments are obtained using conventional techniques known to those of skill in the art. For example, $F(ab')_2$ fragments may be generated by treating a full-length antibody with pepsin. The resulting $F(ab')_2$ fragment may be treated to reduce disulfide bridges to produce Fab' fragments. Fab fragments may be obtained by treating an IgG antibody with papain and Fab' fragments may be obtained with pepsin digestion of IgG antibody. A Fab' fragment may be obtained by treating an $F(ab')_2$ fragment with a reducing agent, such as dithiothreitol. Antibody fragments may also be generated by expression of nucleic acids encoding such fragments in recombinant cells (see e.g., Evans et al., "Rapid Expression Of An Anti-Human CS Chimeric Fab Utilizing A Vector That Replicates In COS And 293 Cells," *J. Immunol. Meth.* 184:123-38 (1995), which is hereby incorporated by reference in its entirety). For example, a chimeric gene encoding a portion of a $F(ab')_2$ fragment could include DNA sequences encoding the CH1 domain and hinge region of the heavy chain, followed by a translational stop codon to yield such a truncated antibody fragment molecule. Suitable fragments capable of binding to a desired epitope may be readily screened for utility in the same manner as an intact antibody.

Antibody derivatives suitable for use in the methods of the present disclosure include those molecules that contain at least one epitope-binding domain of an antibody, and are typically formed using recombinant techniques. One exemplary antibody derivative suitable for use in the methods of the present disclosure is a single chain Fv (scFv). A scFv is formed from the two domains of the Fv fragment, the $V_L$ region and the $V_H$ region, which are encoded by separate gene. Such gene sequences or their encoding cDNA are joined, using recombinant methods, by a flexible linker (typically of about 10, 12, 15 or more amino acid residues) that enables them to be made as a single protein chain in which the $V_L$ and $V_H$ regions associate to form monovalent epitope-binding molecules (see e.g., Bird et al., "Single-Chain Antigen-Binding Proteins," *Science* 242:423-426 (1988); and Huston et al., "Protein Engineering Of Antibody Binding Sites: Recovery Of Specific Activity In An Anti-Digoxin Single-Chain Fv Analogue Produced In *Escherichia coli," Proc. Natl. Acad. Sci.* (*U.S.A.*) 85:5879-5883 (1988), which are hereby incorporated by reference in their entirety). Alternatively, by employing a flexible linker that is not too short (e.g., less than about 9 residues) to enable the $V_L$ and $V_H$ regions of a different single polypeptide chains to associate together, one can form a bispecific antibody, having binding specificity for two different epitopes.

In another embodiment, a suitable antibody derivative for use in the methods of the present disclosure is a divalent or bivalent single-chain variable fragment, engineered by linking two scFvs together either in tandem (i.e., tandem scFv), or such that they dimerize to form diabodies (Holliger et al., "'Diabodies': Small Bivalent And Bispecific Antibody Fragments," *Proc. Natl. Acad. Sci.* (*U.S.A.*) 90(14):6444-8 (1993), which is hereby incorporated by reference in its entirety). In yet another embodiment, the antibody is a trivalent single chain variable fragment, engineered by linking three scFvs together, either in tandem or in a trimer formation to form triabodies. In another embodiment, the antibody is a tetrabody single chain variable fragment. In another embodiment, the antibody is a "linear antibody" which is an antibody comprising a pair of tandem Fd segments ($V_H$-$C_H1$-$V_H$-$C_H1$) that form a pair of antigen binding regions (see Zapata et al., *Protein Eng.* 8(10):1057-1062 (1995), which is hereby incorporated by reference in its entirety). In another embodiment, the antibody derivative is a minibody, consisting of the single-chain Fv regions coupled to the $C_H3$ region (i.e., scFv-$C_H3$).

An exemplary antibody-based molecule that binds to GPIIIa49-66 in accordance with the methods described herein comprises a heavy chain variable region that includes (i) a complementarity-determining region 1 (CDR-H1) comprising the amino acid sequence of SEQ ID NO: 1 (SYAMS) or a modified amino acid sequence of SEQ ID NO:1, where said modified sequence has at least 80% sequence identity to SEQ ID NO: 1, (ii) a complementarity-determining region 2 (CDR-H2) comprising the amino acid sequence of SEQ ID NO: 2 (SITSTGMETRYADSVKG) or a modified amino acid sequence of SEQ ID NO: 2, where said modified sequence has at least 80% sequence identity to SEQ ID NO: 2, and (iii) a complementarity-determining region 3 (CDR-H3) comprising the amino acid sequence of SEQ ID NO: 3 (GKSHFDY) or a modified amino acid sequence of SEQ ID NO: 3, where said modified sequence has at least 80% sequence identity to SEQ ID NO: 3.

In any embodiment, the antibody-based molecule that binds to GPIIIa49-66 further comprises a light chain variable region that includes (i) a complementarity-determining region 1 (CDR-L1) comprising the amino acid sequence of SEQ ID NO: 5 (RASQSISSYLN) or a modified amino acid sequence of SEQ ID NO: 5, where said modified sequence has at least 80% sequence identity to SEQ ID NO: 5, (ii) a complementarity-determining region 2 (CDR-L2) comprising the amino acid sequence of SEQ ID NO: 6 (TASFLQS) or a modified amino acid sequence of SEQ ID NO: 6, where said modified sequence has at least 80% sequence identity to SEQ ID NO: 6, and (iii) a complementarity-determining region 3 (CDR-L3) comprising the amino acid sequence of SEQ ID NO: 7 (QQRKSYPRT), or a modified amino acid sequence of SEQ ID NO: 7, where said modified sequence has at least 80% sequence identity to SEQ ID NO: 7.

In any embodiment, the antibody-based molecule comprises a heavy chain variable region ($V_H$) comprising an amino acid sequence having at least 80% sequence identity to the amino acid sequence of SEQ ID NO: 4 as shown below:

(SEQ ID NO: 4)
MAEVQLLESGGGLVQPGGSLRLSCAASGFTFSSYAMSWVRQAPGKGLE

WVSSITSTGMETRYADSVKGRFTISRDNSKNTLYLQMNSIRAEDTAVY

YCAKGKSHFDYWGQGTLVTVSS

As shown in the bold typeface portions of SEQ ID NO: 4 above, CDR1 includes SYAMS (SEQ ID NO: 1), CDR2 includes SITSTGMETRYADSVKG (SEQ ID NO: 2), and CDR3 includes GKSHFDY (SEQ ID NO: 3).

In any embodiment, the antibody-based molecule comprises a light chain variable region ($V_L$) comprising an amino acid sequence having at least 80% sequence identity to the amino acid sequence of SEQ ID NO: 8 as shown below:

(SEQ ID NO: 8)
TDIQMTQSPSSISASVGDRVTITCRASQSISSYLNWYQQKPGKAPKLL

IYTASFLQSGVPSRFSGSGSGTDFTLTISSLQPEDFATYYCQQRKSYP

RTFGQGTKVEIKR

As shown in the underlined portions of SEQ ID NO: 8 above, CDR1 includes RASQSISSYLN (SEQ ID NO: 5), CDR2 includes TASFLQS (SEQ ID NO: 6), and CDR3 includes QQRKSYPRT (SEQ ID NO: 7).

Suitable amino acid modifications to the heavy chain CDR sequences and/or the light chain CDR sequences of the GPIIIa49-66 antibody-based molecule disclosed herein include, for example, conservative substitutions or functionally equivalent amino acid residue substitutions that result in variant CDR sequences having similar or enhanced binding characteristics to those of the CDR sequences disclosed herein as described above. Encompassed by the present disclosure are CDRs of SEQ ID NOs: 1-3 and 5-7 containing 1, 2, 3, 4, 5, or more amino acid substitutions (depending on the length of the CDR) that maintain or enhance GPIIIa49-66 binding of the antibody. The resulting modified CDRs are at least 70%, at least 75%, at least 80%, at least 85%, at least 90%, or at least 95% similar in sequence to the CDRs of SEQ ID NOs: 1-3 and 5-7, respectively.

Suitable amino acid modifications to the heavy chain CDR or the light chain CDR sequences provided herein include, for example, conservative substitutions or functionally equivalent amino acid residue substitutions that result in variant CDR sequences having similar or enhanced binding characteristics to those of the CDR sequences of SEQ ID NOs: 1-3 and 5-7. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981, which is hereby incorporated by reference in its entirety). Non-conservative substitutions can also be made to the heavy chain CDR sequences of SEQ ID NOs: 1-3 and 5-7. Non-conservative substitutions involve substituting one or more amino acid residues of the CDR with one or more amino acid residues from a different class of amino acids to improve or enhance the binding properties of CDR. The amino acid sequences of the heavy chain variable region CDRs and/or the light chain variable region CDRs disclosed herein may further comprise one or more internal neutral amino acid insertions or deletions that maintain or enhance GPIIIa49-66 binding.

In any embodiment, the antibody-based molecule administered to a subject at risk of developing CAA in accordance as described herein is a single chain antibody. A preferred single-chain antibody comprises a variable heavy chain comprising an amino acid sequence having at least 80%, at least 85%, at least 90%, or at least 95% sequence similarity to the amino acid sequence of SEQ ID NO: 4 and a variable light chain comprising an amino acid sequence having at least 80%, at least 85%, at least 90%, or at least 95% sequence similarity to the amino acid sequence of SEQ ID NO: 8. In one embodiment, the single-chain antibody of the present disclosure comprises a heavy chain having an amino acid sequence of SEQ ID NO: 4 and a light chain having an amino acid sequence of SEQ ID NO: 8.

In any embodiment, a nucleic acid molecule encoding the antibody-based molecule is administered to a subject in accordance with the methods described herein. As used herein, the term "nucleic acid molecule" refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Suitable nucleic acid molecules also include DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA. Thus, "nucleic acid molecule" embraces chemically, enzymatically or metabolically modified forms of polynucleotides as typically found in nature, as well as the chemical forms of DNA and RNA characteristic of viruses and cells.

In one embodiment, the nucleic acid molecule encoding the GPIIIa49-66 antibody as disclosed herein comprises a nucleotide sequence encoding any one, any two, any three, any four, any five, or any six of the CDRs described supra having amino acid sequences of SEQ ID NOs: 1-3 and 5-7. In any embodiment, the nucleic acid molecule encoding the GPIIIa49-66 antibody as disclosed herein comprises a nucleotide sequence encoding the heavy chain variable region of SEQ ID NO: 4, and the light chain variable region of SEQ ID NO: 8.

In any embodiment, the nucleic acid molecule is an mRNA molecule encoding the heavy chain CDRs of SEQ ID NOs: 1-3 and the light chain CDRs of SEQ ID NOs: 5-7. In any embodiment, the mRNA molecule encoding the GPIIIa49-66 antibody as disclosed herein comprises a nucleotide sequence encoding the heavy chain variable region of SEQ ID NO: 4, and the light chain variable region of SEQ ID NO: 8.

In any embodiment, the nucleic acid molecule is an DNA molecule encoding the heavy chain CDRs of SEQ ID NOs: 1-3 and the light chain CDRs of SEQ ID NOs: 5-7. In any embodiment, the DNA molecule encoding the GPIIIa49-66 antibody as disclosed herein comprises a nucleotide sequence encoding the heavy chain variable region of SEQ ID NO: 4, and the light chain variable region of SEQ ID NO: 8. An exemplary DNA molecule encoding the GPIIIa49-66 antibody as disclosed herein comprises a nucleotide sequence of SEQ ID NO: 9 encoding the variable heavy chain, and a nucleotide sequence of SEQ ID NO: 10 encoding the variable light chain.

There are two types of sporadic CAA, depending on the location of amyloid accumulation (see Thal et al., "Two Types of Sporadic Cerebral Amyloid Angiopathy", *J. Neuropathol. Exp. Neurol.* 61(3):282-93 (2002), which is hereby incorporated by reference in its entirety). CAA-Type 1 is classified as detectable amyloid beta-proteins in cortical capillaries, leptomeningeal and cortical arteries, arterioles, veins, and venules. CAA-Type 2 is classified as detectable amyloid beta-proteins in leptomeningeal and cortical vessels with the exception of cortical capillaries. In one embodiment, the subject treated in accordance with the methods disclosed herein has sporadic CAA.

In another embodiment, a subject at risk for CAA suitable for treatment in accordance with the methods disclosed herein is a subject having atherosclerosis. As disclosed herein the inventors have found that atherosclerosis contributes to AD pathology via its effects on blood coagulation and

```
VH DNA (SEQ ID NO: 9):
atggccgagg tgcagctgtt ggagtctggg ggaggcttgg tacagcctgg ggggtccctg     60

agactctcct gtgcagcctc tggattcacc tttagcagct atgccatgag ctgggtccgc    120

caggctccag ggaagcctgg gctgtgggtc tcatctatta ctagtacggg tatggagaca    180

cgttacgcag actccgtgaa gggccggttc accatctcca gagacaattc caagaacacg    240

ctgtatctgc aaatgaacag cctgagagcc gaggacacgg ccgtatatta ctgtgcgaaa    300

ggtaagtcgc attttgacta ctggggccag ggaaccctgg tcaccgtctc gagc          354

VL DNA (SEQ ID NO: 10):
acggacatcc agatgaccca gtctccatcc tccctgtctg catctgtagg agacagagtc     60

accatcactt gccgggcaag tcagagcatt agcagctatt taaattggta tcagcagaaa    120

ccagggaaag cccctaagct cctgatctat actgcatcct tttgcaaag tggggtccca     180

tcaaggttca gtggcagtgg atctgggaca gatttcactc tcaccatcag cagtctgcaa    240

cctgaagatt ttgcaactta ctactgtcaa cagcggaagt cgtatcctag gacgttcggc    300

caagggacca aggtggaaat caaacgg                                        327
```

As described herein the methods of the present disclosure are suitable for inhibiting the onset of cerebral amyloid angiopathy (CAA) and associated conditions. CAA is a cerebrovascular disorder in which amyloid beta-peptides accumulate within the leptomeninges and small to medium-sized cerebral blood vessels, and such accumulation subsequently increases the risk for strokes through bleeding and dementia. There are two forms of CAA: hereditary and non-hereditary, also known as sporadic CAA. Hereditary CAA is caused by one or more genetic mutations. There are various types of hereditary CAA that are named after the regions where they were first diagnosed, also known as familial variants: Dutch type, Finnish type, Flemish type, Italian type, Icelandic type, Arctic type, British type, or Piedmont type. Different types are distinguished by their genetic mutations and subsequent signs and symptoms. In one embodiment, the subject treated in accordance with the methods disclosed herein has hereditary CAA. In any embodiment, the subject has one or more mutations in a gene selected from APP, CST3, PRNP, GSN, TTR, or ITM2B (see Kuhn et al. "Cerebral Amyloid Angiopathy", *StatPearls*, StatPearls Publishing (2021), and Revesz et al., "Genetics and Molecular Pathogenesis of Sporadic and Hereditary Cerebral Amyloid Angiopathies," *Acta Neuropathol.* 111(1): 115-130 (2009), which are hereby incorporated by reference in their entirety).

the formation of platelet-mediated Aβ aggregates that compromise cerebral blood flow and therefore neuronal function. Thus, when treated in accordance with the method described herein, the onset of cerebral amyloid angiopathy (CAA) and associated conditions can be prevented in a subject having atherosclerosis.

In another embodiment, the subject has a condition associated with CAA. For example, a subject suitable for treatment in accordance with the methods described herein may have a condition associated with CAA including, but not limited to, cerebral hemorrhage, cerebral infarction, cognitive impairment, dementia, and Alzheimer's disease.

In accordance with this and all aspects of the present disclosure, the "subject" is typically a human, but can also include non-human mammals. Non-human mammals amenable to treatment in accordance with the methods described herein include, without limitation, primates, cows, dogs, cats, rodents (e.g., mouse, rat, guinea pig), horses, deer, cervids, cattle and cows, sheep, and pigs.

In prophylactic applications, the antibody-based molecule that binds to GPIIIa49-66 is administered to a subject that is susceptible to, or otherwise at risk of, developing CAA, in an amount sufficient to eliminate or reduce the risk of the CAA or to delay, inhibit, or prevent the onset of the CAA. Prophylactic application also includes the administration of an antibody composition to prevent or delay the recurrence or relapse of a condition. The present methods and compositions are especially suitable for prophylactic treatment of individuals who have a known hereditary risk for CAA or have an associated condition, such as atherosclerosis, cerebral hemorrhage, cerebral infarction, cognitive impairment, dementia, and Alzheimer's disease.

Another aspect of the present disclosure is directed to a method of reducing cerebral vascular platelet micro-clots in a subject. This method includes administering, to the subject having cerebral vascular platelet micro-clots, an antibody-based molecule that binds to GPIIIa49-66 on activated platelets, under conditions effective to dissolve and clear the cerebral vascular platelet micro-clots.

In accordance with this aspect of the present disclosure, a subject having cerebral vascular platelet micro-clots that is suitable for treatment with an antibody-based molecule that binds GPIIIa49-66 is a subject that has cerebral amyloid angiopathy (CAA). In this aspect, where treatment is carried out on a subject that has CAA, it is contemplated that the progression of CAA can be delayed such that disease progression advances more slowly than in the absence of treatment or, in some instances, reversed.

In one embodiment, the subject having CAA has a hereditary form of CAA. As described supra, the hereditary form of CAA may be caused by one or more genetic mutations, for example, in a gene selected from APP, CST3, PRNP, GSN, TTR, or ITM2B.

Other subjects having cerebral vascular platelet micro-clots that are suitable for treatment in accordance with this method of the present disclosure include, without limitation subjects having Alzheimer's disease, subjects at risk for or having suffered cerebral hemorrhage, and subjects at risk for or having suffered cerebral infarction.

Suitable antibody-based molecules that bind to GPIIIa49-66 and nucleic acid molecules encoding the same that are suitable for use in the described method of reducing cerebral vascular platelet micro-clots are described supra.

As described supra, suitable subjects include humans and non-human mammals. In therapeutic applications, pharmaceutical compositions are administered to a subject suspected of, or already suffering from cerebral vascular platelet micro-clots in an amount sufficient to dissolve and clear the cerebral vascular platelet micro-clots. An amount adequate to accomplish this is defined as a therapeutically- or pharmaceutically-effective dose. In both prophylactic and therapeutic regimes, agents are usually administered in several dosages until a sufficient response has been achieved. An effective dose of the antibody-based molecule that binds to GPIIIa49-66 on activated platelets, for the purpose of reducing cerebral vascular platelet micro-clots will vary depending upon many different factors, including means of administration, target site, physiological state of the patient, whether the patient is human or an animal, and other medications administered.

In accordance with the prophylactic and therapeutic methods described herein, compositions comprising the antibody-based molecule that binds to GPIIIa49-66 are administered in a dosage ranging from about 0.0001 to 100 mg/kg, and more usually 0.01 to 10 mg/kg of the recipient's body weight. For example, the antibody-based molecule is administered in a dosage of 1, 2, 3, 4, 5, 6, 7, 8, 9 or 10 mg/kg, or higher, for example 15, 20, 25, 30, 35, 40, 45, 50, 55, 60, 65, 70, 75, 80, 85, 90, 95, or 100 mg/kg. An exemplary treatment regime entails administration once per every two weeks or once a month or once every 3 to 6 months. Intervals between single dosages can be weekly, monthly or yearly. Intervals can also be irregular as indicated by measuring blood levels of antibody in the patient. Alternatively, the antibody-based molecule can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The mode of administration of the antibody-based molecule that binds to GPIIIa49-66 or pharmaceutical composition comprising the same may be any suitable route that delivers the compositions to the host, such as parenteral administration, e.g., intradermal, intramuscular, intraperitoneal, intravenous or subcutaneous, pulmonary; transmucosal; using a formulation in a tablet, capsule, solution, powder, gel, particle; and/or contained in a syringe, an implanted device, osmotic pump, cartridge, micropump, or other means appreciated by the skilled artisan.

Administration can be systemic or local. In one embodiment, it may be desirable to administer the antibody-based molecule that binds to GPIIIa49-66 or pharmaceutical composition comprising the same locally to the area in need of treatment; this may be achieved by, for example, and not by way of limitation, local infusion, by injection, or by means of an implant. A suitable implant being of a porous or non-porous material, including membranes and matrices, such as sialastic membranes, polymers, fibrous matrices (e.g., Tissuel®), or collagen matrices.

In another embodiment, compositions containing antibody-based molecule that binds to GPIIIa49-66 or pharmaceutical composition comprising the same are delivered in a controlled release or sustained release system. In one embodiment, a pump is used to achieve controlled or sustained release. In another embodiment, polymeric materials can be used to achieve controlled or sustained release of the antibody-based molecule compositions described herein. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation is preferably inert, free of leachable impurities, stable on storage, sterile, and biodegradable. Also, the use of liposomes, microcapsules or microspheres, inclusion complexes, or other types of carriers known in the art are also contemplated.

In yet another embodiment, a controlled or sustained release system can be placed in proximity of the prophylactic or therapeutic target, thus requiring only a fraction of the systemic dose. Controlled and/or release systems for delivery of antibody-based molecules known in the art are suitable for use and delivery of compositions containing the antibodies and binding fragments thereof as described herein, see e.g., Song et al., "Antibody Mediated Lung Targeting of Long-Circulating Emulsions," *PDA Journal of Pharmaceutical Science & Technology* 50:372-397 (1995); Cleek et al., "Biodegradable Polymeric Carriers for a bFGF Antibody for Cardiovascular Application," *Pro. Int'l. Symp. Control. Rel. Bioact. Mater.* 24:853-854 (1997); and Lam et al., "Microencapsulation of Recombinant Humanized Monoclonal Antibody for Local Delivery," *Proc. Int'l. Symp. Control Rel. Bioact. Mater.* 24:759-760 (1997), each of which is incorporated herein by reference in their entireties.

In embodiments where a nucleic acid molecule, such as an mRNA molecule, encoding the antibody-based molecule as described herein is administered, the nucleic acid can be administered in vivo to promote expression of its encoded antibody-based molecule, by constructing it as part of an appropriate nucleic acid expression vector, e.g., by use of a retroviral vector (see e.g., U.S. Pat. No. 4,980,286 to Morgan et al., which is hereby incorporated by reference in its entirety). Alternatively, the nucleic acid can be administered by way of a delivery vehicle. Nanoparticle delivery vehicles and lipid-based particle delivery vehicles suitable for delivering mRNA and other nucleic acid molecules are well known in the art (see, e.g., Xiao et al., "Engineering Nanoparticles for Targeted Delivery of Nucleic Acid Therapeutics in Tumor," *Mol. Ther. Meth. Clin. Dev.* 12: 1-18 (2019) and Ni et al., "Synthetic Approaches for Nucleic Acid Delivery: Choosing the Right Carriers," *Life* 9(3): 59 (2019), which are hereby incorporated by reference in their entirety), and can be employed in the methods as described herein. For example, suitable lipid-based vehicles include cationic lipid based lipoplexes (e.g., 1,2-dioleoyl-3trimethylammonium-propane (DOTAP)), neutral lipids based lipoplexes (e.g., cholesterol and dioleoylphosphatidyl ethanolamine (DOPE)), anionic lipid based lipoplexes (e.g., cholesteryl hemi succinate (CHEMS)), and pH-sensitive lipid lipoplexes (e.g., 2,3-dioleyloxy-N-[2(sperminecarboxamido)ethyl]-N,N-dimethyl-1-propanaminium trifluoroacetate (DOSPA)). Other suitable lipid-based delivery particles incorporate ionizable DOSPA in lipofectamine and DLin-MC3-DMA ((6Z,9Z,28Z,31Z)-heptatriaconta-6,9,28,31-tetraen-19-yl-4-(dimethyl amino) butanoate).

Suitable delivery vehicles also include polymer-based particles, i.e., a polyplex. Suitable polyplex carriers comprise cationic polymers such as polyethylenimine (PEI), and/or cationic polymers conjugated to neutral polymers, like polyethylene glycol (PEG) and cyclodextrin. Other suitable PEI conjugates to facilitate nucleic acid molecule or expression vector delivery in accordance with the methods described herein include, without limitation, PEI-salicylamide conjugates and PEI-steric acid conjugate. Other synthetic cationic polymers suitable for use as a delivery vehicle material include, without limitation, poly-L-lysine (PLL), polyacrylic acid (PAA), polyamideamine-epichlorohydrin (PAE) and poly[2-(dimethylamino)-ethyl methacrylate] (PDMAEMA). Natural cationic polymers suitable for use as delivery vehicle material include, without limitation, chitosan, poly(lactic-co-glycolic acid) (PLGA), gelatin, dextran, cellulose, and cyclodextrin.

The methods described herein can also involve intranasal administration of the antibody-based molecule described herein, the antibody can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges composed of, e.g., gelatin, for use in an inhaler or insufflator may be formulated containing a powder mix of the compound and a suitable powder base such as lactose or starch.

In methods described herein involving oral administration of the antibody described herein, the antibody can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate).

In accordance the methods disclosed herein, the antibody-based molecule can be administered to a subject having cerebral vascular platelet micro-clots conjunction with a second therapeutic agent. In one embodiment, the antibody-based molecule and second therapeutic agent are administered concurrently. In one embodiment, the antibody based molecule and second therapeutic agent are administered sequentially.

For example, in one embodiment, the subject to be treated has Alzheimer's disease. Accordingly, the subject is treated with the antibody-based molecule as described herein along with an Alzheimer's disease therapeutic. Suitable Alzheimer's disease therapeutics to be administered in conjunction with the antibody-based molecule described herein include, without limitation, a cholinesterase inhibitor, an N-methyl D-aspartate (NMDA) antagonist, or a combination thereof.

Suitable cholinesterase inhibitors include, but are not limited to, donepezil (Aricept, Aricept ODT), tacrine (Cognex), rivastigmine (Exelon, Exelon Patch), galantamine (Razadyne or formerly Reminyl), memantine/donepezil (Namzaric), ambenonium (Mytelase), or neostigmine (Bloxiverz).

Suitable NMDA antagonists include, but are not limited to, memantine (Namenda XR), ketamine, dextromethorphan (DXM), phencyclidine (PCP), methoxetamine (MXE), or nitrous oxide ($N_2O$).

Other Alzheimer's disease therapeutics suitable for administration in combination with the antibody-based molecule that binds GPIIIa49-66 include agents that modulate innate immunity. In one embodiment, a suitable innate immunity modulating agent is an oligonucleotide bearing at least one unmethylated cytosine-guanosine (CpG) motif as disclosed in U.S. Pat. No. 10,960,019, which is hereby incorporated by reference in its entirety. Unmethylated CpG sequences are commonly found in prokaryotic and viral genomes but are underrepresented in eukaryotic genomes (Krieg et al., "CpG Motifs in Bacterial DNA and Their Immune Effects," *Annu. Rev. Immunol.* 20:709-760 (2002), which is hereby incorporated by reference in its entirety). Unless specifically designed to be methylated, CpG-containing DNA oligodeoxynucleotides (ODNs) synthesized in the laboratory or purchased from commercial suppliers are unmethylated. Specifically, CpG ODNs IMO-2055 and IMO-2125, developed as lead compounds for the treatment of cancer and hepatitis C, respectively (Agrawal and Kandimalla, "Synthetic Agonists of Toll-like Receptors 7, 8, and 9," *Biochem. Soc. Trans.* 35:1461-1467 (2007), which is hereby incorporated by reference in its entirety), would be particularly useful in the methods of the present invention. Additionally, CpG 7909 (5'-TCG TTT TGT CGT TTT GTC GTT-3', SEQ ID NO: 12) or analogs thereof, described in U.S. Patent Publication Nos. 2007/0012932 and 2006/0287263, both to Davis et al., which are hereby incorporated by reference in their entirety, or ODN 1018 ISS (5'-TGA CTG TGAACG TTC GAG ATG A-3', SEQ ID NO: 13) described in U.S. Patent Publication No. 2005/0175630 to Raz et al., which is hereby incorporated by reference in its entirety, would also be useful in carrying out the methods of the present invention. Other useful ODNs include, but are not limited to: ODN 1826 (5'-TCC ATG ACG TTC CTG ACG TT-3', SEQ ID NO: 14); ODN 1631 (5'-CGC GCG CGC GCG CGC GCG CG-3', SEQ ID NO: 15); ODN 1984 (5'-TCC ATG CCG TTC CTG CCG TT-3', SEQ ID NO: 16); ODN 2010 (5'-GCG GCG GGC GCG CGC CC-3', SEQ ID NO: 17); CpG 1758 (5'-CTC CCA GCG TGC GCC AT-3', SEQ ID NO: 18); CpG 2006 (5'-TCG TCG TTT TGT CGT TTT GTC GTT-3', SEQ ID NO: 19); CpG 1668 (5'-TCC ATG ACG TTC CTG ATG CT-3', SEQ ID NO: 20); and the like, as well as modifications thereof. In addition to CpG ODNs, CpG oligoribonucleotides (ORN) and oligodeoxyribonucleotides containing unmethylated CpG motifs. Exemplary CpG ORNs include those disclosed by Sugiyama et al., "CpG RNA: Identification of Novel Single-Stranded RNA that Stimulates Human CD14+CD11c+ Monocytes," *J. Immunology* 174:2273-79 (2005); U.S. Patent Publication No. 2005/0256073 to Lipford et al., which are hereby incorporated by reference in their entirety).

Other Alzheimer's disease therapeutics suitable for administering in combination with the antibody-based molecule that binds GPIIIa49-66 include disease modifying therapeutics that reduce amyloid and/or tau related pathology.

In one embodiment, the Alzheimer's disease modifying therapeutic is a monoclonal anti-amyloid antibody. Suitable monoclonal anti-amyloid antibodies include, but are not limited to, Aducanumab, BAN2401, Gantenerumab, Bapineuzumab, Crenezumab, Donanemab, Solanezumab, or a combination therapy of Gantenernumab and Solanezumab (see Cummings et al., "Alzheimer's Disease Drug Development Pipeline: 2020," *Alzheimer's Dement.* 6(1):e12050 (2020); Lacorte et al. "Safety and Efficacy of Monoclonal Antibodies for Alzheimer's Disease: A Systematic Review and Meta-Analysis of Published and Unpublished Clinical Trials," *Journal of Alzheimer's Disease* 87:101-129 (2022), which are hereby incorporated by reference in their entirety). Specifically, Aducanumab (Biogen) is a monoclonal antibody developed to remove fibrillary amyloid as a means of ameliorating progression of cognitive impairment in Alzheimer's disease. BAN2401 (Eisai and Biogen) is a monoclonal antibody developed to target prefibrillar amyloid and amyloid plaques. Gantenernumab (Roche) is a monoclonal antibody directed at plaques and oligomers to remove amyloid and reduce amyloid production. Bapineuzumab (Janssen, Pfizer) is a monoclonal antibody which targets the N-terminal region of Aβ. Crenezumab (AC Immune SA, Genentech, Hoffmann-La Roch) is a monoclonal antibody that recognizes multiple forms of aggregated Aβ, including oligomeric and fibrillar species and amyloid plaques with high affinity, and monomeric Aβ with low affinity. Donanemab (Eli Lilly & Co) is a monoclonal antibody that recognizes Aβ(p3-42), a pyroglutamate form of Aβ that is aggregated in amyloid plaques. Solanezumab (Eli Lilly and ATRI) is a monoclonal antibody directed at monomers, and promotes the removal of amyloid and prevents aggregation. The combination therapy of Gantenerrnumab and Solanezumab provides monoclonal antibodies directed at plaques, oligomers, and monomers to remove amyloid and reduce amyloid production. In one embodiment, the monoclonal anti-amyloid antibody is the monoclonal antibody Aducanumab.

In one embodiment, the Alzheimer's disease modifying therapeutic is a monoclonal anti-tau antibody. Suitable monoclonal anti-tau antibodies include, without limitation, gosuranemab (BIIB092), BIIB076, tilavonemab (ABBV-8E12), zagotenemab (LY3303560), bepranemab, and semorinemab (RO7105705) (see Ji et al., "Current Status of Clinical Trials on Tau Immunotherapies," *Drugs* 81(10): 1135-1152 (2021), which is hereby incorporated by reference in their entirety). Specifically, gosuranemab (BIIB092) (Biogen and Bristol-Myers Squibb) is a monoclonal anti-tau antibody targeting truncated form of tau. BIIB076 (Biogen) is a monoclonal antibody that removes tau and reduces tau propagation. Tilavonemab (ABBV-8E12) is a monoclonal anti-tau antibody that removes tau and prevents tau propagation. Zagotenemab (LY3303560; Eli Lilly) is a monoclonal antibody that removes tau and reduces tau propagation. Bepranemab (Hoffman-La Roche and UCB S.A.) is an anti-tau monoclonal antibody that binds to tau monomers and interferes aggregated tau. Semorinemab (RO7105705; Genentech) is a monoclonal antibody that removes extracellular tau.

Other suitable Alzheimer's disease therapeutics that can be administered in conjunction with the antibody-based molecule that binds GPIIIa49-66 include, without limitation, a SV2A modulator, a sigma non-opioid intracellular receptor-1 agonist, a RAGE antagonist, a muscarinic M2 antagonist, a tyrosine kinase inhibitor, a bacterial protease inhibitor, an omega-3 fatty acids, an angiotensin II receptor blocker, a calcium channel blocker, a cholesterol agent, an insulin sensitizer, an anti-viral agent, and any combination thereof (see Devanand et al., "Antiviral Therapy: Valacyclovir Treatment of Alzheimer's Disease (VALAD) Trial: Protocol For a Randomised, Double-Blind, Placebo-Controlled, Treatment Trial," *BMJ Open* 10(2):e32112 (2020), which is hereby incorporated by reference in their entirety).

Another aspect of the present disclosure is directed to a combination therapeutic that comprises an antibody-based molecule that binds to GPIIIa49-66 on activated platelets, and an Alzheimer's disease therapeutic.

As used herein, the term "combination therapy" or "combination therapeutic" refers to the administration of two or more therapeutic agents. In one embodiment, the antibody-based molecule and Alzheimer's disease therapeutic are administering concurrently. In another embodiment, the antibody-based molecule and Alzheimer's disease therapeutic are administering sequentially.

Combination therapy can provide a synergistic effect, as measured by, for example, the extent of the response, the response rate, the time to disease progression, or the survival period, as compared to the effect achievable on dosing with the either therapeutic alone at its conventional dose. For example, the effect of the combination treatment is synergistic if a beneficial effect is obtained in a patient that does not respond (or responds poorly) to the either therapeutic alone. In addition, the effect of the combination treatment is defined as affording a synergistic effect if the either therapeutic is administered at dose lower than its conventional dose and the therapeutic effect, as measured by, for example, the extent of the response, the response rate, the time to disease progression or the survival period, is equivalent to that achievable on dosing conventional amounts of primary therapeutic. In particular, synergy is deemed to be present if the conventional dose of either therapeutic is reduced without detriment to one or more of the extent of the response, the response rate, the time to disease progression, and survival data, in particular without detriment to the duration of the response, but with fewer and/or less troublesome side-effects than those that occur when conventional doses of each component are used.

In accordance with this aspect of the disclosure, the combination therapeutic comprises an antibody-based molecule that binds to GPIIIa49-66 and activated platelets. Suitable antibody-based molecules that bind to GPIIIa49-66 and nucleic acid molecule encoding the same that are suitable for inclusion in this combination therapeutic supra. The combination therapeutic further comprises an Alzheimer's disease therapeutic. Suitable Alzheimer's disease therapeutics are also disclosed above and include, without limitation, cholinesterase inhibitors, N-methyl D-aspartate (NMDA) antagonists, or combinations thereof; a disease modifying therapeutic that reduces amyloid and/or tau related pathology, such as monoclonal anti-amyloid antibodies (e.g., Aducanumab, BAN2401, Gantenerumab, Bapineuzumab, Crenezumab, Donanemab, Solanezumab) and monoclonal anti-tau antibodies (e.g., gosuranemab, BIIB076, tilavonemab, zagotenemab, bepranemab, and semorinemab); and agents that modulates innate immunity (e.g., an oligonucleotide bearing at least one unmethylated CpG motif as described in U.S. Pat. No. 10,960,019, which is hereby incorporated by reference in its entirety).

Other suitable Alzheimer's disease therapeutics that can be included in a combination therapeutic as encompassed by the present disclosure include, without limitation, a SV2A modulator, a sigma non-opioid intracellular receptor-1 agonist, a RAGE antagonist, a muscarinic M2 antagonist, a tyrosine kinase inhibitor, a bacterial protease inhibitor, an omega-3 fatty acids, an angiotensin II receptor blocker, a calcium channel blocker, a cholesterol agent, an insulin sensitizer, and an anti-viral agent, and any combination thereof.

EXAMPLES

The following Examples are presented to illustrate various aspects of the disclosure, but are not intended to limit the scope of the claimed invention.

Materials and Methods For Examples

Reagents—All reagents were purchased from Sigma-Aldrich (St. Louis, MO, USA) unless otherwise indicated. Soluble Aβ (1-40) (Shenggong Co., Ltd., Shanghai) sequence (single-letter code), DAEFRHDSGYEVHHQKLVFFAEDVGSNKGAIIGLMVGGVV, SEQ ID NO: 21) was used. Human monoclonal single-chain variable fragment (scFv) antibody (Ab) against platelet GPIIIa49-66 (A11) and control scFv Ab were prepared as previously described. Zhang et al., "Dissolution of Arterial Platelet Thrombi In Vivo With a Bifunctional Platelet GPIIIa49-66 Ligand Which Specifically Targets the Platelet Thrombus," *Blood* 116:2336-44 (2010), which is hereby incorporated by reference in its entirety.

Animals—3×Tg mice (human APP KM670/671NL (Swedish), MAPT P301L, and PSEN1 M146 V) exhibiting amyloid and tau pathologies and B6129S control mice were purchased from the Jackson Laboratory (Bar Harbor, ME) and were used to conduct the experiments described. The animals were maintained in an environmentally controlled room at 22°±1° C. with a 12 h light/dark cycle in a specific pathogen-free facility at the East China Normal University (Shanghai, China). All mice were housed in clear polycarbonate micro-isolator cages (five mice per cage), allowed free access to water and food. Both males and females were included in approximately equal ratios for all experiments. The detailed number, age and sex of mice used for the each experiment are shown in the figure legends. All procedures in the animal experiments were approved by the Institutional Animal Care and Use Committee of East China Normal University. All methods were performed in accordance with the relevant guidelines and regulations.

Experimental Design

Experimental Animal Model of Atherosclerosis—There were three experimental groups: 3×Tg mice on a high-fat diet (HFD), 3×Tg mice on a normal diet, and B6129S mice on a normal diet. The 3×Tg mice were randomly separated into two groups. The HFD containing 1.25% cholesterol in order to induce atherosclerosis. The control group 3×Tg mice were fed normal chow. B6129S control mice were also fed normal chow and served as a comparison group to evaluate if 3×Tg mice on normal chow have any alterations in hematological parameters and/or vascular permeability. HFD treatment was initiated at 3 months of age, which corresponds to early adulthood in humans. Most mice were fed a HFD for 9 months and samples were collected at 12 months of age for the subsequent assays. To investigate the initial signs of AD vascular lesions, 2-3 mice in each group were randomly selected and monitored at 6 and 9 month time points. At the end of treatment (12 months of age), animal behavior was analyzed by an observer blinded to the treatment status of the mice. Before assessment of cognitive deficits and locomotor testing, the body weight of each mouse was weighted to ensure that any behavioral differences observed in the tasks tested could not be related to differences in body weight (e.g., HFD mice being obese). Serum total cholesterol (TC) was measured with commercial ELISA kits according to the manufacturer's instructions of the ELISA kit (LYBD Bio-Technique Co, Ltd, Beijing, China). Oil red O staining was used to assess the size of the atherosclerotic lesion and its lipid content. Briefly, mice were sacrificed by the cervical dislocation. Thoracic-abdominal aortas (TAs) were dissected, and oil red O staining of the artery plaque area was performed. For quantification, ImageJ version 1.50i (NIH, Bethesda, MD) was used to measure the lesion size of TAs.

In Vivo Assessment of Cerebral Blood Vessel Permeability—In this experiment, 12-month-old 3×Tg mice fed by HFD or normal chow as well as age- and sex-matched B6129S control mice fed by normal diet were used to assess cerebral blood vessel permeability. B6129S control mice were used to see if 3×Tg mice alone have the alterations in vascular permeability. Cerebral blood vessel permeability assay was performed using Evans Blue dye as previously described. Radu et al., "An In Vivo Assay to Test Blood Vessel Permeability," *J. Vis. Exp.* e50062 (2013), which is hereby incorporated by reference in its entirety. The rational is as follows: Evans blue is a diazo salts fluorescent dye with high affinity (10:1) for albumin (the most abundant protein in plasma), and presents red fluorescence under the excitation of 550 nm. Under physiologic conditions the endothelium is impermeable to albumin, so Evans blue bound albumin remains restricted within blood vessels. In pathologic conditions that promote increased vascular permeability endothelial cells partially lose their close contacts and the endothelium becomes permeable to small proteins such as albumin. This condition allows for extravasation of Evans Blue in tissues. Briefly, a 0.5% sterile solution of Evans blue was prepared in phosphate buffer saline (PBS), and the solution was filter-sterilized to remove any particulate matter that was not dissolved. Evans blue solution (4 ml/kg) was slowly injected through the tail vein of the mouse. Evans blue dye was allowed to circulate for 30 min. Animals were then perfused transcardially with PBS until fluid from the right atrium became colorless. All the mice were sacrificed at the same time, as fast as possible. The brains were harvested immediately, the cerebellum was removed, and the remainder was split in half into two hemispheres. One half of brains were sliced into 35 μm sections using a cryostat. Tissue sections were thaw-mounted directly onto glass slides and stored at −80° C. until use. The level of cerebral vascular permeability can be assessed by simple visualization of brain section under the excitation of 550 nm by fluorescence microscope. The other half brains were used for quantification of Evans blue extravasated in tissue. Briefly, brain dye was extracted with formamide overnight at 50° C. Subsequently, brains were allowed to dry for 1 h at room temperature (RT) before being weighed. Formamide dye concentration was quantified spectrophotometrically at 611 nm and normalized to the dry weight of brain hemispheres.

Post-ischemic stroke model—To assess if HFD treatment promotes ischemic-related tau hyperphosphorylation in 3×Tg mice, some 12-month-old HFD-treated and normal diet-treated 3×Tg mice were subjected to transient middle cerebral artery occlusion (tMCAO) to induce cerebral ischemia reperfusion injury as previously described. Zhang et al., "Dissolution of Arterial Platelet Thrombi In Vivo With a Bifunctional Platelet GPIIIa49-66 Ligand Which Specifically Targets the Platelet Thrombus," *Blood* 116:2336-44 (2010), which is hereby incorporated by reference in its entirety. Briefly, a 3×0.2-mm polyethylene thread attached to a 9-mm 7/0 suture was inserted into the right internal carotid artery and advanced to the bifurcation of the middle cerebral artery. The polyethylene thread was removed 90 min after placement, and all treated mice were sacrificed at 48 h and mouse brains were dissected for triphenyltetrazolium chloride (TTC) staining or the analysis of tau hyperphosphorylation, respectively.

In Vivo Assessment of the Effect of A11 on AD Pathology—A11 is a humanized scFv Ab that preferentially binds to activated platelets and can lyse platelet thrombi (Zhang et al., "Dissolution of Arterial Platelet Thrombi In Vivo With a Bifunctional Platelet GPIIIa49-66 Ligand Which Specifically Targets the Platelet Thrombus," *Blood* 116:2336-44 (2010), which is hereby incorporated by reference in its entirety). To investigate the effect of A11 on AD pathology, 6-month-old HFD-treated 3×Tg mice were randomly separated into two groups and intraperitoneally injection (i.p.) by A11 or control scFv Ab (25 μg/mouse) 2 times every week for 3 months. Then, mouse behavior and vascular permeability were analyzed. The overall behavior of each mouse was monitored by homecage activity monitoring system for 15 min and analyzed by automated animal behavior analysis (HomeCageScan, CleverSys, Inc., USA). Memory deficits were also assessed using contextual fear conditioning.

Brain and Serum Sampling—Mice were sacrificed by cervical dislocation, and brain tissue was dissected from mice, weighed, and homogenized in 0.1 M PBS buffer (pH 7.4) containing protease inhibitor cocktail at 1 g/10 mL at 4° C. After centrifugation at 12,000×g for 10 min, the supernatant was collected for subsequent biochemical analysis. For serological analysis, mice were deeply anesthetized by i.p. injection of pentobarbital (50 mg/kg body weight) and blood was collected from the retro-orbital sinus. Blood was allowed to clot, then centrifuged at 3000×g for 5 min and sera frozen at −80° C. until analysis.

Sandwich ELISA and Western Blotting—The concentrations of serum IL-6 and TPO, and the concentrations of reactive oxygen species (ROS), glutathione (GSH), and endostatin (ET) in brain tissues were measured by Sandwich ELISA according to the manufacturer's instructions of the ELISA kit (LYBD Bio-Technique Co, Ltd, Beijing, China). For Western blotting, proteins were separated on sodium dodecyl sulfate polyacrylamide gel electrophoresis (SDS—PAGE) under reducing conditions and then transferred onto a polyvinylidene difluoride (PVDF) membrane. The membrane was blocked in blocking buffer [PBS, 0.5% Tween-20, and 5% non-fat dry milk powder or 3% bovine serum albumin (BSA)] and then incubated with primary antibody for 1 h at RT. After washing, the membrane was incubated with horseradish peroxidase (HRP)-conjugated secondary antibody for 1 h at RT. The immunoreactive bands were visualized with enhanced chemiluminescence (ECL) Western blot kit (Millipore, Boston, MA, USA), and quantified using ImageJ version 1.50i.

Quantitative Real-Time RT-PCR Analysis—RNA was extracted from liver tissue using an RNeasy Mini Kit (Qiagen). The cDNA fragments were reverse-transcribed from mRNA using a high-capacity cDNA reverse transcription kit (Thermo Fisher). Quantitative real-time RT-PCR (qRT-PCR) was performed using the Step One Plus real-time PCR system (ThermoFisher, Carlsbad, CA) with SuperReal PreMix Plus (SYBR Green; TIANGEN). The mouse thrombopoietin (Tpo) primers were:

```
Forward primer
(5'-CCAGGTCCCCAGTCCAAATC-3', SEQ ID NO: 22);
and

Reverse primer
(5'-AATGCCAGGGAGCCTTTGTT-3') (SEQ ID NO: 23).
```

The relative quantity of Tpo mRNA was determined using the ΔΔCt method, with Gapdh as the reference gene. All reactions were performed in triplicates.

Murine Platelet Preparation and Function Testing—Murine blood from retro-orbital plexus was collected and centrifuged at 250×g for 5 min at RT. To obtain platelet-rich plasma (PRP), the supernatant was centrifuged at 50×g for 6 min. PRP was washed twice at 650×g for 5 min at RT, and pellet was resuspended in Tyrode's buffer (136 mM NaCl, 0.4 mM Na2HPO4, 2.7 mM KCl, 12 mM NaHCO3, 0.1% glucose, 0.35% BSA, pH 7.4) supplemented with prostacyclin (0.5 mM) and apyrase (0.02 U/ml). Before use, platelets were resuspended in the same buffer and incubated at 37° C. for 30 min. To determine the bleeding time, the mouse tail vein was severed 2 mm from its tip. Immediately after injury, the tail was placed into a cylinder with isotonic saline at 37° C. and bleeding time was measured from the moment the tail was surgically cut until bleeding completely stopped. Platelet counts and mean platelet volume (MPV) were determined by an auto hematology analyzer. The expressions of platelet glycoprotein GPIIb (αIIb or CD41) and GPIIIa (β3 or CD61) were determined by flow cytometry and Western blotting, respectively.

Murine Platelet Culture, Congo Red Staining and Immunofluorescence Analysis—Mouse platelets from different treatment group were cultured in a concentration of $2\times10^6$ per 100 μl in sterilized glass plate placed in 96 well plate containing DMEM medium and stimulated with 50 μg/ml Aβ40 for 48 h at 37° C. After incubation, unbound platelets were removed by rinsing with PBS, whereas adherent platelets were fixed with 2% paraformaldehyde and stained for fibrillar Aβ aggregates with Congo red according to the manufacturer's protocol (Merck). Images of fibrillar Aβ aggregates in the platelet cell culture were then photographed by microscope. To determine the effect of A11 on the formation of fibrillar Aβ aggregates in vitro, different concentrations of A11 (0, 10 and 25 μg/ml) and control scFv Ab were simultaneously added to culture systems for 48 h at 37° C. and the positively stained fibrillar Aβ aggregates were enumerated under the microscope. For immunofluorescence analysis, the mouse platelet and fibrillar Aβ aggregates in sterilized glass plate were separately stained with anti-GPIbα (rat origin) and anti-Aβ (anti-β-Amyloid, 1-16 antibody, rabbit origin) at 4° C. overnight, then incubated with Cy3-labeled (anti-rat) or FITC-labeled (anti-rabbit) secondary antibody (reacted with anti-GPIbα and anti-Aβ, respectively) at RT for 1 h. Images were obtained by Leica SP8 confocol microscope (Leica.Microsystems, Wetzlar, Germany).

Histology Analysis—Mice were deeply anesthetized by i.p. injection of pentobarbital and subjected to trans-cardiac perfusion with 0.9% saline buffer followed by 4% paraformaldehyde (PFA) at a slow, consistent rate. Brains were post-fixed overnight in 4% PFA and cryoprotected for 72 h in 30% sucrose solution. Brains were then frozen on powdered dry ice and sliced into 35 μm sections using a microtome. The vascular and parenchymal Aβ deposits in brain tissue sections were visualized with Congo red staining as previously described (Donna et al., "Quantification of Cerebral Amyloid Angiopathy and Parenchymal Amyloid Plaques With Congo Red Histochemical Stain," *Nat. Protoc.* 1:1591-5 (2006), which is hereby incorporated by reference in its entirety). In brief, sections were stained with Congo red and images were collected at the selected regions from frontal cortex to hippocampus of each mouse brain under the same illumination conditions. Quantification of Congo red staining was performed using the Image J software for separately quantifying vascular and parenchymal amyloid deposits in brain tissue sections. For immunofluorescence analysis, brain sections were incubated with anti-Aβ, anti-glial fibrillary acidic protein (GFAP), anti-GPIbα, anti-NeuN, or anti-phospho-Tau396 antibodies. Following three washes of 10 min each with Tris buffered saline (TBS), sections were incubated for 2 h with secondary antibodies conjugated to specific fluorophores for detection. Controls with no primary antibody showed no fluorescence. Samples were counterstained with 4',6-diamidino-2-phenylindole (DAPI) and imaged with a Leica SP8 confocal microscope. Densitometric analysis of immunofluorescence was performed by using the fluorescence measuring function of ImageJ version 1.50i.

Transmission Electron Microscopy (TEM)—Mice were anesthetized and perfused as described above. Brain tissues were fixed with 2.5% glutaraldehyde at 4° C., followed by fixation with osmium tetroxide, dehydration in alcohol, embedding in plastic, ultra-thin sectioning, flotation of the sections on aqueous medium, and staining with uranyl acetate and lead acetate. Images were taken with a Tecnai G2 Spirit BioTWIN transmission electron microscope (FEI, Hillsboro, Oregon).

Contextual Fear Conditioning Test—Contextual fear conditioning was performed to assess associative emotional memory of mice as described previously. Phillips R G and LeDoux J E, "Differential Contribution of Amygdala and Hippocampus to Cued and Contextual Fear Conditioning," *Behav. Neurosci.* 106:274-85 (1992), which is hereby incorporated by reference in its entirety. In training phase, each mouse was pre-exposed to the shock chamber and allowed to explore the environment for 3 minutes and a subsequent foot shock (0.5 mA) for 2 seconds. The mice were allowed to stay in the chamber for another 30 s, and then they were placed back into their home cages. The training phase was conducted for 2 days. Approximately 24 h after training, each mouse was placed back into the shock chamber for 3 minutes during which the freezing behavior of mouse was recorded (contextual fear conditioning).

Statistics—Data were analyzed by Student's t test using the software package Prism version 7 (GraphPad, La Jolla, CA, USA). Data are shown as mean±SD. Ap value<0.05 was considered statistically significant.

Example 1—HFD-Induced Atherosclerosis Facilitates Memory Deficits

Figure 1B:
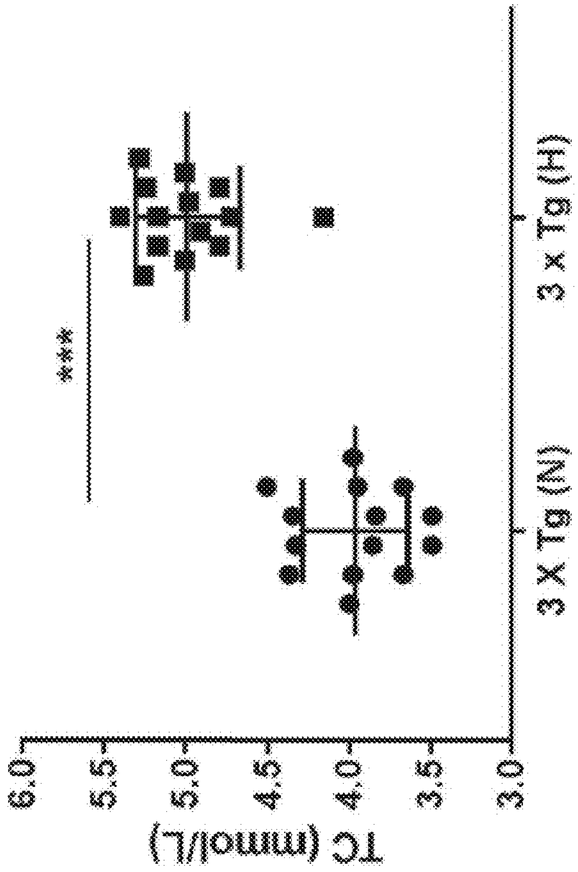
Figure 1C:
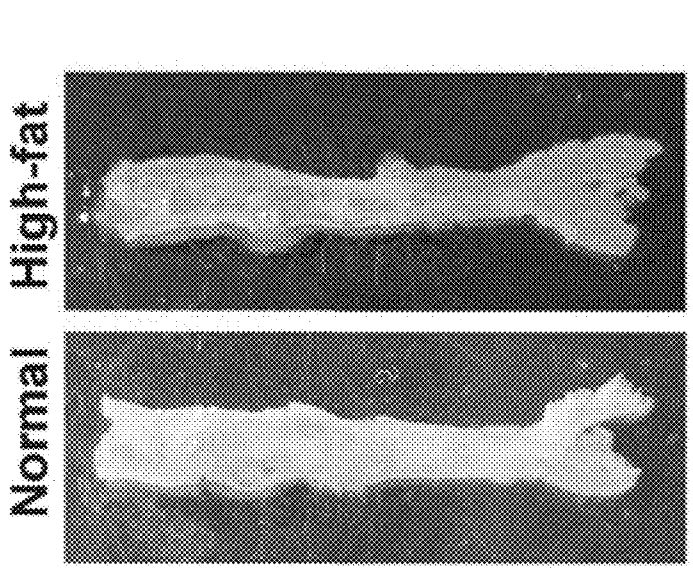
Figure 1D:
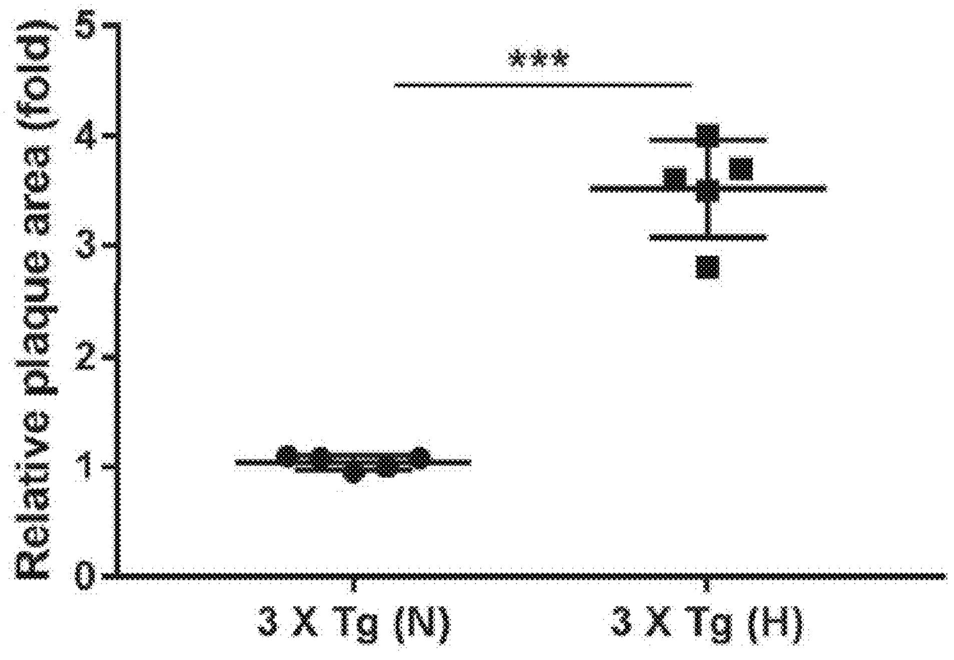
Figure 1E:
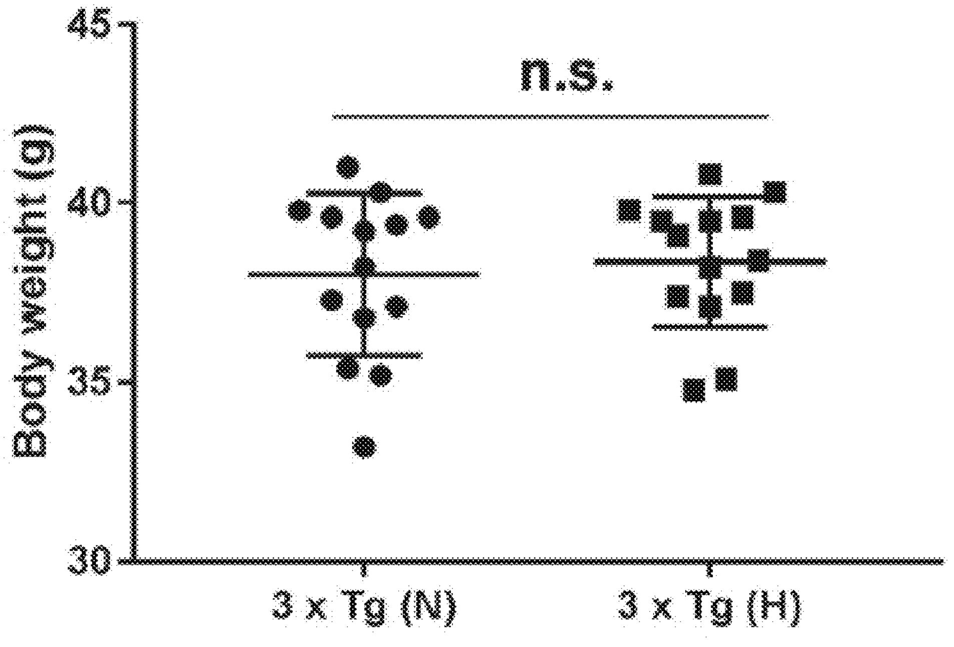
Figure 1F:
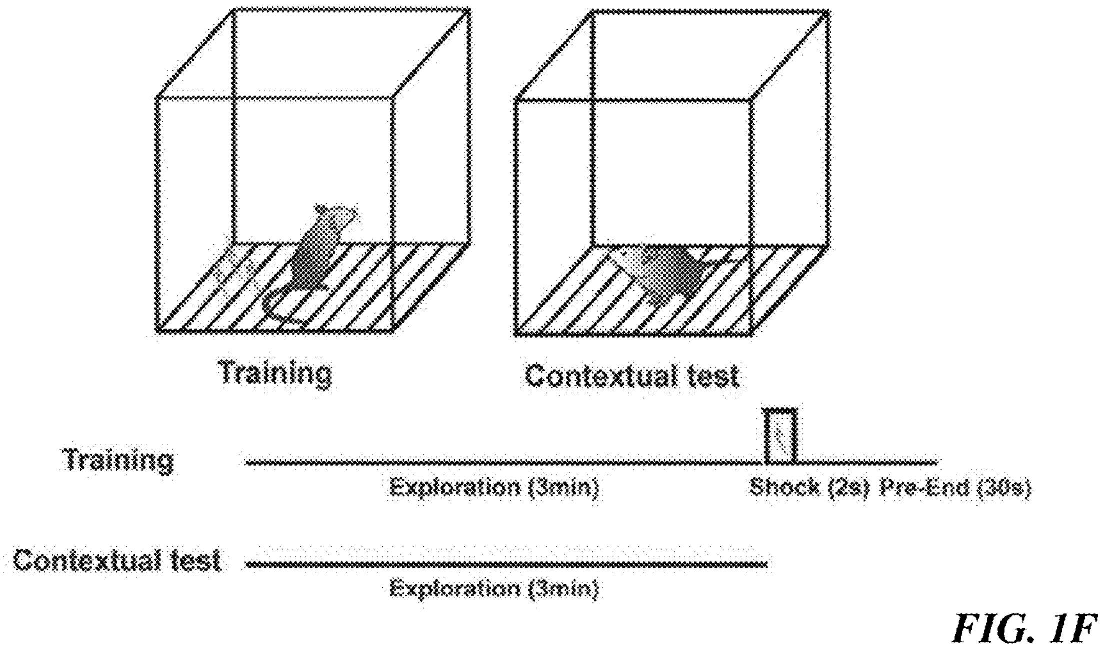
Figure 1G:
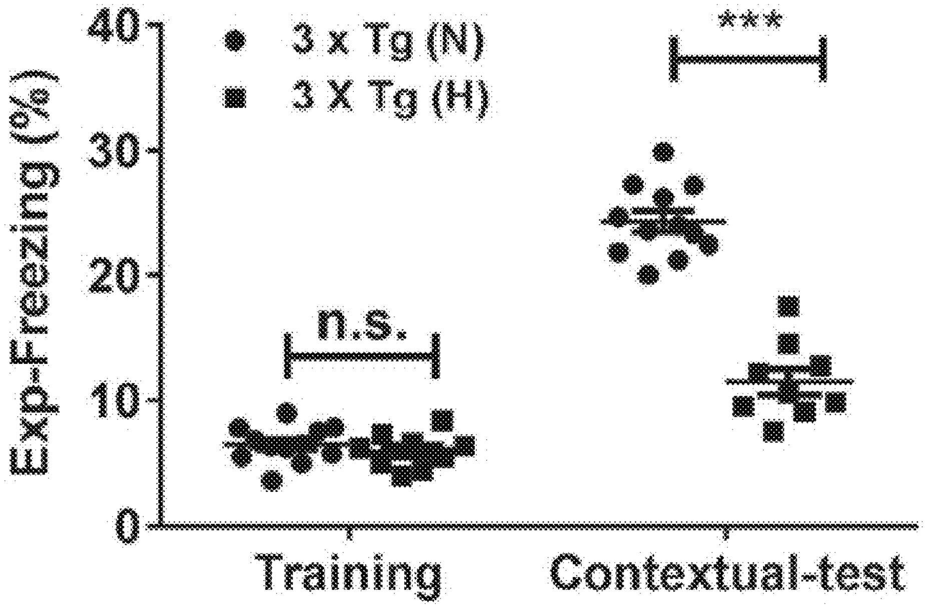

To mimic the chronic pathological progress of atherosclerosis, 3-month-old 3×Tg mice, which corresponds to early adulthood in humans, were fed with HFD for 9 months and were analyzed at 12 months of age (FIG. 1A). After 9 months of treatment, HFD-treated 3×Tg mice exhibited a significant increase in serum total cholesterol compared to normal chow-treated $3\times T_g$ mice (FIG. 1B). Oil red O staining showed that artery plaque area in thoracic-abdominal aorta of HFD-treated 3×Tg mice was significantly increased by approximately 3.7-fold in comparison to that of normal chow-treated mice (FIGS. 1C and 1D, respectively). There was no significant difference in body weight between the two groups (FIG. 1E). For cognitive testing, associative emotional memory was assessed through hippocampus-dependent contextual fear conditioning (FIG. 1F). HFD-treated 3×Tg mice showed significantly decreased contextual fear freezing time (FIG. 1G), indicating that HFD-induced atherosclerosis facilitates memory deficits.

Example 2—HFD-Induced Atherosclerosis Causes Blood Hypercoagulation

To determine whether the memory deficits observed in HFD-treated 3×Tg mice is caused by atherosclerosis-induced circulatory deficits, blood serums from HFD-treated and normal-chow 3×Tg mice were analyzed by label-free mass spectrometry (MS). A total of 1790 proteins were identified. The abundance of 86 proteins (4.8%) was significantly different between these two different cohorts. Gene ontology (GO) term and pathway analyses of significantly changed proteins by Metascape revealed enrichment of proteins of several pathways related to complement and coagulation cascades, blood coagulation, platelet degranulation, and cell-substrate adhesion. The related molecules include vWF, Complement (C)3, C5, Cfi, Alpha-1-antitrypsin (SERPINA1), Apolipoprotein A-I (APOA1), Inter-alpha-trypsin inhibitor heavy chain H1 (ITIH1), Fibulin-1 (FBLN1), and Gelsolin (GSN) (Additional file 1, TableS2).

Figure 2A:
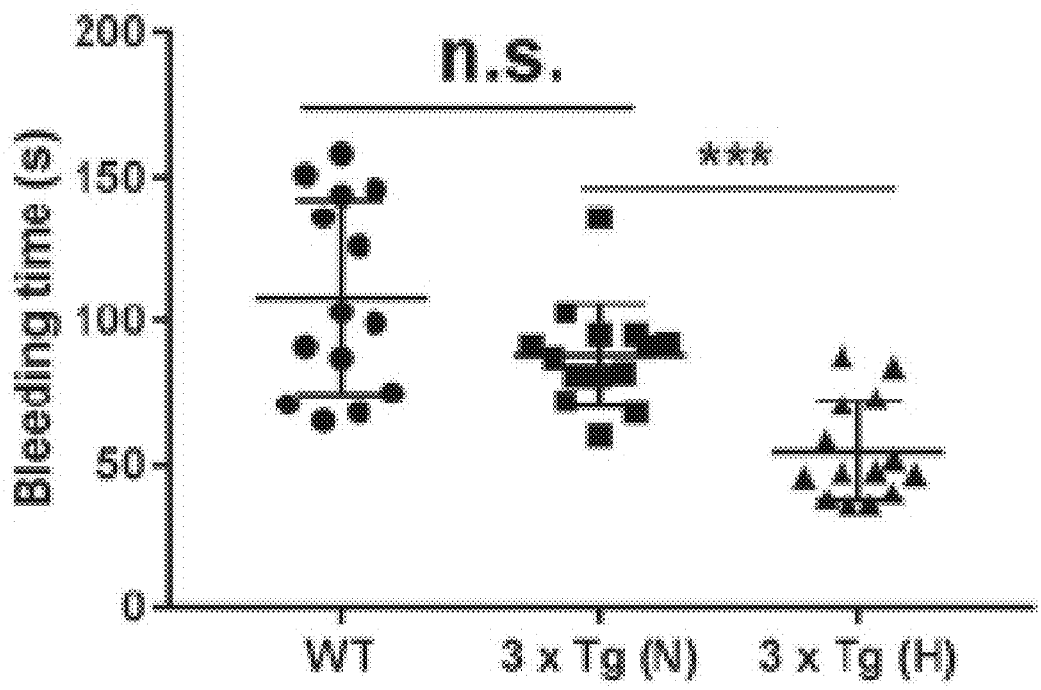
FIGS. 2A-2H show increased blood coagulation, platelet size and platelet production in HFD-treated 3×Tg mice.
Figure 2B:
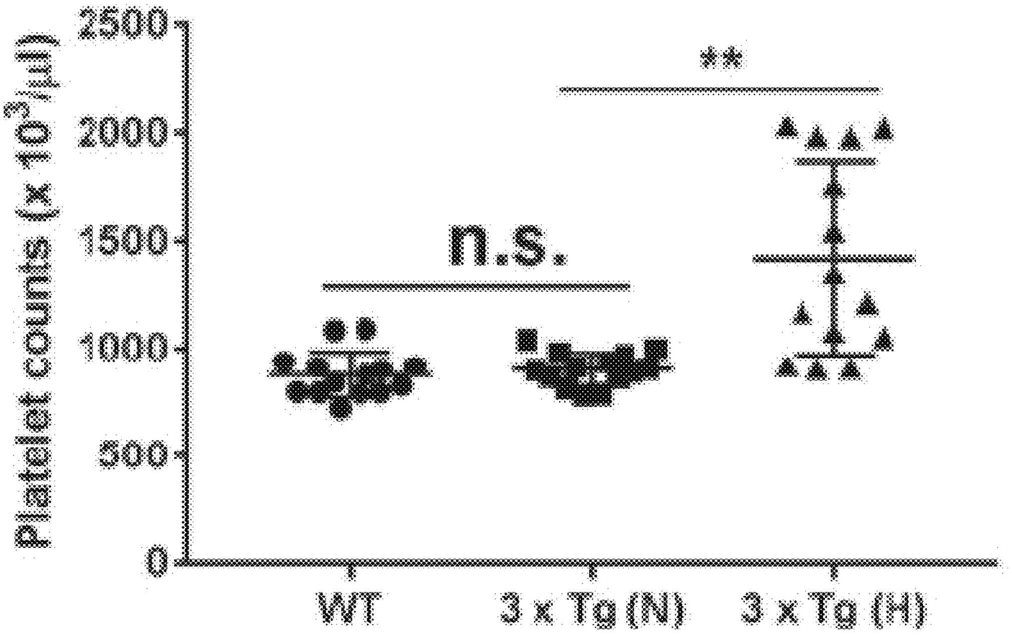
Figure 2C:
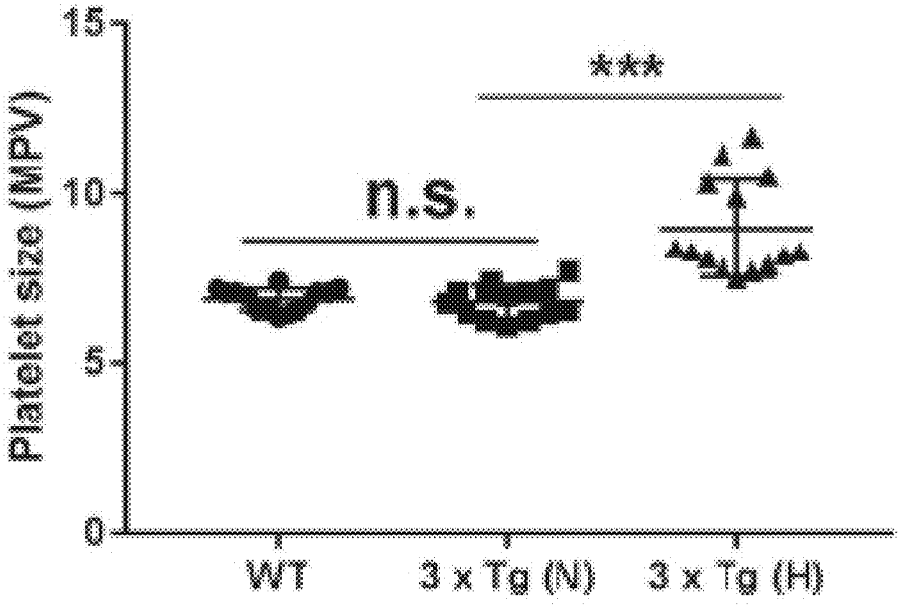

Example 3—Reduced Bleeding Time, Increased Platelet Size and Platelet Numbers in HFD-Treated 3×Tg Mice The coagulation function in mice was further assessed. HFD-treated 3×Tg mice showed a significant reduction in bleeding time and an increase in platelet counts and MPV compared to those of normal chow-treated 3×Tg mice; these hematological parameters showed no significant differences between normal chow-treated 3×Tg mice and B6129S WT control mice (FIGS. 2A-2C, respectively). HFD-treated 3×Tg mice also exhibited significant elevation of serum IL-6

Figure 2D:
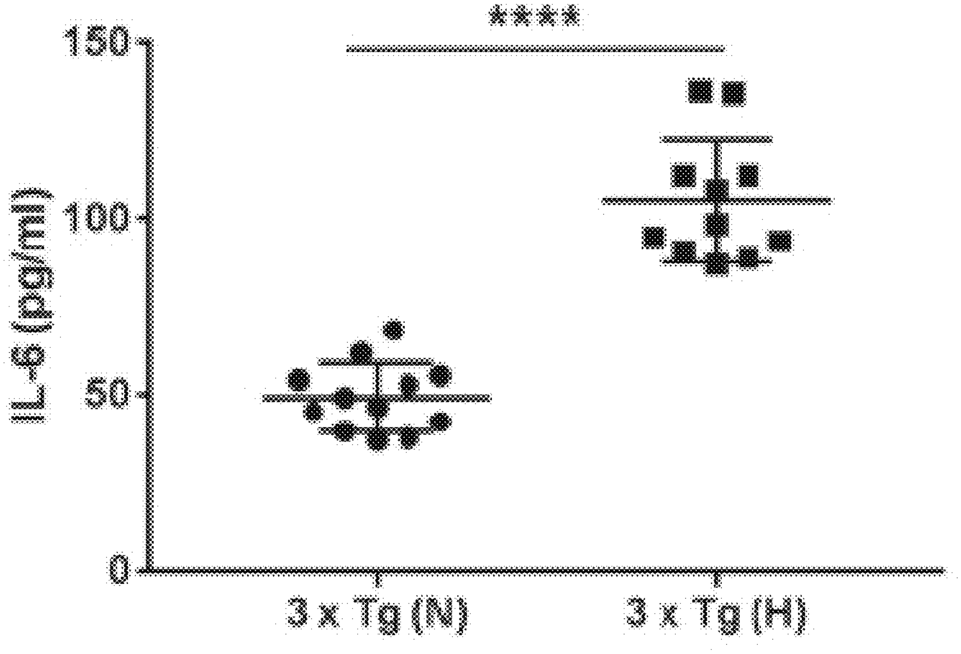
Figure 2E:
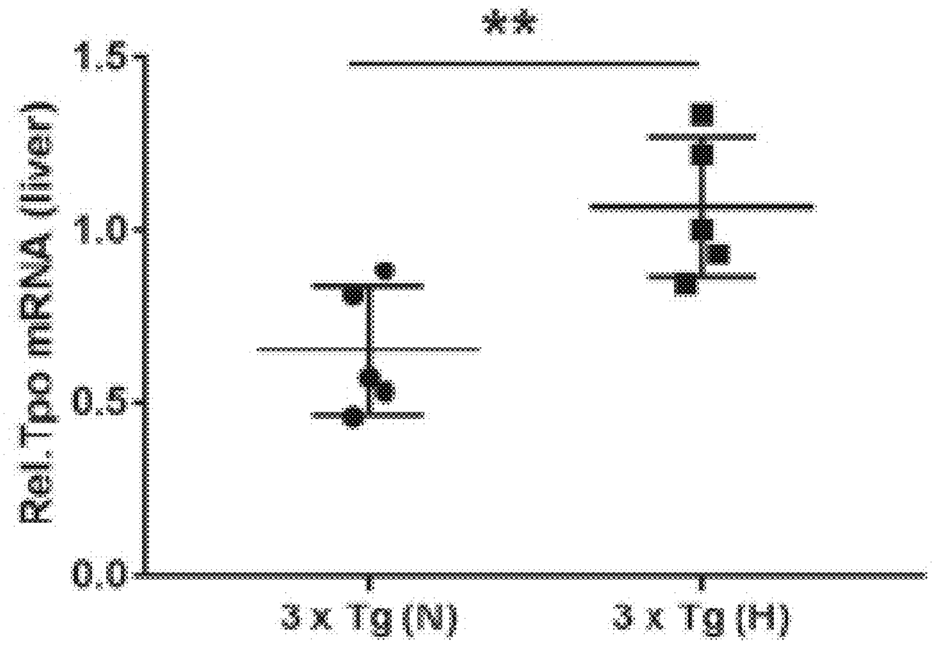
Figure 2F:
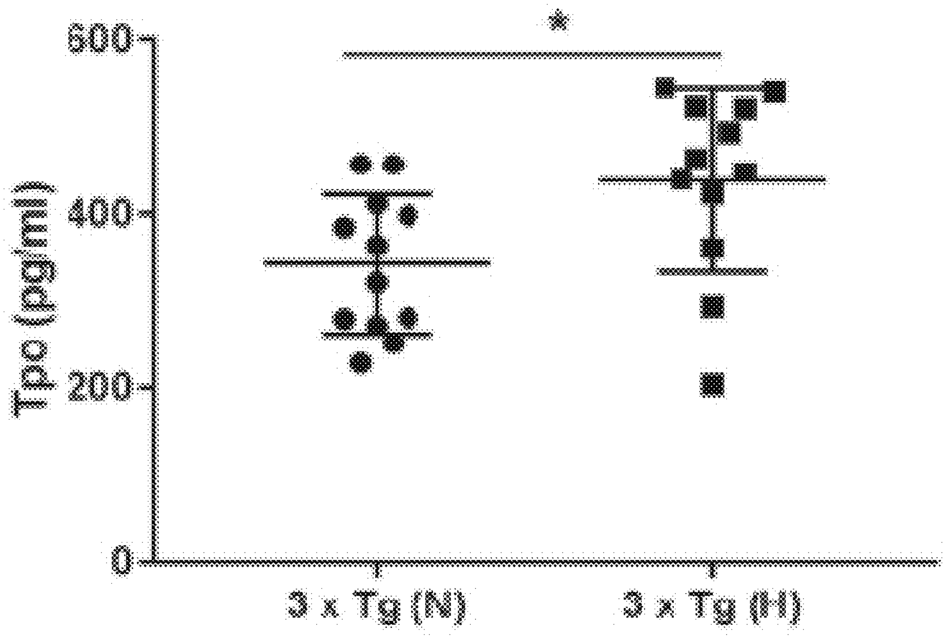
Figure 2G:
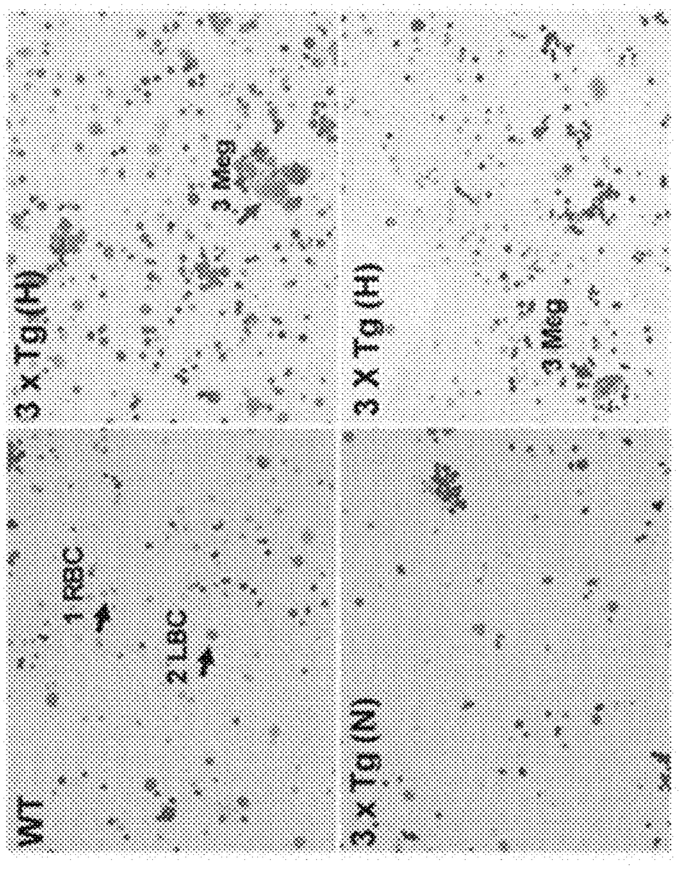
Figure 2H:
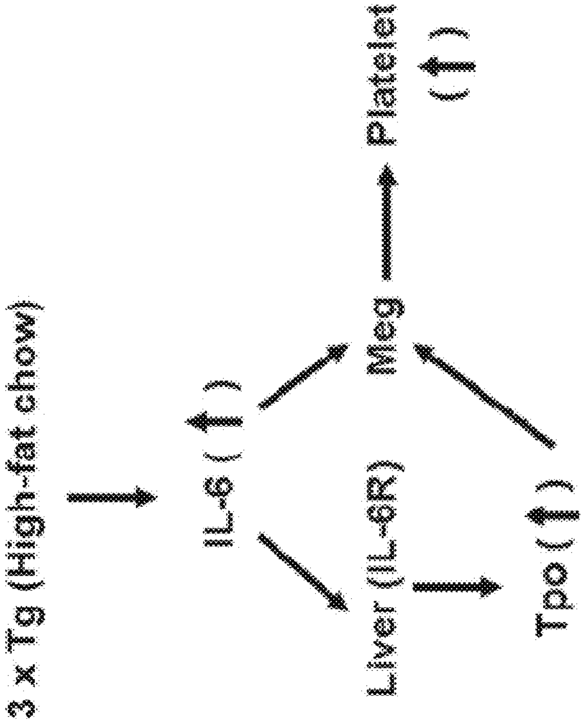

(FIG. 2D), which is an important pro-inflammatory cytokines stimulating megakaryocytes (MKs) to produce blood platelets. Akkerman J W, "Thrombopoietin and Platelet Function," *Semin. Thromb. Hemost.* 32:295-304 (2006), which is hereby incorporated by reference in its entirety. Given that IL-6 could bind with liver IL-6 receptor (IL-6R) and results in increased TPO generation, the levels of TPO were examined. TPO is mainly produced by hepatocytes and interacts with the c-Mpl receptor expressed on megakaryocytic lineage cells in the bone marrow, which contributes to the differentiation of MKs from hematopoietic stem cells and the generation of platelets. Kaushansky K, "The Molecular Mechanisms That Control Thrombopoiesis," *J. Clin. Invest.* 115:3339-47 (2005), which is hereby incorporated by reference in its entirety. The qRT-PCR analysis showed that liver Tpo mRNA was 1.4-fold higher in the HFD-treated mice than in the normal chow-treated mice (FIG. 2E). Serum TPO levels also exhibited a significant increase in HFD-treated 3×Tg mice (FIG. 2F). Megakaryocytes were detectable in bone marrow smear in the HFD-treated 3×Tg mice (FIG. 2G). These data suggest that HFD treatment promotes platelet production (thrombocytosis) associated with elevated IL-6 and TPO levels (FIG. 2H).

Figure 3A:
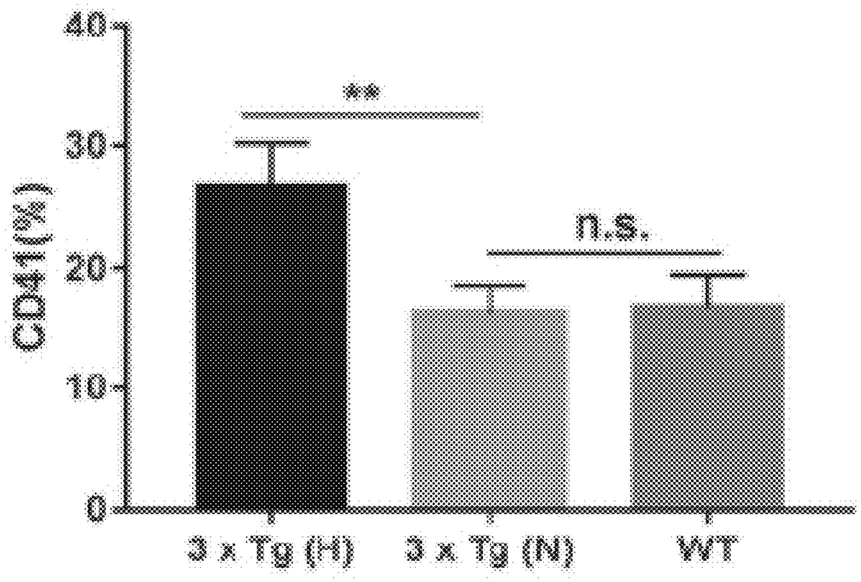
FIGS. 3A-3H show that platelets from HFD-treated 3×Tg mice actively induce the formations of fibrillar Aβ aggregates in association with increased integrin $\alpha_{IIb}\beta_3$ and clusterin (CLU) expression.
Figure 3B:
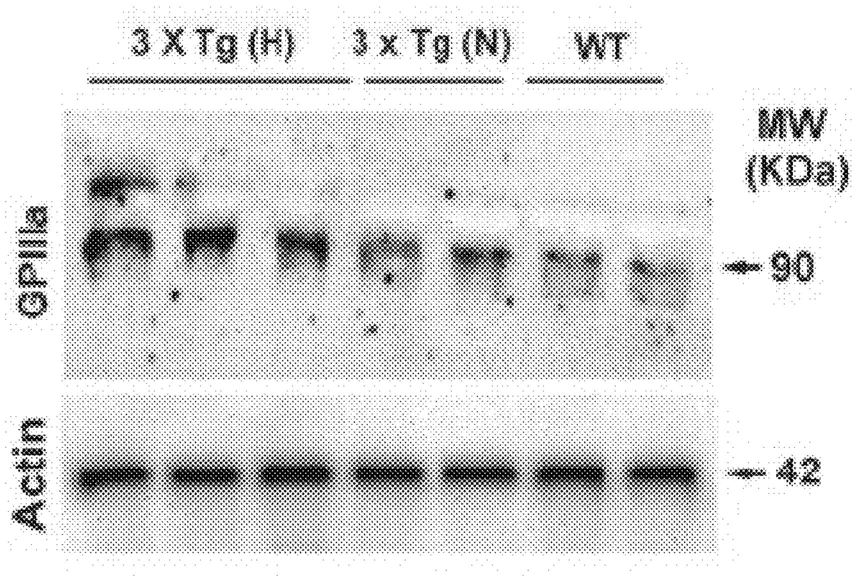
Figure 3C:
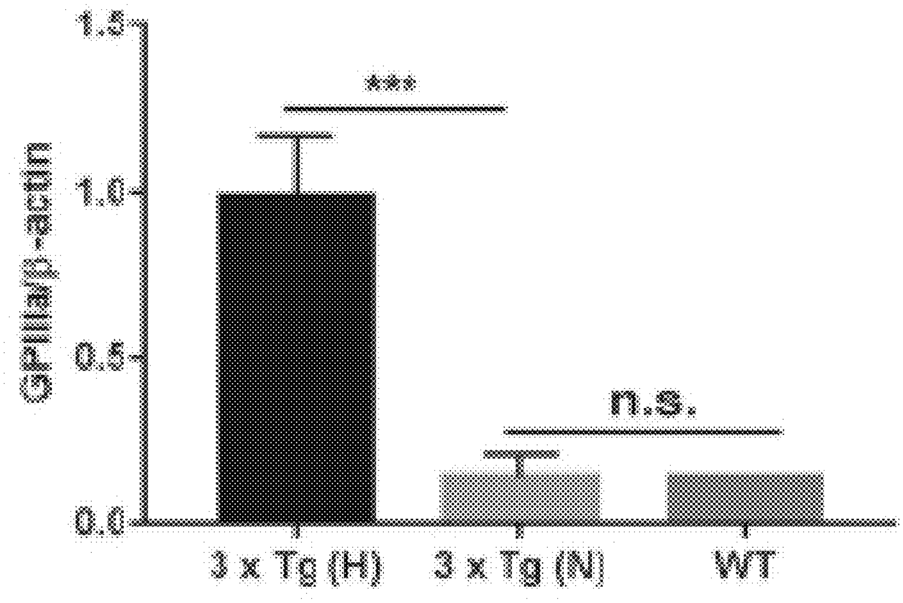
Figure 3D:
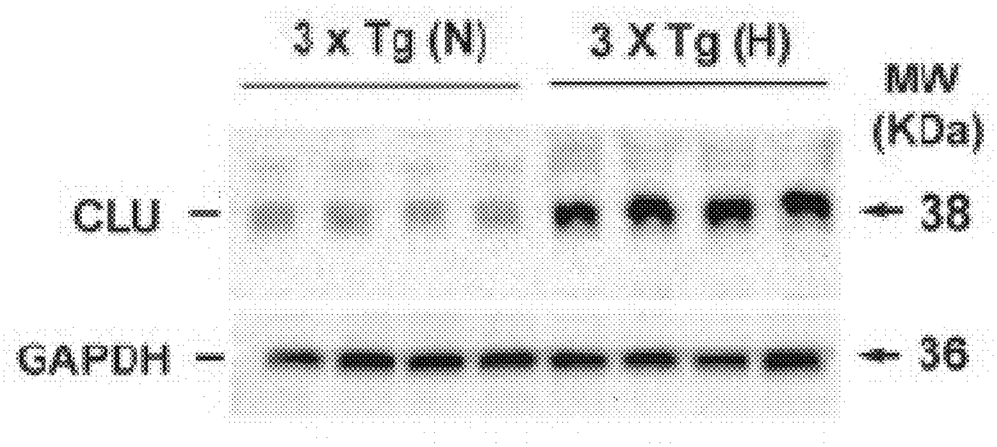
Figure 3E:
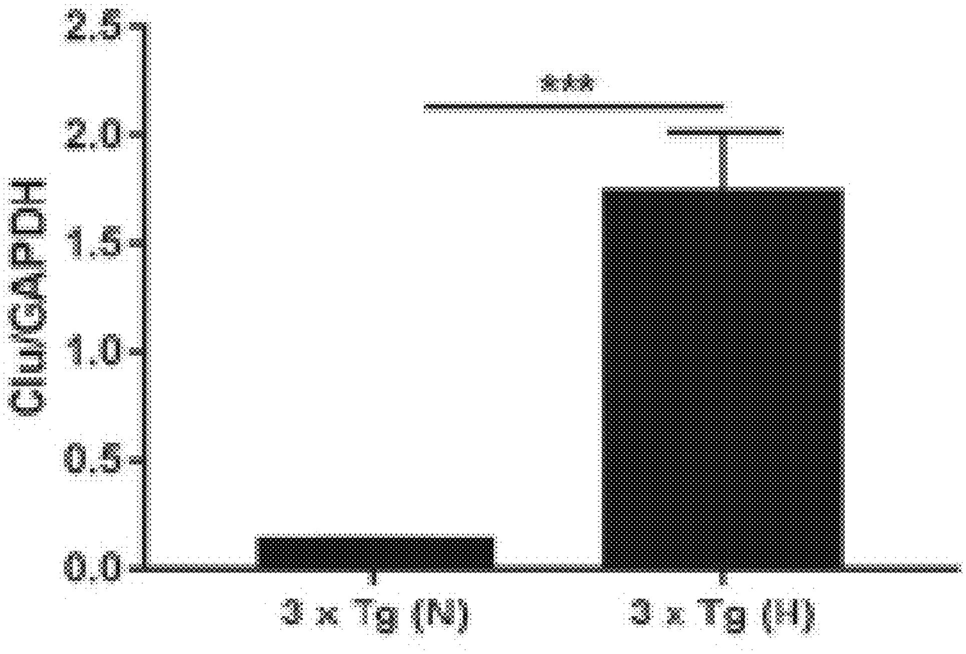
Figure 3F:
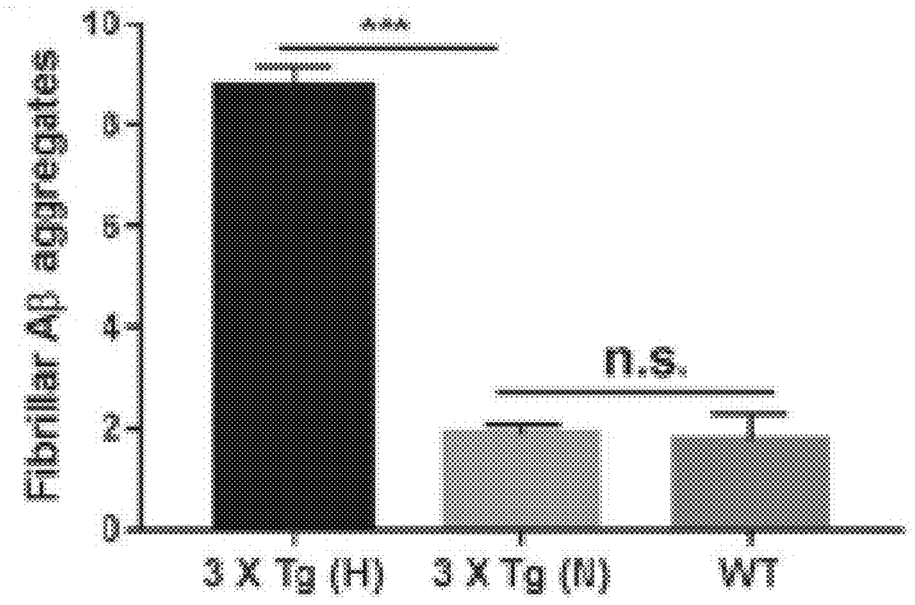
Figure 3G:
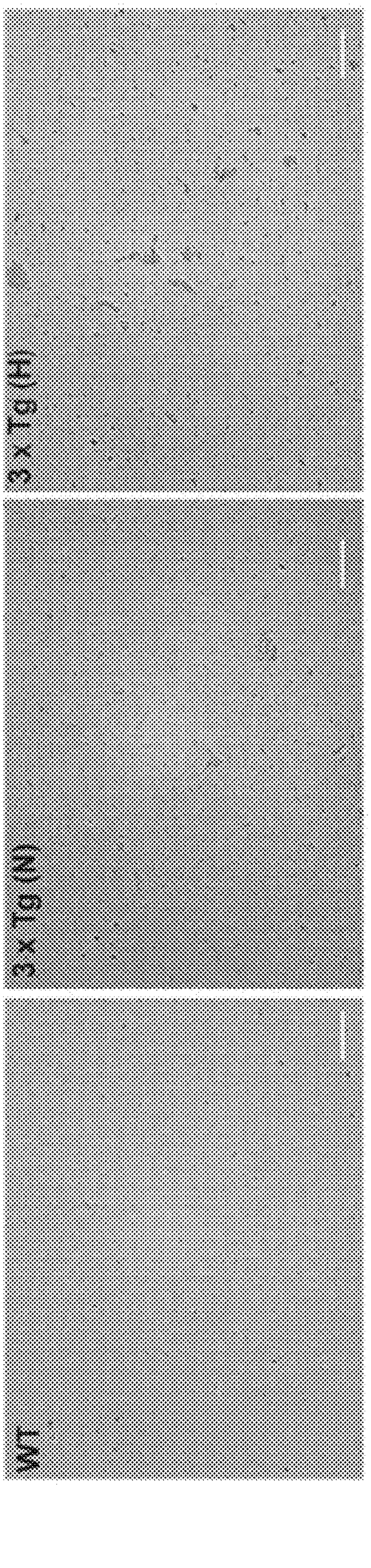
Figure 3H:
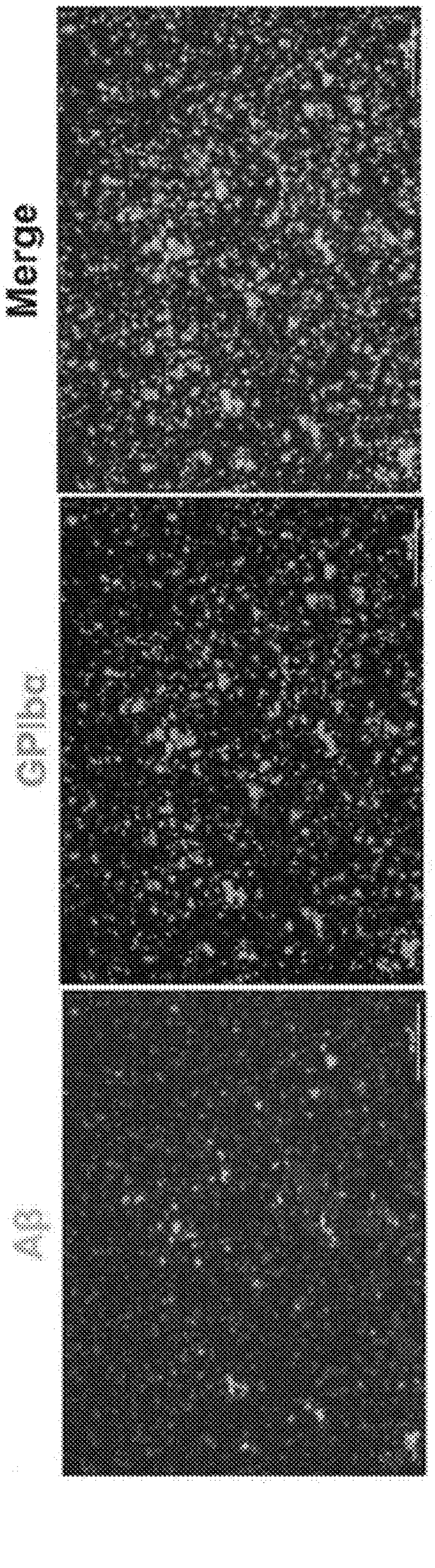

Example 4—Platelets From HFD-Treated 3×Tg Mice Promote Conversion of Soluble Aβ40 Into Fibrillar Aβ Aggregates Associated With Increased Expressions of Integrin αIIbβ$_3$ and Clusterin Integrin αIIbβ3 was used as a classical platelet activation marker. Higher baseline expression levels of integrin αIIbβ3 have been previously detected in AD patients with a more rapid cognitive decline compared to patients with a slower decline (Stellos et al., "Predictive Value of Platelet Activation for the Rate of Cognitive Decline in Alzheimer's Disease Patients," *J. Cereb. Blood Flow Metab.* 30:1817-20 (2010), which is hereby incorporated by reference in its entirety). The results of flow cytometry and Western blotting showed that the expression of integrin αIIb (GPIIb or CD41) and β3 (GPIIIa or CD61) were significantly increased in platelets from HFD-treated 3×Tg mice compared to those in platelets from normal chow-treated 3×Tg mice. However, their expressions showed no significant difference between normal chow-treated 3×Tg mice and B6129S WT control mice (FIGS. 3A-3C, respectively). Clusterin is generated by activated platelets upon binding of Aβ40 to platelet integrin αIIbβ3, and contributes to fibrillar Aβ aggregation in cerebral vessels (Donner et al., "Platelets Contribute to Amyloid-β Aggregation in Cerebral Vessels Through Integrin αIIbβ3-induced Outside-in Signaling and Clusterin Release," *Sci. Signal.* 9:ra52 (2016), which is hereby incorporated by reference in its entirety). Western blotting showed that platelets from HFD-treated 3×Tg mice contained higher levels of clusterin than those from normal chow-treated 3×Tg mice (FIGS. 3D and 3E, respectively). In cultures of platelets from HFD-treated 3×Tg mice, in which αIIbβ3 expression was higher than that of control, the formations of Congo red staining-positive fibrillar Aβ aggregates were apparent after 48 h in culture with Aβ40. In contrast, the formation of Aβ fibrils was barely observed in cultures of mouse platelets from normal chow-treated 3×Tg mice and B6129S WT control mice under the same conditions (FIGS. 3F and 3Q respectively). By immunofluorescence staining, Aβ fibrils (Aβ) were found to adhere to platelets from HFD-treated 3×Tg mice (GPIbα) and formed micro-clots (FIG. 3H), which supports the understanding that soluble Aβ40 is converted into fibrillar Aβ aggregates at the surface of platelet micro-clots.

Figure 4A:
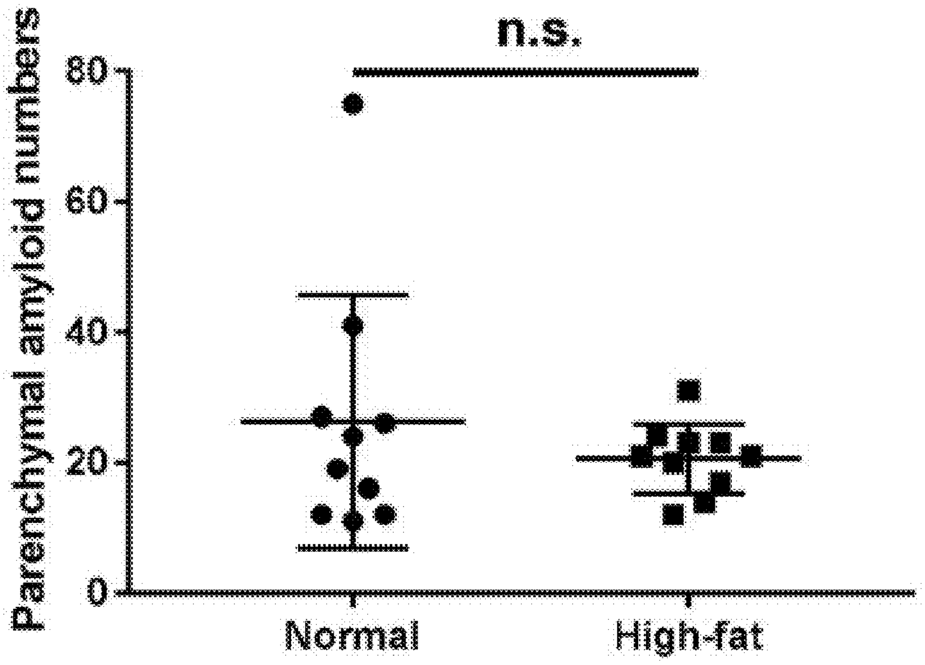
FIGS. 4A-4G show increased CAA burden, formation of platelet-associated fibrillar Aβ aggregates, and oxidative stress in cerebral vessels of HFD-treated 3×Tg mice.
Figure 4B:
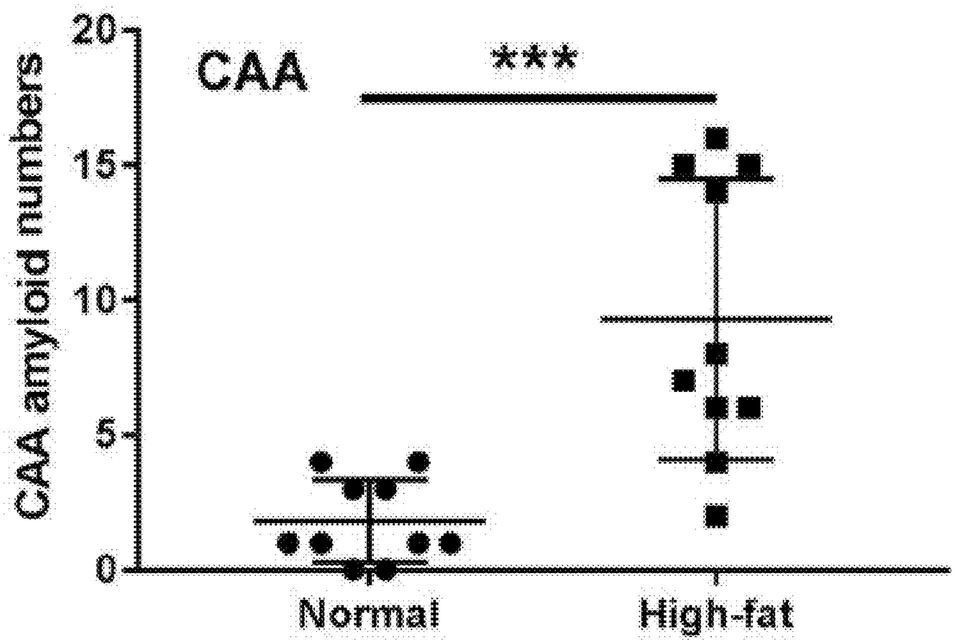
Figure 4C:
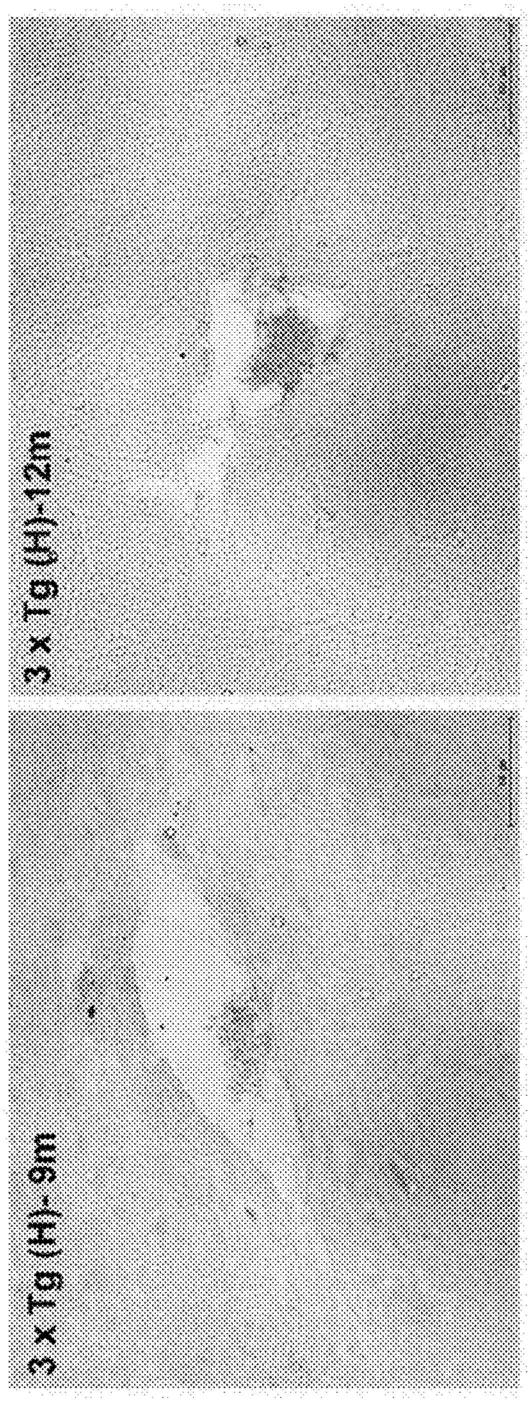

Example 5—Increased CAA Burden, Formation of Platelet-Associated Fibrillar Aβ Aggregates, and Oxidative Stress in Cerebral Vessels of HFD-treated 3×Tg Mice At 6 months of age, mice in the different treatment groups were randomly selected to detect possible initial AD vascular lesions. HFD-treated 3×Tg mice (3 of 3 mice) were found to have the first sign of CAA lesions in their vascular walls. However, CAA lesions were barely detected in normal chow-treated 3×Tg mice (3 of 3 mice) at this age. At 12 months of age, Congo red staining was performed, with separate quantification of vascular and parenchymal amyloid deposits in brain tissue sections. Although parenchymal Aβ numbers were comparable between the two groups (FIG. 4A), HFD-treated 3×Tg mice exhibited a significantly increased CAA burden compared to normal chow-treated 3×Tg mice ($p<0.001$) (FIG. 4B). Found Congo red stain-positive micro-clots were also found in different sized cerebrovascular vessels of HFD-treated 3×Tg mice at 9 months and older (FIG. 4C). These were barely observed in the vascular lumen of normal chow-treated 3×Tg mice, even at 12 months of age.

Figure 4D:
Figure 4E:
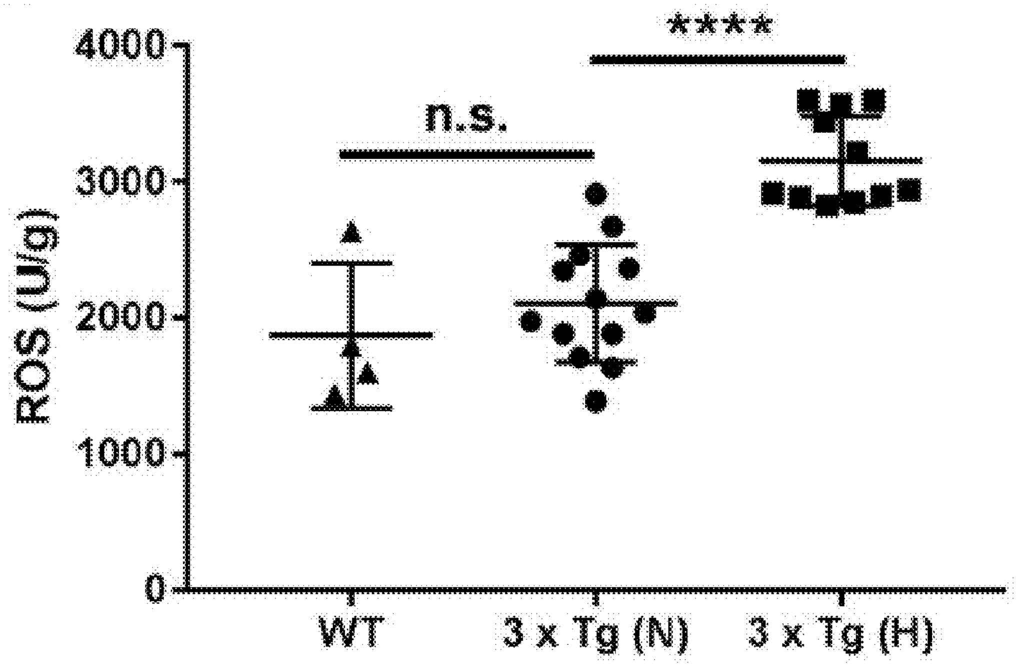
Figure 4F:
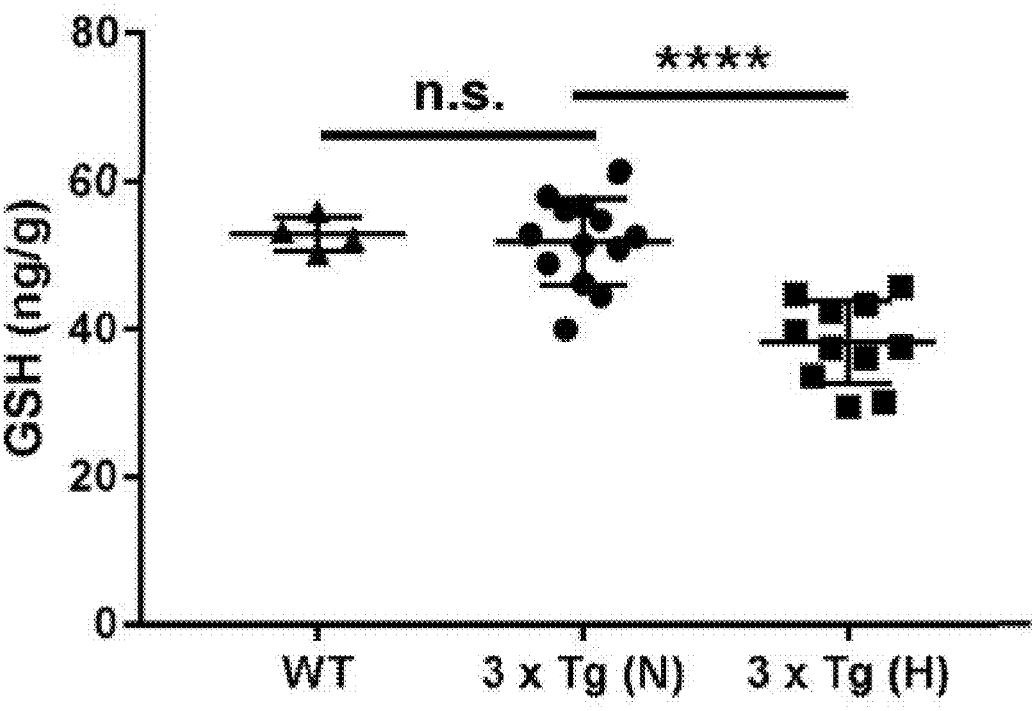
Figure 4G:
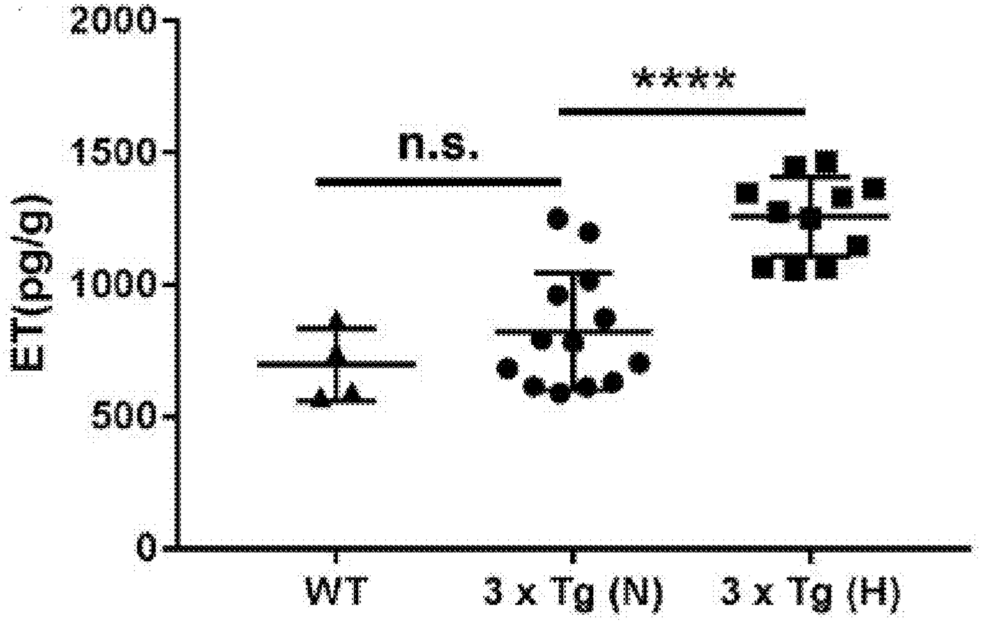

Immunofluorescence analysis showed that in the vascular lumen of 12-month-old HFD-treated 3×Tg mice platelet micro-clots (GPIbα) adhere to vascular Aβ deposits (Aβ) leading to vessel occlusion (FIG. 4D, yellow fluorescence in color version). At 12 months of age, the levels of ROS were significantly increased and GSH were decreased in brain tissues of HFD-treated 3×Tg mice compared to those in normal chow-treated 3×Tg mice ($p<0.001$) (FIGS. 4E and 4F, respectively). Given that endostatin is secreted by pericytes upon ROS stimulation resulting in the contraction of cerebral capillaries (Mufson et al., "Molecular and Cellular Pathophysiology of Preclinical Alzheimer's Disease," *Behav Brain Res.* 311:54-69 (2016), which is hereby incorporated by reference in its entirety), its levels were then examined in brain tissue of different treatment groups. The results showed that the levels of endostatin were significantly increased in brain tissues of HFD-treated 3×Tg mice compared to those in normal chow-treated 3×Tg mice ($p<0.001$) (FIG. 4G). The levels of ROS, GSH, and ET showed no significant differences between normal chow-treated 3×Tg mice and B6129S WT control mice at the age of 12 months of old (FIGS. 4E-4G).

Figure 5A:
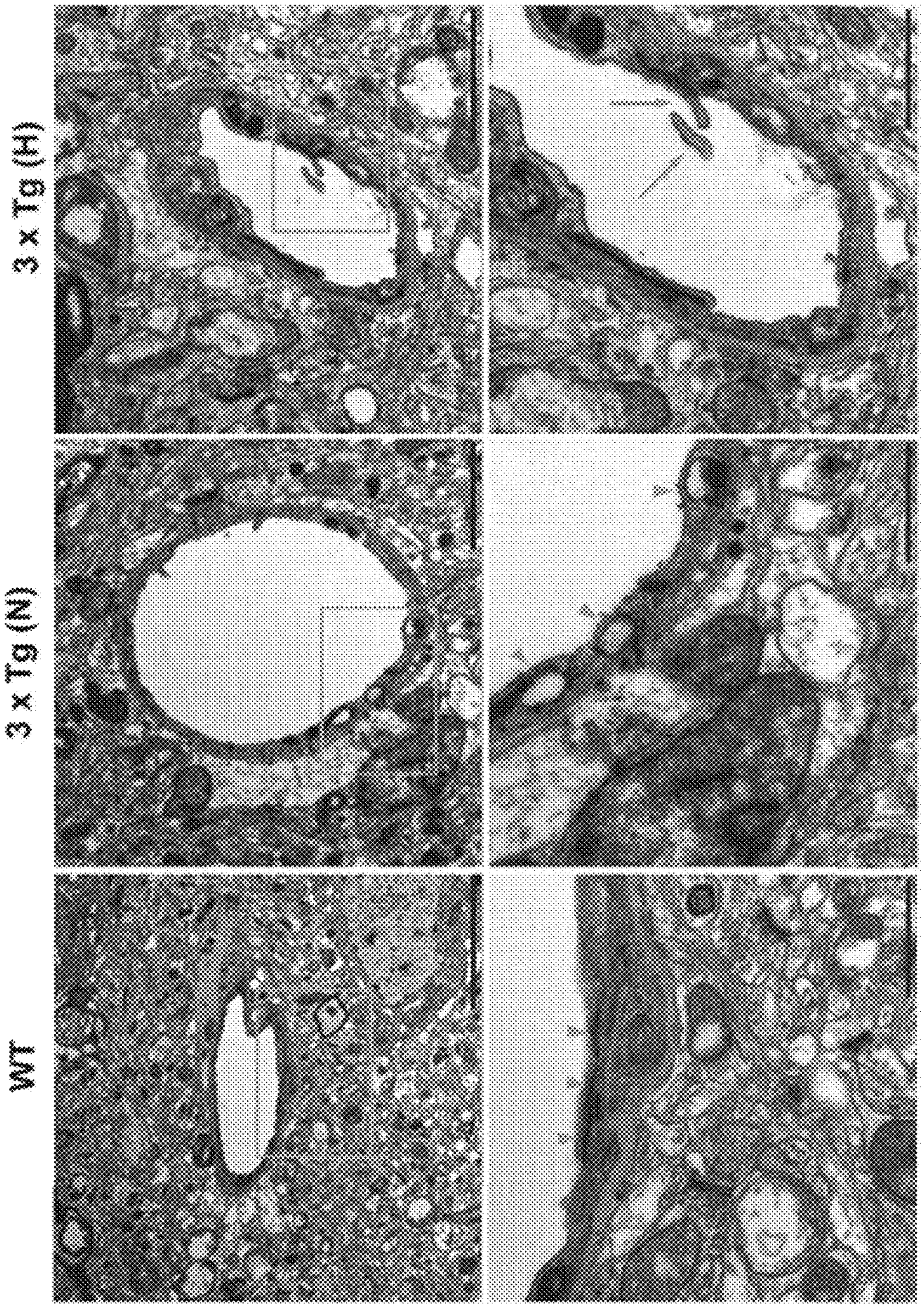
FIGS. 5A-C show disrupted blood-brain barrier in HFD-treated 3×Tg mice.
Figure 5B:
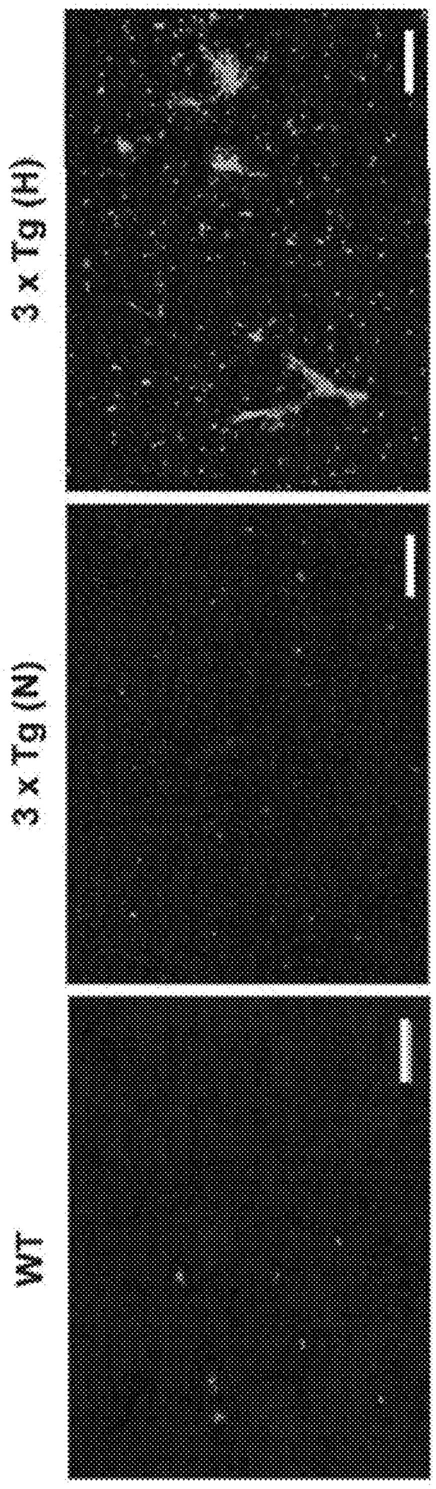
Figure 5C:
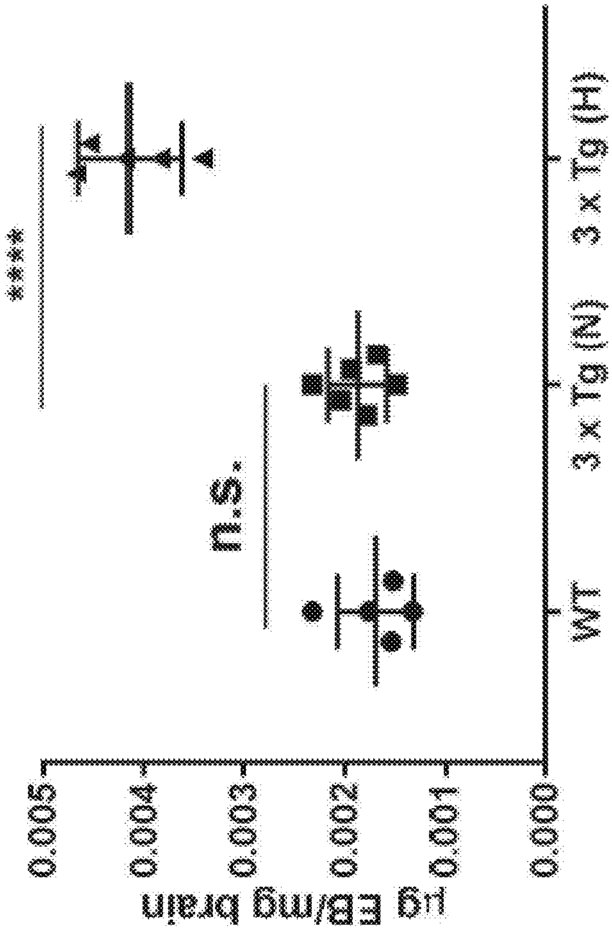
Figure 6A:
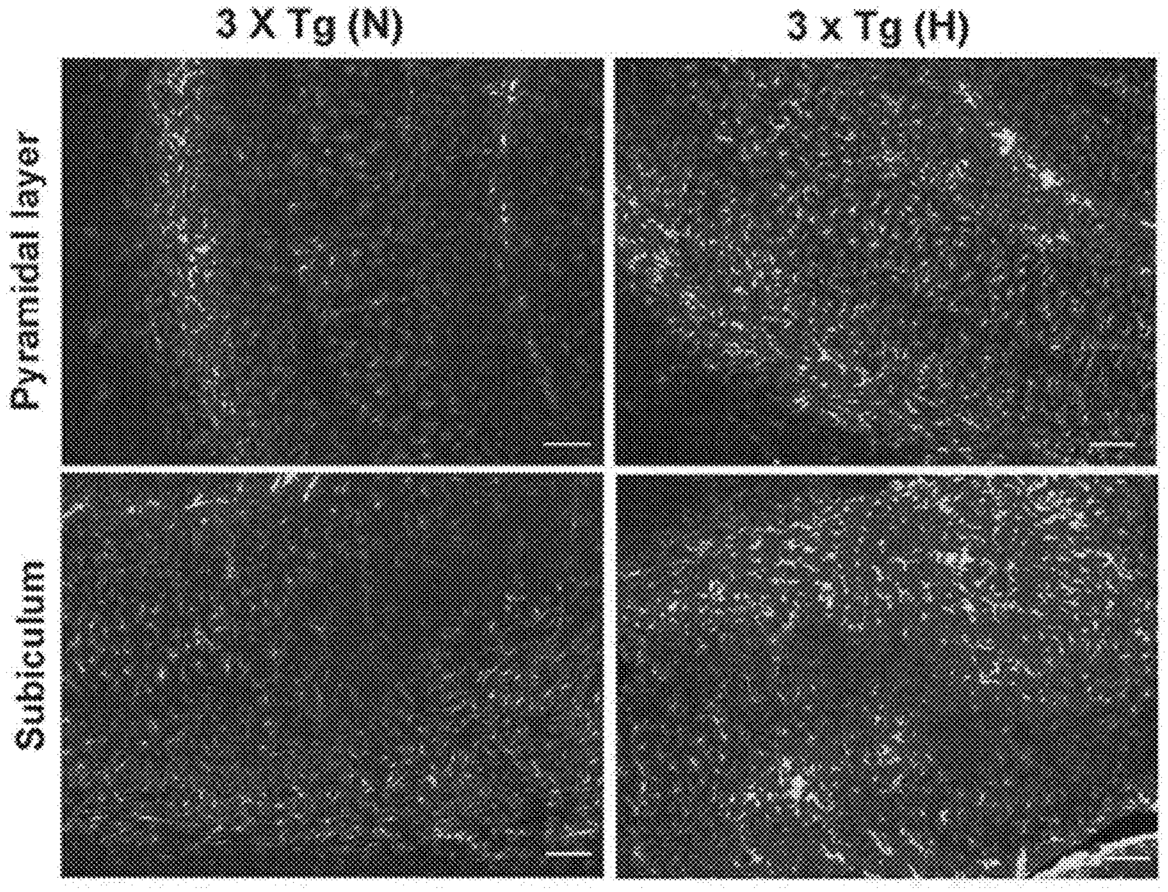
FIGS. 6A-6C show increased neuroinflammation in HFD-treated 3×Tg mice.
Figure 6B:
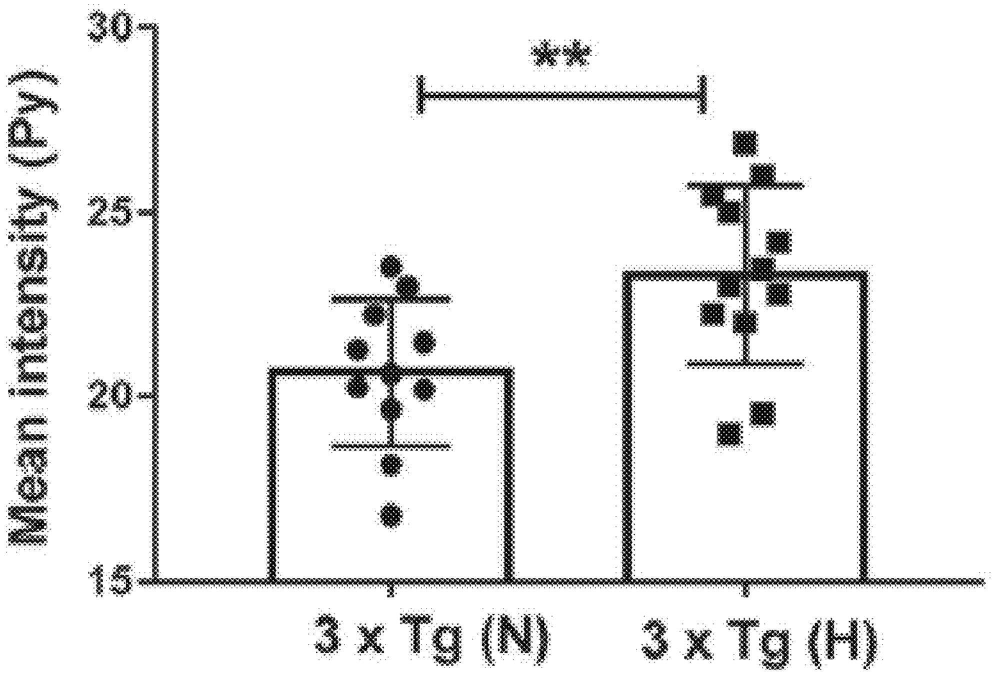
Figure 6C:
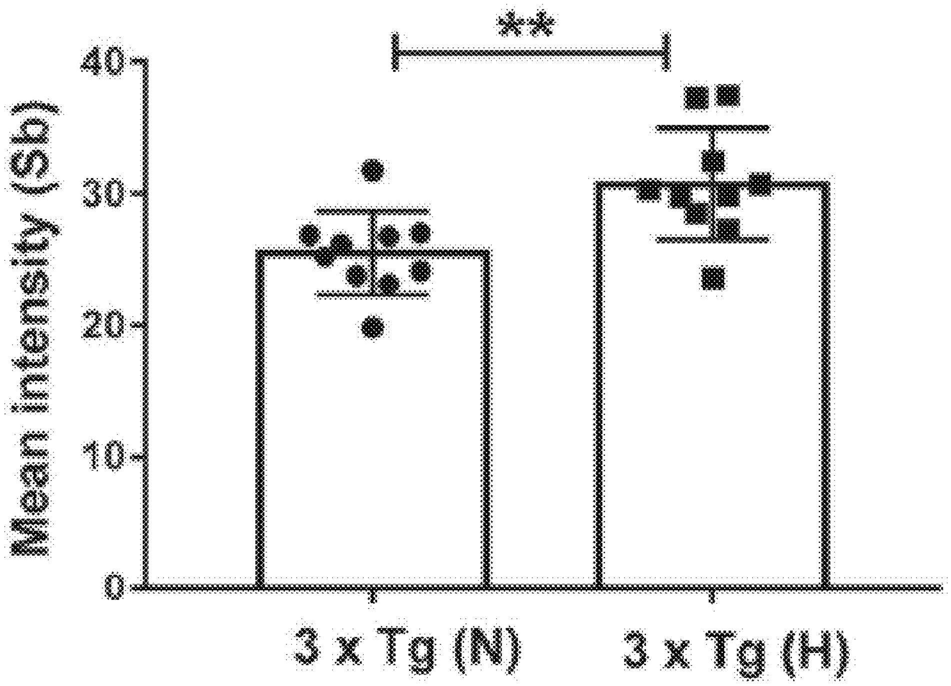

Example 6—Disrupted Blood-Brain Barrier and Aggravated Neuroinflammation in HFD-Treated 3×Tg Mice Tight junctions form the basis of the blood-brain barrier (BBB). In B6129S WT mice and normal chow-treated 3×Tg mice, tight junctions appeared continuous and lay flat, preventing diffusion of blood components into the brain. However, the tight junctions in brain sections from HFD-treated 3×Tg mice appeared to be breaking off into the capillary lumen, providing an opportunity for BBB leakage (FIG. 5A). Given these structural alterations, changes in cerebral vascular permeability were assessed by Evans blue dye extravasation as described in the methods. Under excitation of 550 nm, there was a marked increase in red fluorescence in the cortex of HFD-treated 3×Tg mice compared to normal chow-treated 3×Tg mice and B6129S WT control mice (FIG. 5B). The content of Evans blue extravasated per mg tissue also showed significantly increased in the brain tissues of HFD-treated 3×Tg mice (FIG. 5C), indicating that BBB integrity in HFD-treated 3×Tg mice was compromised. There were no significant differences in vascular permeability between normal chow-treated 3×Tg mice and B6129S WT control mice. Given the increased vascular permeability in HFD-treated 3×Tg mice, neuroinflammation was then examined in these mice. GFAP (+) cells were significantly increased in pyramidal layer (py) and subiculum of HFD-treated 3×Tg mice (FIGS. 6A and 6B, respectively), indicating an increased neuroinflammatory response.

Figure 7A:
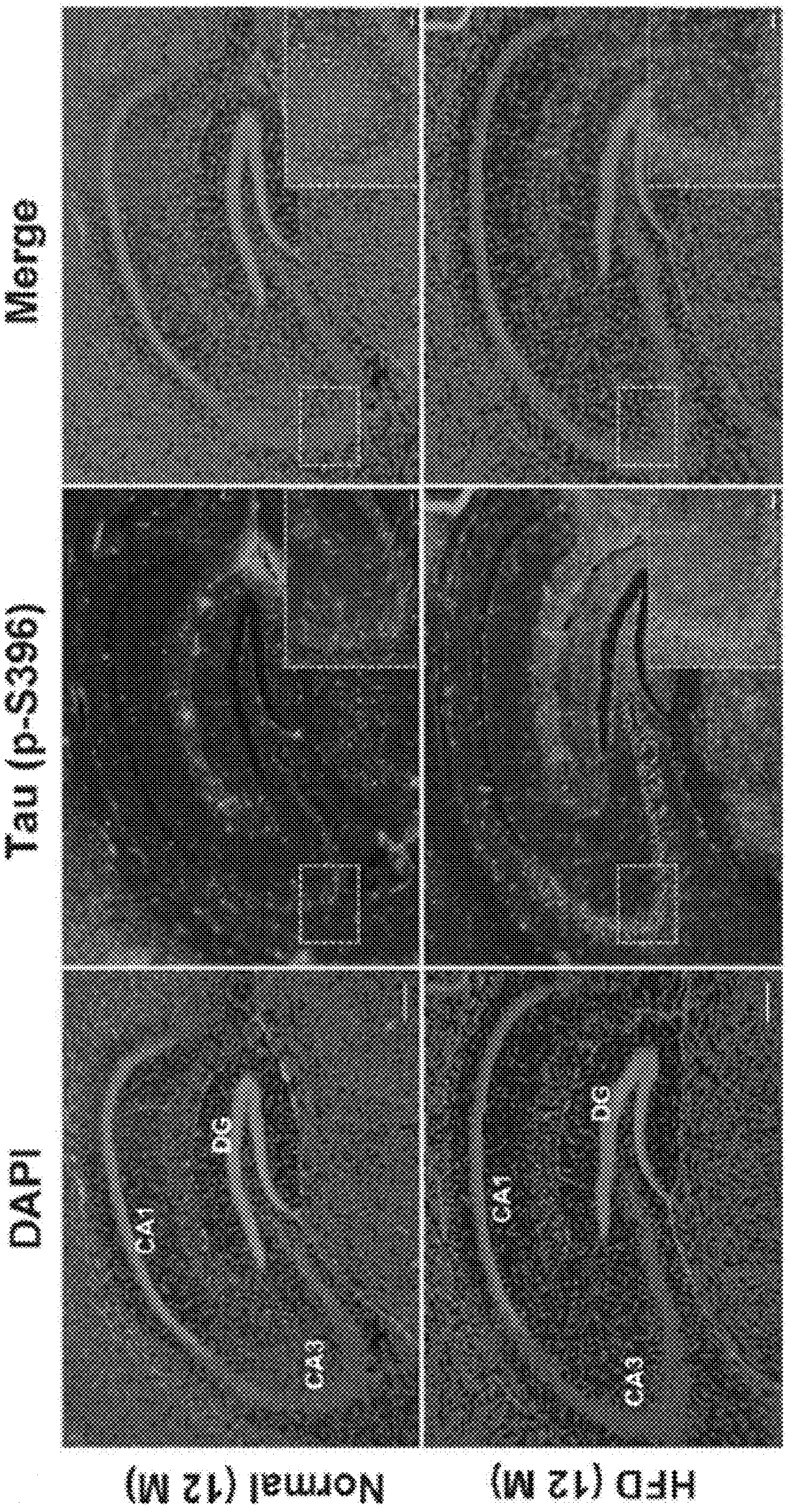
FIGS. 7A-7C show increased tau pathology in HFD-treated 3×Tg mice.
Figure 7B:
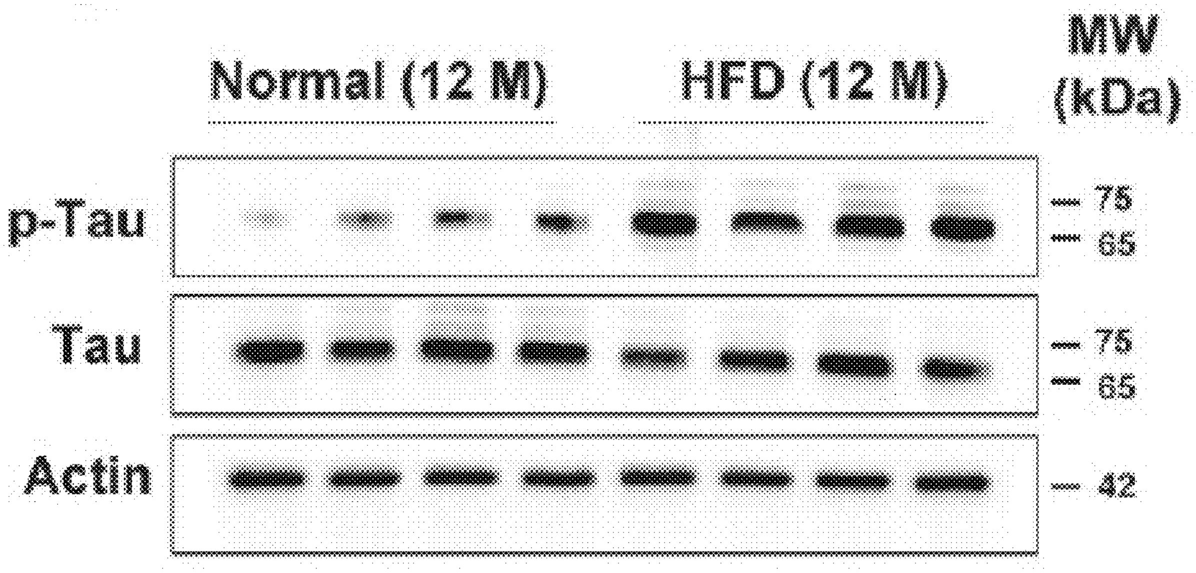
Figure 7C:
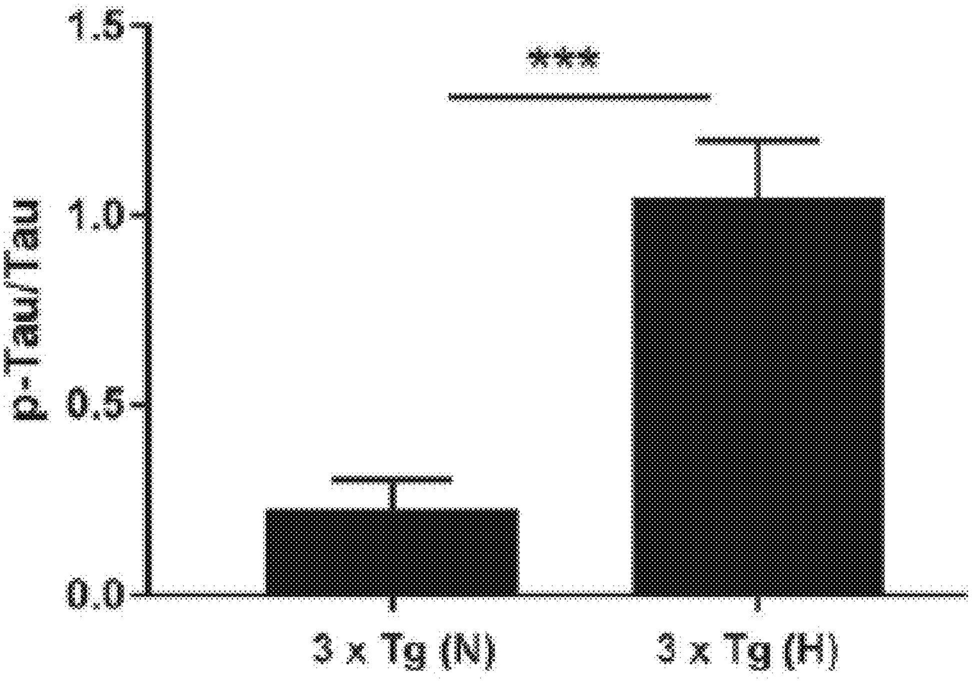
Figure 8A:
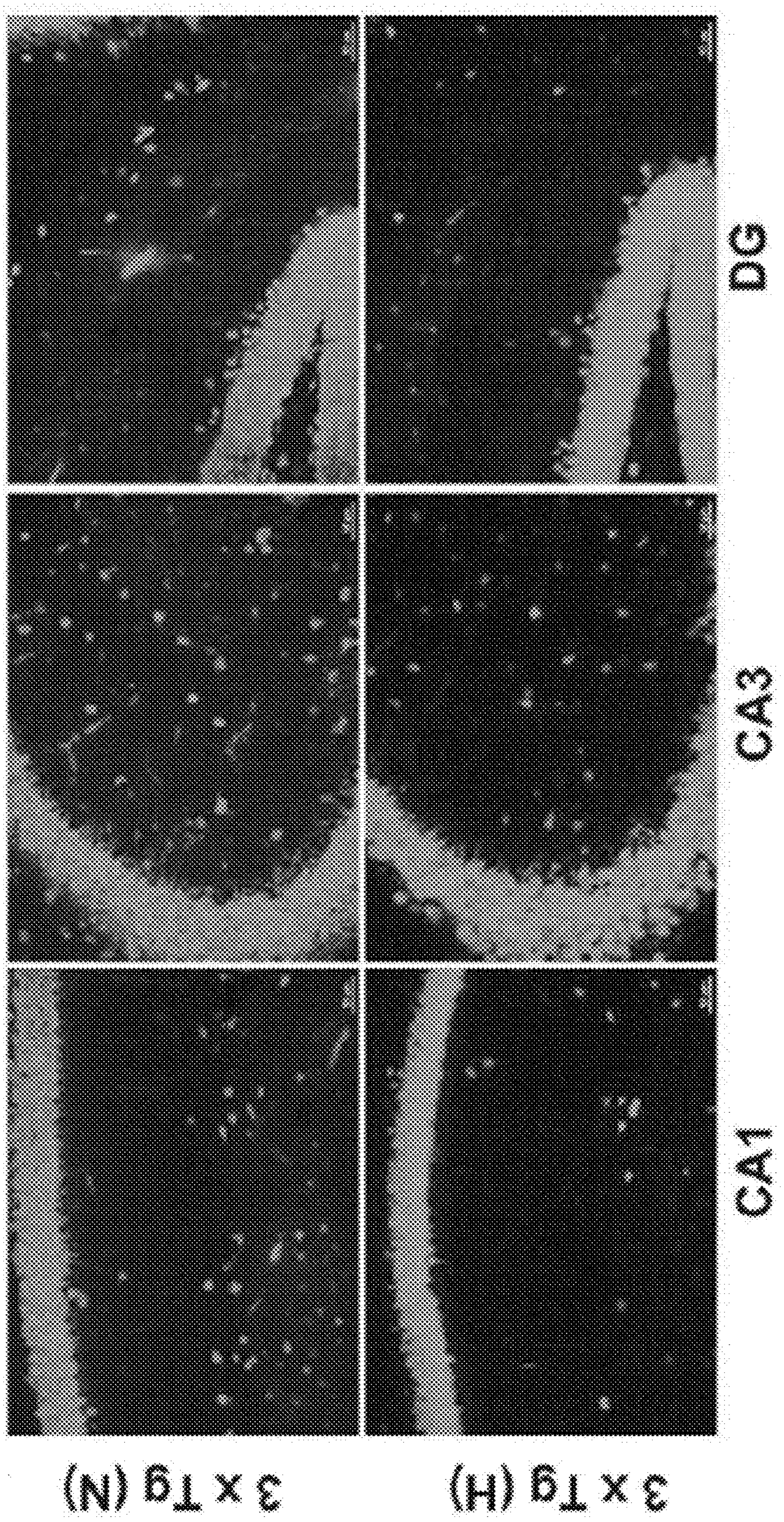
FIGS. 8A-8B show increased loss of neurons in the hippocampus of HFD-treated 3×Tg mice.
Figure 8B:
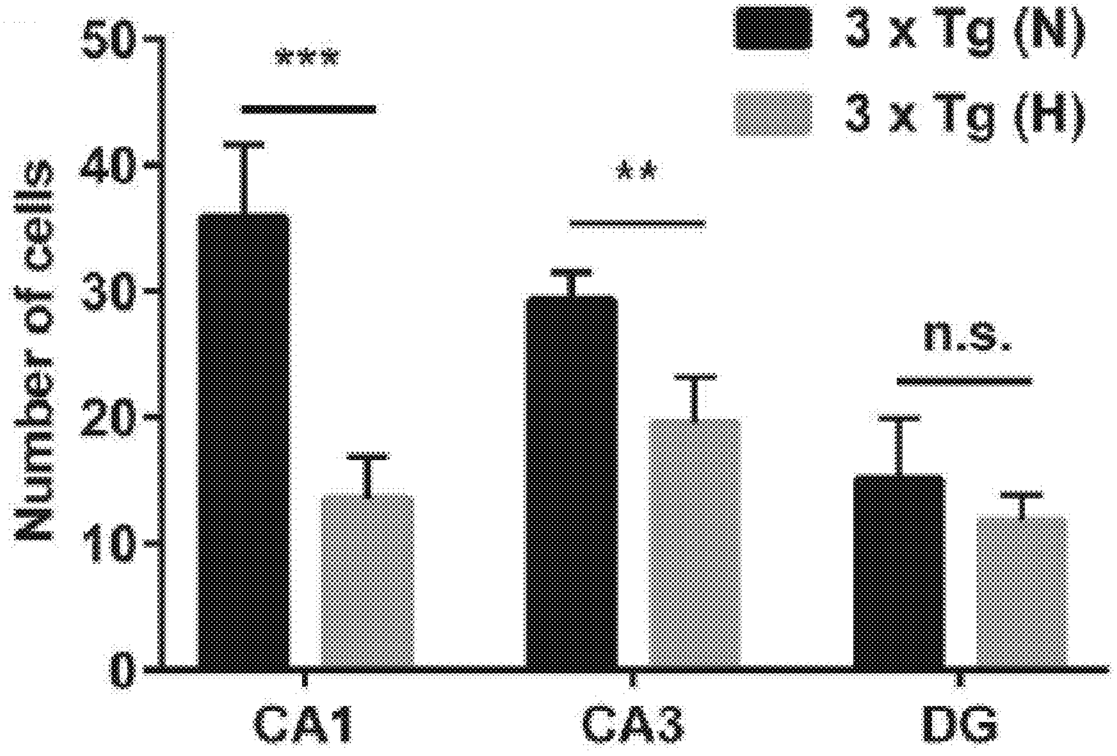

Example 7—Increased Tau Pathology and Loss of Neurons in HFD-treated 3×Tg Mice Given that CAA, oxidative stress, and inflammation have been proposed as additive variables contributing to promoting NFT pathology (Mufson et al., "Molecular and Cellular Pathophysiology of Preclinical Alzheimer's Disease," *Behav Brain Res.* 311:54-69 (2016), which is hereby incorporated by reference in its entirety), tau pathology was examined in HFD-treated 3×Tg mice. Tau pathology typical starts at ~12 months of age in 3×Tg mice (Drummond et al., "Alzheimer's Disease: Experimental Models end Reality," *Acta. Neuropathol.* 133:155-75 (2017), which is hereby incorporated by reference in its entirety). Normal chow-treated 3×Tg mice at the end of the experiment (12 months of age) have limited tau hyperphosphorylation in different hippocampal subregions (FIG. 7A). However, HFD-treated 3×Tg mice have much more extensive tau hyperphosphorylation in hippocampal regions at 12 months of age. Western blotting confirmed that the levels of p-Tau were significantly higher in HFD-treated 3×Tg mice than in the brain of normal chow-treated 3×Tg mice (FIGS. 7B and 7C, respectively). Given the compromised vascular system in HFD-treated 3×Tg mice, hippocampal sub-regions were also examined for evidence of increased neuronal death related to hypoperfusion. NeuN immunohistochemical staining showed that the neuron numbers in the hippocampal CA1 (more prone to cell loss with hypoxia) and CA3 regions were significantly decreased in 12-month-old HFD-treated 3×Tg mice compared to those in normal chow-treated 3×Tg mice ($p<0.01$) (FIGS. 8A and 8B).

Figure 9A:
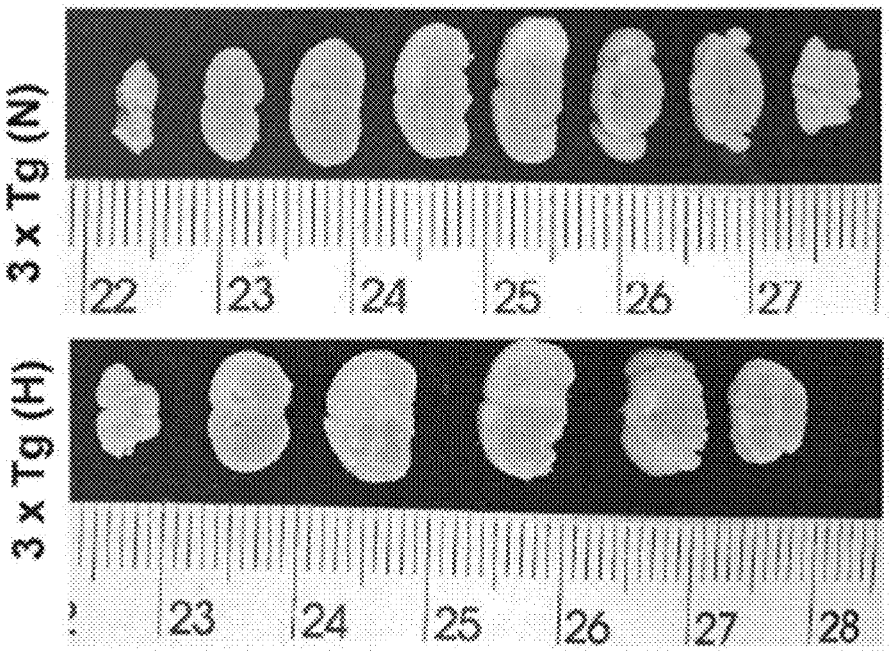
FIGS. 9A-9D show increased ischemic-related tau hyperphosphorylation in HFD-treated 3×Tg mice.
Figure 9B:
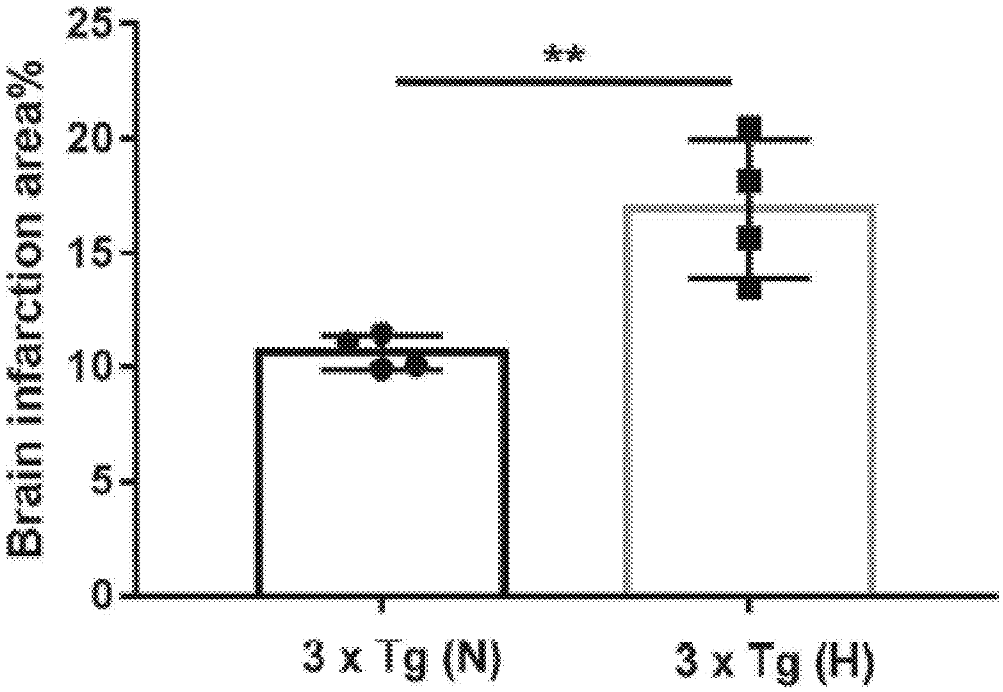
Figure 9C:
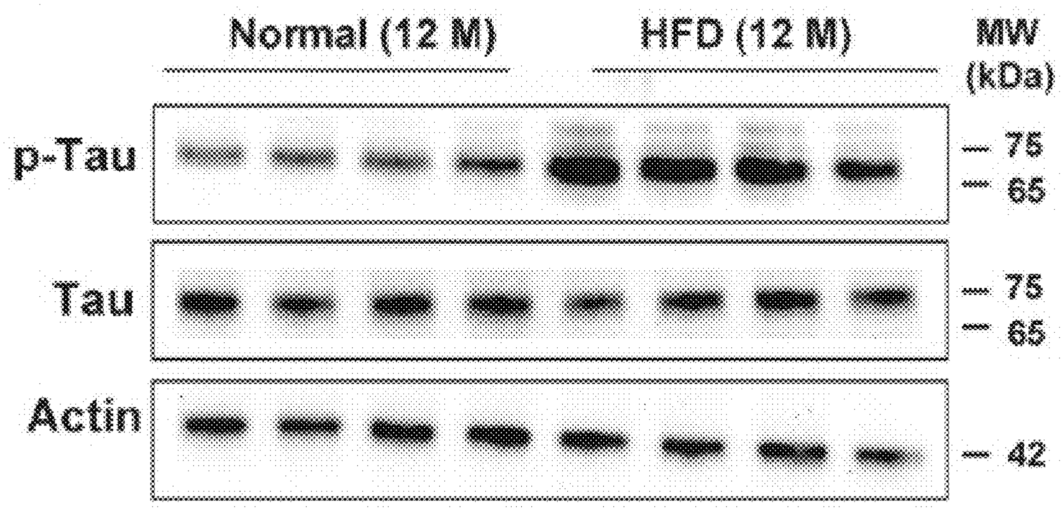
Figure 9D:
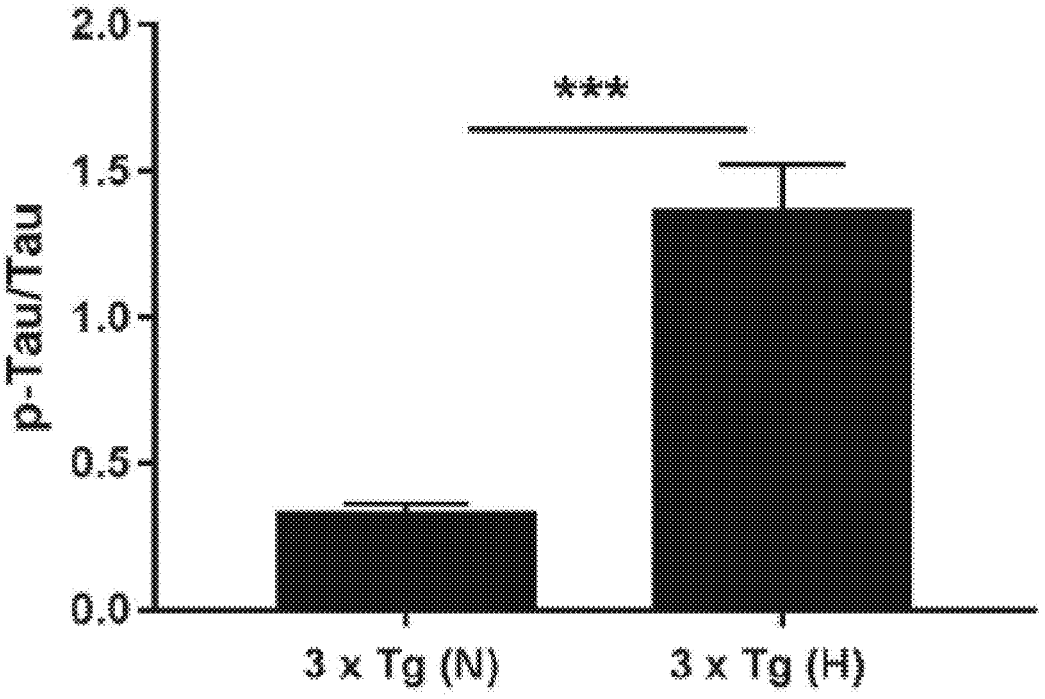

Example 8—Increased Ischemic-Related Tau Hyperphosphorylation in HFD-Treated 3×Tg Mice It was also investigated whether HFD treatment promotes ischemia-related tau hyperphosphorylation in 3×Tg mice. In the tMCAO model, the mean brain infarction area was significantly larger in HFD-treated 3×Tg mice compared to the normal chow-treated cohorts (FIGS. 9A and 9B, $p<0.01$). Western blotting showed that the levels of p-Tau were significantly higher in HFD-treated 3×Tg mice than in normal chow-treated 3×Tg mice when these mice underwent the challenge of acute ischemic stroke (FIGS. 9C and 9D, *$p<0.001$).

Example 9—The Effect of A11 on AD Pathology

Figure 10A:
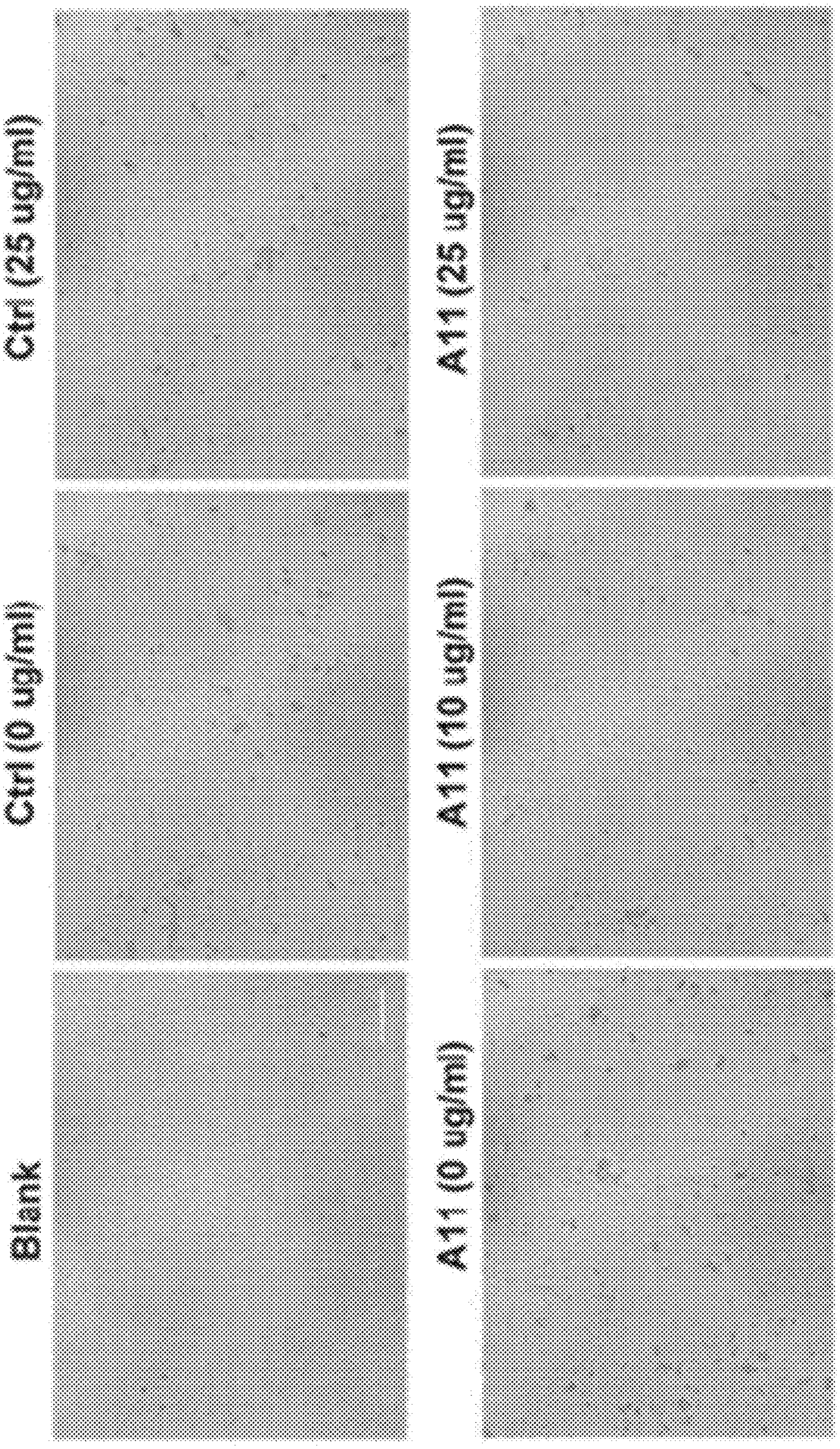
FIGS. 10A-10K show the effect of humanized anti-GPIIIa49-66 scFv Ab (A11) on AD pathology.
Figure 10B:
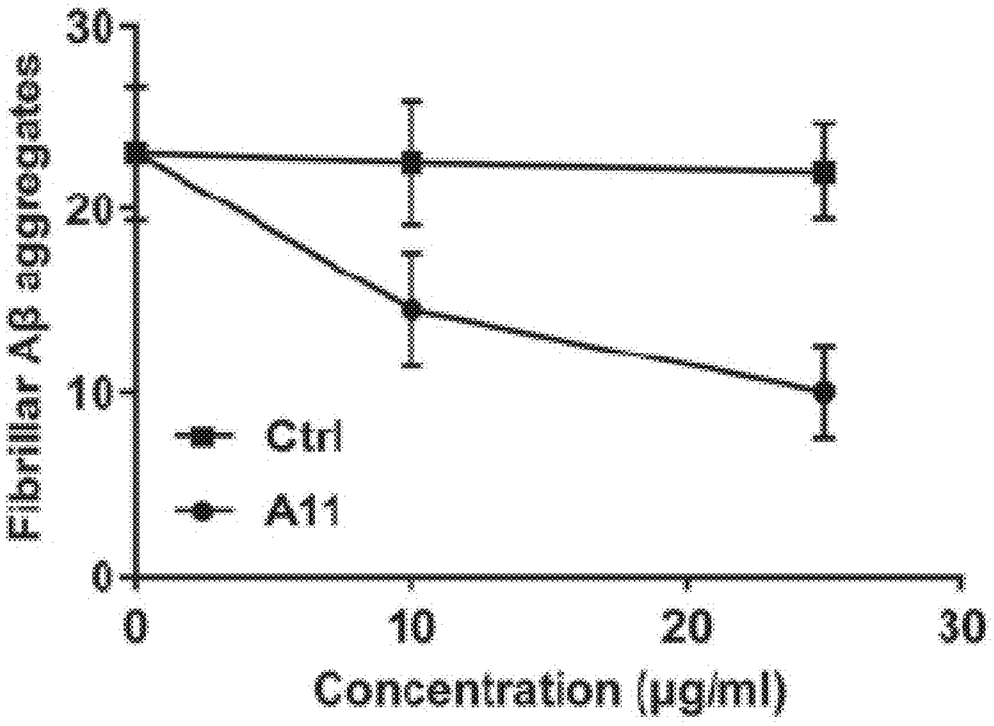
Figure 10C:
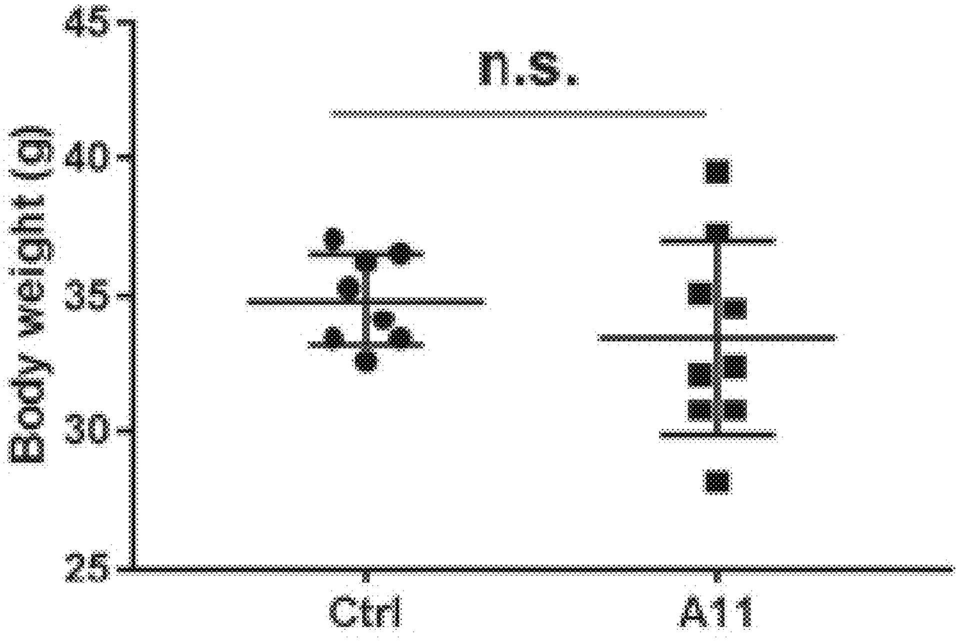
Figure 10D:
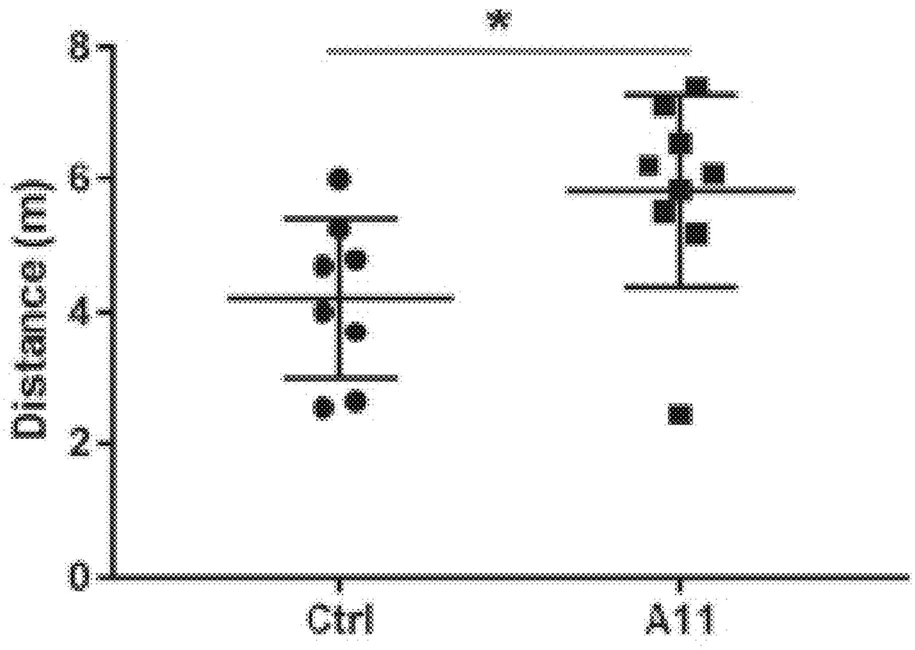
Figure 10E:
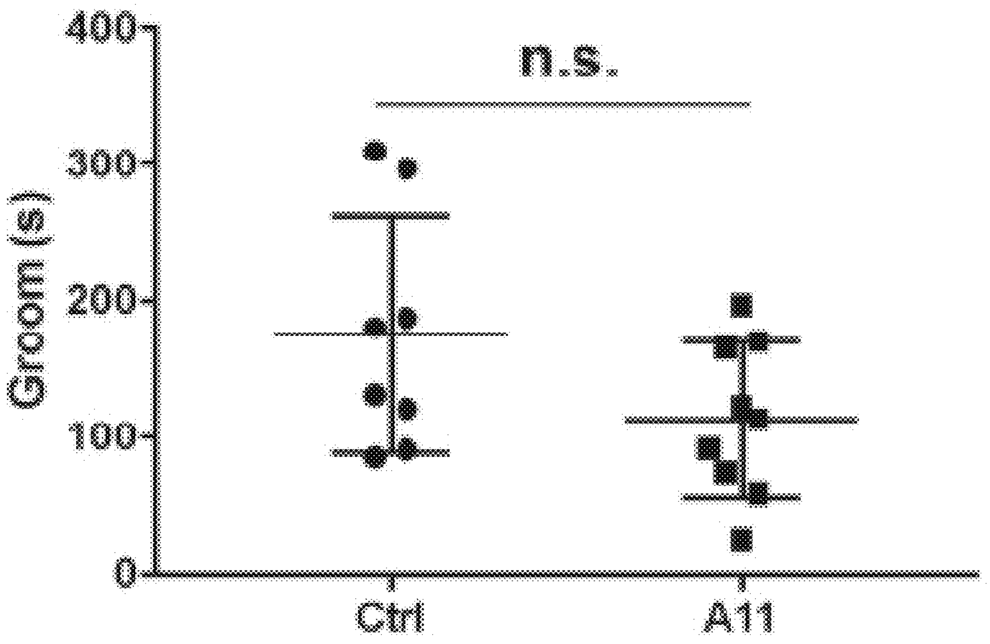
Figure 10F:
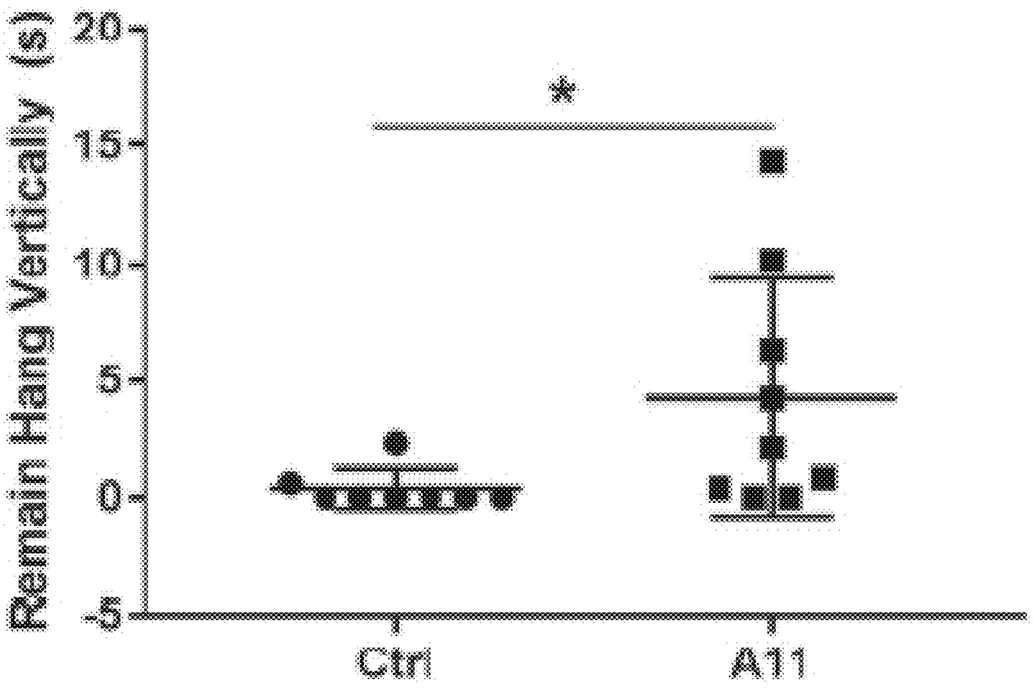
Figure 10G:
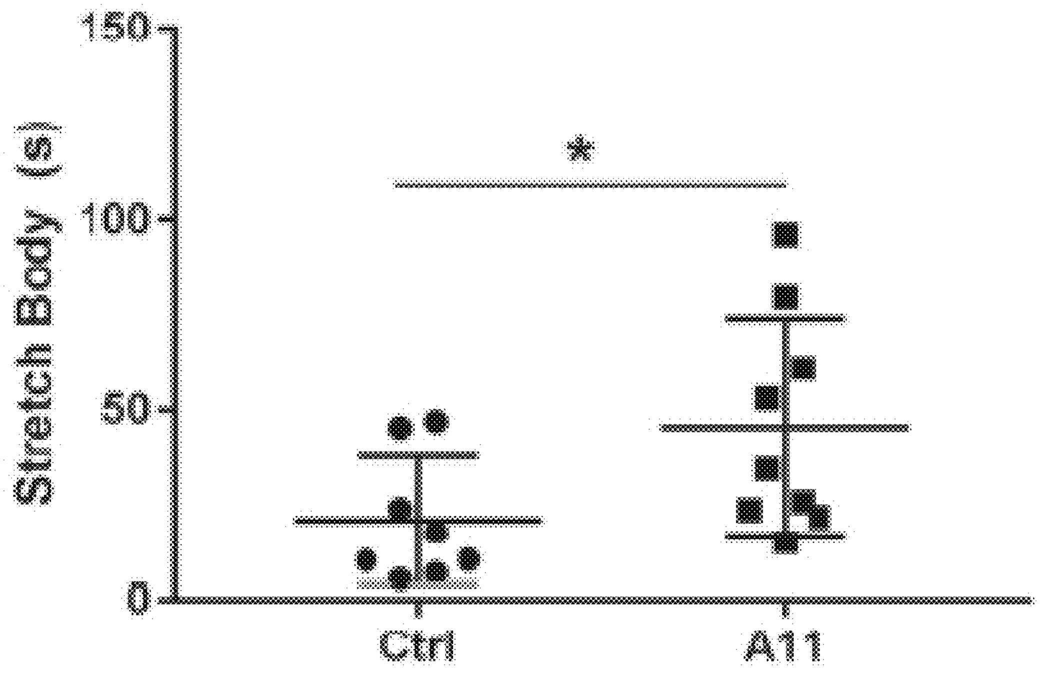
Figure 10H:
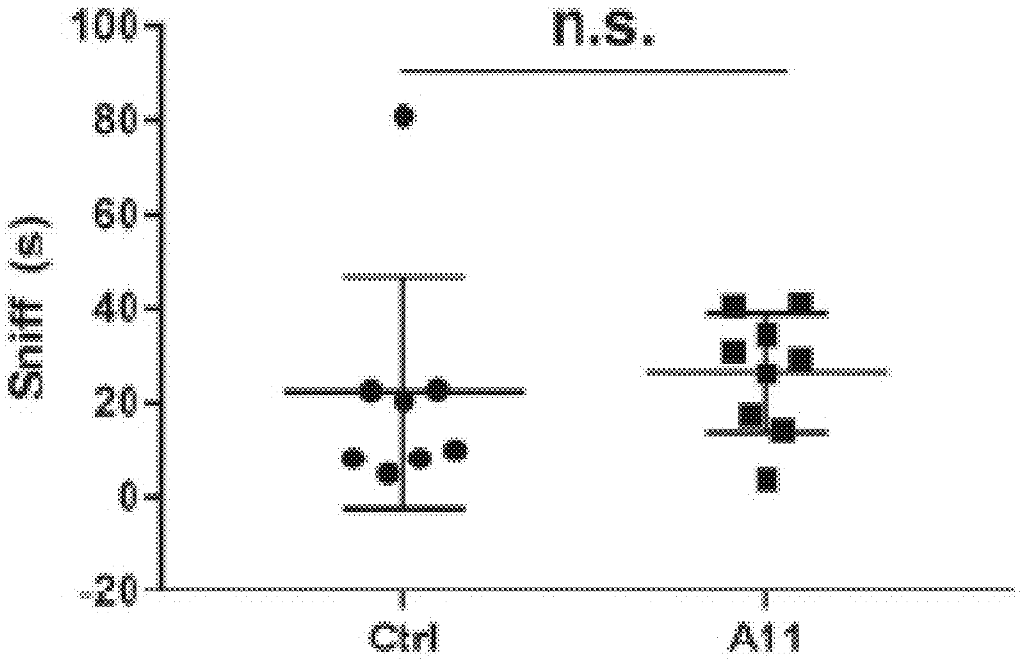
Figure 10I:
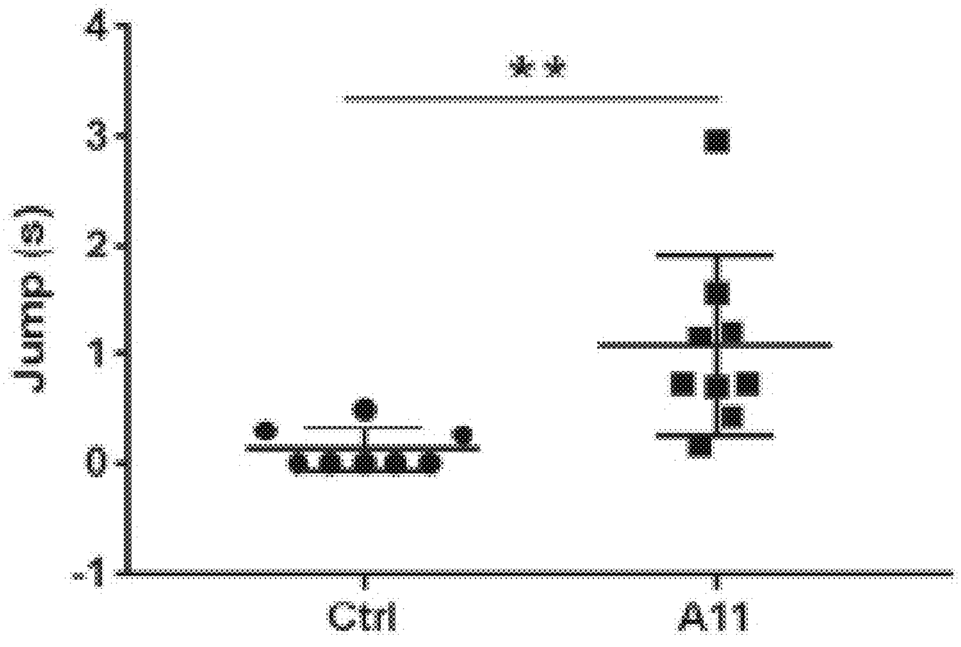
Figure 10J:
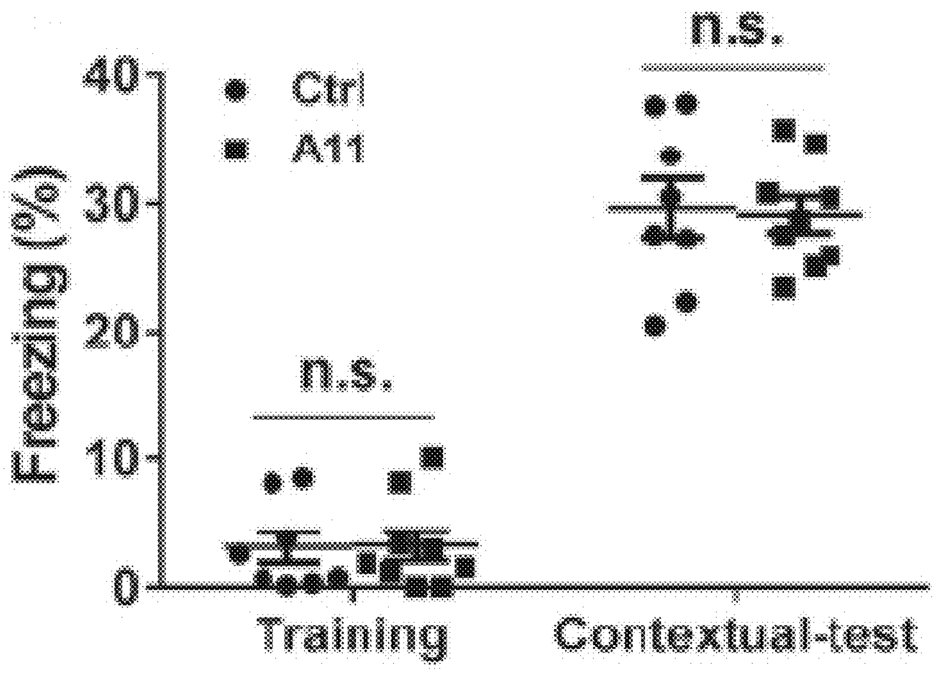
Figure 10K:
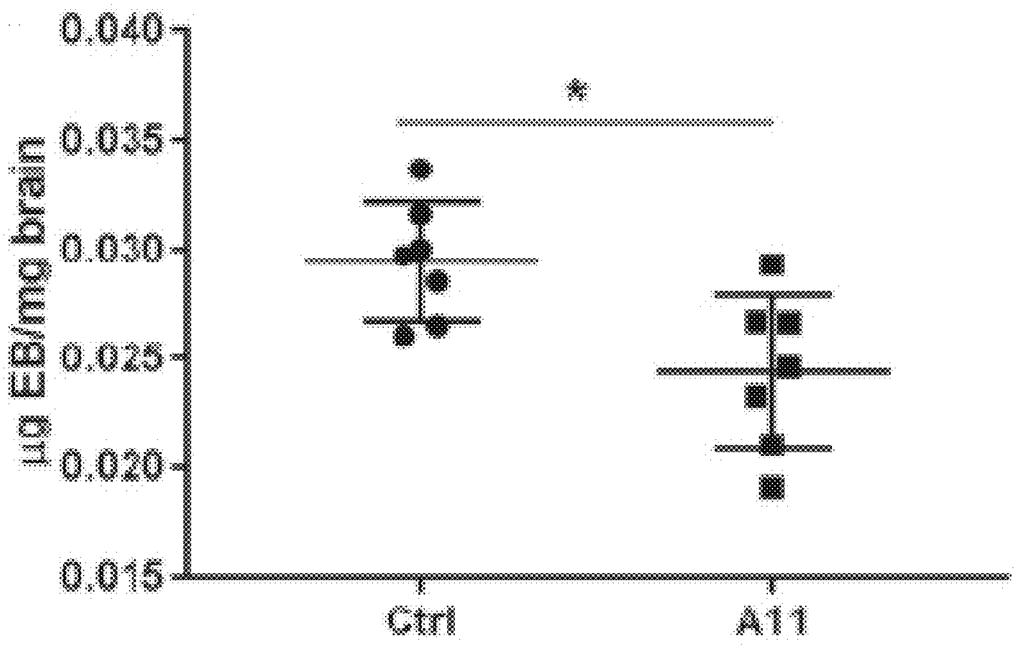

A1 is a humanized scFv Ab that preferentially binds to activated platelets and can lyse platelet thrombi (Zhang et al., "Dissolution of Arterial Platelet Thrombi In Vivo With a Bifunctional Platelet GPIIIa49-66 Ligand Which Specifically Targets the Platelet Thrombus," *Blood* 116:2336-44 (2010), which is hereby incorporated by reference in its entirety). In vitro, A11 dose-dependently inhibited fibrillar Aβ aggregate formation in the cultures of platelets from HFD-treated 3×Tg mice in culture with A1340 compared to irrelevant control scFv Ab (FIGS. 10A and 10B). In vivo, 6-month-old HFD-treated 3×Tg mice were treated by A11 or control scFv Ab two times every week for 3 months. There was no significant difference in body weight between the two groups at the end of A11 treatment (FIG. 10C). Behavior testing showed that travel distance (FIG. 10D), remaining hung vertically (FIG. 10F), body stretch (FIG. 10G) and jumping (FIG. 10I) were significantly improved in A11-treated mice compared to control Ab-treated cohorts; however, there were no significant differences in grooming (FIG. 10E) and sniff testing (FIG. 10H) between the two groups. Contextual fear memory was also not improved by A11 treatment (FIG. 10J). Although tau related pathology is limited at this age, A11 treatment did improve vascular permeability (FIG. 10K). A11-treated mice had no noticeable changes in fur, body weight, appetite, spontaneous bleeding, or life span. No significant pathological changes were observed in the brain, heart, liver, kidney, or lung by histologic examination, indicating that the treatment was apparently harmless to the mice.

Figure 11:
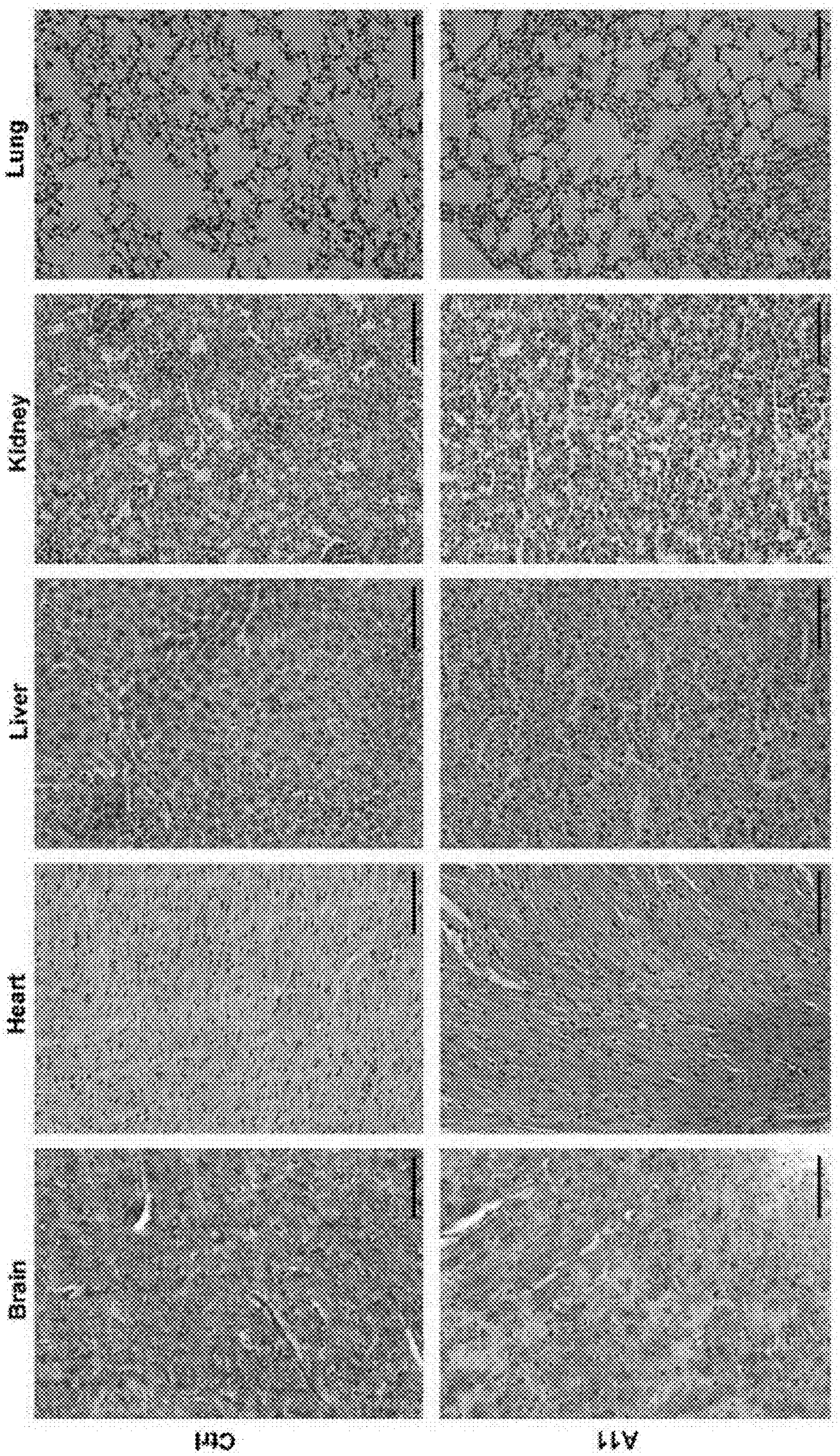
FIG. 11 compares histological stain representations of the brain, heart, liver, kidney, and lung in control subjects and A11-treated subjects.

The safety of A11 injection on other organs was assessed by histological examination of all major organs in the mice treated with A11. No significant pathological changes were observed in the brain, heart, liver, kidney, or lung by histologic examination, suggesting that the treatment was apparently harmless to mice (FIG. 11).

Discussion of Examples 1-9

Understanding how co-concurrent disease states contribute to AD is important for early diagnosis and the development of therapies for AD patients. In the preceding Examples, 3×Tg mice were fed with HFD and demonstrated that HFD is capable of eliciting the formation of platelet-associated fibrillar Aβ aggregates, increased CAA burden, tau pathology and loss of neurons. The ideal study design should include both 3×Tg mice on normal chow and 3×Tg mice on HFD, alongside WT mice on normal chow and WT mice on HFD, to allow for a more full understanding of what changes are due to the interaction of 3×Tg and HFD. In the preceding Examples, a group of WT mice on HFD were not included since many of the platelet measures in these mice on HFD have been well documented. It was previously shown that platelets from HFD-treated C57BL6/N mice were larger, hyperactive and presented oxidative stress when compared to control C57BL6/N mice on a standard laboratory diet, possibly due to alterations in platelet generation or higher platelet turnover (Gaspar et al., "Maternal and Offspring High-fat Diet Leads to Platelet Hyperactivation in Male Mice Offspring," *Sci. Rep.* 11:1473 (2021), which is hereby incorporated by reference in its entirety). HFD in B6SJL mice was found to amplify surface P-selectin expression on platelets and increase aggregation of platelets induced by thrombin (Kumar et al., "P66Shc Mediates Increased Platelet Activation and Aggregation in Hypercholesterolemia," *Biochem. Biophys. Res. Commun.* 449:496-501 (2014), which is hereby incorporated by reference in its entirety). Nagy et al. ("Contribution of the P2Y12 Receptor-mediated Pathway to Platelet Hyperreactivity in Hypercholesterolemia," *J. Thromb. Haemost.* 9:810-9 (2011), which is hereby incorporated by reference in its entirety) reported that platelets are hyper-reactive in HFD-treated C57BL6 mice, which was partially due to the activation of the adenosine diphosphate (ADP) receptor P2Y12-mediated pathway. Similarly, the data demonstrated that that platelets from HFD-treated 3×Tg mice were increased in size and number, and had elevated glycoprotein αIIbβ3 expression. Those data indicate that HFD induces platelet hyperactivity in different mouse strains, contributing to hypercoagulability. Given that HFD-treated WT mice do not develop Aβ plaques or tau pathology, HFD-treated 3×Tg mice are more appropriate to study the contributions of vascular factors to AD related pathology.

Extensive data indicates that vascular factors play an important role in the pathogenesis of AD. The AD brain has altered blood flow (Farkas et al., "Cerebral Microvascular Pathology in Aging and Alzheimer's Disease," *Prog. Neurobiol.* 64:575-611 (2001); Greenberg, "Amyloid Angiopathy-Related Vascular Cognitive Impairment," *Stroke* 35:2616-9 (2004), each of which is hereby incorporated by reference in its entirety) and impaired vascular function (Sweeney et al., "Vascular Dysfunction—The Disregarded Partner of Alzheimer's Disease." *Alzheimers Dement.* 15:158-67 (2019), which is hereby incorporated by reference in its entirety). In addition, increased levels of prothrombin (Zipser et al., "Microvascular Injury and Blood—brain Barrier Leakage in Alzheimer's Disease," *Neurobiol. Aging* 28:977-86 (2007), which is hereby incorporated by reference in its entirety), thrombin (Grammas et al., "Thrombin and Inflammatory Proteins are Elevated in Alzheimer's Disease Microvessels: Implications for Disease Pathogenesis," *J. Alzheimers Dis.* 9:51-8 (2006), which is hereby incorporated by reference in its entirety), and platelet activation (Sevush et al., "Platelet Activation in Alzheimer Disease," *Arch. Neurol.* 55:530-6 (1998); Ciabattoni et al., "Determinants of Platelet Activation in Alzheimer's Disease," *Neurobiol. Aging* 28:336-42 (2007), each of which is hereby incorporated by reference in its entirety) were detected in AD patients. Furthermore, cerebral emboli have been detected in patients with AD and are associated with cognitive decline (Purandare et al., "Cerebral Emboli in the Genesis of Dementia," *J. Neurol. Sci.* 283:17-20 (2009), which is hereby incorporated by reference in its entirety). In the preceding Examples, it was found that blood coagulation was significantly activated in the blood of HFD-treated 3×Tg mice associated with molecules, such as Vwf, Fbln1, and prothrombin. HFD-treated 3×Tg mice also exhibited increased platelet production (thrombocytosis) and MPV that could be partially attributed to elevated IL-6 and TPO, which induce MK differentiation into platelets. Large sized platelets have been shown to be more active than small platelets and can produce more thromboxane A2 resulting in sustained platelet activation and aggregation (Thompson et al., "Size Dependent Platelet Subpopulations: Relationship of Platelet Volume to Ultrastructure, Enzymatic Activity, and Function," *Br. J. Haematol.* 50:509-19 (1982), which is hereby incorporated by reference in its entirety). Hence, large platelets are associated with a poor outcome in acute myocardial infarction and ischemic stroke (Martin et al., "Influence of Platelet Size on Outcome After Myocardial Infarction," *Lancet* 338:1409-11 (1991); Smyth et al., "Influence of Platelet Size Before Coronary Angioplasty on Subsequent Restenosis," *Eur. J. Clin. Invest.* 23:361-7 (1993), each of which is hereby incorporated by reference in its entirety). Collectively, the data indicate that the blood of HFD-treated 3×Tg mice is in a prothrombotic state, which increases the risk of cerebral circulatory deficits resulting in memory deficits, as observed in the preceding Examples.

Integrin $\alpha_{IIb}\beta_3$ (GPIIb/IIIa) is a heterodimeric receptor of the integrin family expressed at high density (50 000-80 000 copies/cell) on the platelet membrane (Shattil and Ginsberg, "Perspectives Series: Cell Adhesion in Vascular Biology. Integrin Signaling in Vascular Biology," *J. Clin. Invest.* 100:1-5 (1997), which is hereby incorporated by reference in its entirety). In resting platelets, $a_{IIb}\beta_3$ exists in a low-affinity state and does not bind its ligands, such as fibrinogen, vWF, fibronectin and monomeric Aβ40. However, sustained platelet activation may result in the increased expression of $a_{IIb}\beta_3$ by alpha granules and exposure of the binding site(s) of $a_{IIb}\beta_3$ for a variety of ligands, including Aβ40. Previously, it was demonstrated that Aβ40 could bind to $a_{IIb}\beta_3$ through its RHDS sequence, which causes integrin outside-in signaling and downstream activation of Syk and PLCr2, ultimately promoting the release of the chaperone clusterin and ADP from alpha and dense granules of activated platelets, respectively (Donner et al., "Platelets Contribute to Amyloid-β Aggregation in Cerebral Vessels Through Integrin αIIbβ3-induced Outside-in Signaling and Clusterin Release," *Sci. Signal.* 9:ra52 (2016), which is hereby incorporated by reference in its entirety). The release of clusterin facilitates the conversion of soluble Aβ40 into fibrillar Aβ aggregates (Donner et al., "Platelets Contribute to Amyloid-β Aggregation in Cerebral Vessels Through Integrin αIIbβ3-induced Outside-in Signaling and Clusterin Release," *Sci. Signal.* 9:ra52 (2016), which is hereby incorporated by reference in its entirety). Consistent with this finding, it is reported that the expression of integrin $\alpha_{IIb}\beta_3$ and clusterin were significantly increased in platelets of HFD-treated 3×Tg mice. These platelets actively induced the conversion of soluble Aβ40 into fibrillar Aβ aggregates.

At 9 months and older, HFD-treated 3×Tg had platelet-associated fibrillar Aβ clots resulting in occlusion at sites of Aβ deposits in cerebral vessels. It is conceivable that the blocked blood vessels may further promote atherosclerosis-induced hypoperfusion, hypoxia, and other vascular dysfunction, consistent with the observed BBB leakage and increased tau pathology and loss of neurons in HFD-treated 3×Tg mice. Given the data that the contribution of atherosclerosis to AD related pathology is at least in part via facilitating the formation of platelet associated fibrillar Aβ aggregates, a drug that could directly dissolve platelet micro-clots would in theory normalize any platelet-Aβ clots formed in the brain. This would improve cerebral blood flow, and both neuronal function and survival. In the preceding Examples, a novel therapeutic strategy is described for clearance of preexisting platelet-Aβ clots with scFv Ab (A11) that specifically fragments activated platelet by targeting platelet GPIIIa49-66. In the presence of A11, platelet thrombi were disaggregated, thus preventing the transformation of soluble Aβ40 into fibrillar Aβ on the surface of platelet thrombi in vitro. 3×Tg mice with atherosclerosis being treated with A11 for a period of 3 months demonstrated reduced vascular permeability, in the absence of any bleeding risk. This approach, therefore, is expected to have therapeutic benefit for the treatment of AD possibly in synergistic combination with other strategies.

In the preceding Examples, it was found that the expressions of integrin $\alpha_{IIb}\beta_3$ and clusterin were significantly increased in platelets of HFD-treated 3×Tg mice. These murine platelets actively induced the conversion of soluble Aβ40 into fibrillar Aβ aggregates in vitro. The current data have established a foundation for a different therapeutic approach to combat cerebral amyloid angiopathy and associated conditions, including AD, by lysing platelet micro-clots. A11 reduced the formation of platelet-associated fibrillar Aβ aggregates in vitro and appeared to improve mouse locomotor ability. A11 treatment is expected to do the same in vivo.

In summary, the preceding Examples illustrate that a major contribution of atherosclerosis to AD pathology is via its effects on blood coagulation, increased number and activation of platelets, and the formation of platelet-mediated Aβ clots. The latter compromises cerebral blood flow, producing neuronal loss and enhances tau-related pathology, resulting in cognitive decline. The findings also support the understanding that clearance of preexisting platelet micro-clots is a potential therapeutic approach for AD treatment.

SEQUENCE LISTING

The Sequence Listing is being submitted electronically in XML format and is hereby incorporated by reference in its entirety. Said XML copy, created on Aug. 10, 2022, is named 147462.002312.ST26.xml and is 21,880 bytes in size. No new matter is being introduced.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. All of the features described herein (including any accompanying claims, abstract and drawings), and/or all of the steps of any method or process so disclosed, may be combined with any of the above aspects in any combination, except combinations where at least some of such features and/or steps are mutually exclusive. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. A method of inhibiting the onset of cerebral amyloid angiopathy (CAA), cerebral hemorrhage, cerebral infarction, cognitive impairment, dementia, and/or Alzheimer's disease in a subject, said method comprising:

administering, to a subject at risk of developing CAA, an antibody or antigen-binding fragment thereof that binds to GPIIIa49-66 on activated platelets, wherein the antibody or antigen-binding fragment thereof comprises a heavy chain variable region comprising a complementarity-determining region 1 (CDR-H1) comprising the amino acid sequence of SEQ ID NO: 1, a complementarity-determining region 2 (CDR-H2) comprising the amino acid sequence of SEQ ID NO: 2, and a complementarity-determining region 3 (CDR-H3) comprising the amino acid sequence of SEQ ID NO: 3, and a light chain variable region comprising a complementarity-determining region 1 (CDR-L1) comprising the amino acid sequence of SEQ ID NO: 5, a complementarity-determining region 2 (CDR-L2) comprising the amino acid sequence of SEQ ID NO: 6, and a complementarity-determining region 3 (CDR-L3) comprising the amino acid sequence of SEQ ID NO: 7, wherein said administering is effective to inhibit formation of platelet micro-clots, thereby inhibiting the onset of CAA, cerebral hemorrhage, cerebral infarction, cognitive impairment, dementia, and/or Alzheimer's disease.

2. The method of claim 1, wherein GPIIIa49-66 comprises the amino acid sequence of SEQ ID NO: 11 (CAPESIEFPVSEAREVLED).

3. The method of claim 1, wherein the antibody or antigen-binding fragment thereof comprises a heavy chain variable region (VH) comprising an amino acid sequence having at least 80% sequence identity to the amino acid sequence of SEQ ID NO: 4, and a light chain variable region (VL) comprising an amino acid sequence having at least 80% sequence identity to the amino acid sequence of SEQ ID NO: 8.

4. The method of claim 1, wherein the antigen-binding fragment is selected from a Fab, $F(ab)_2$, or Fv fragment of an antibody.

5. The method of claim 1, wherein the antibody is a single chain antibody.

6. The method of claim 5, wherein the single chain antibody comprises a VH comprising the amino acid sequence of SEQ ID NO: 4 and a VL comprising the amino acid sequence of SEQ ID NO: 8.

7. A method of inhibiting the onset of cerebral amyloid angiopathy (CAA), cerebral hemorrhage, cerebral infarction, cognitive impairment, dementia, and/or Alzheimer's disease in a subject, said method comprising: administering, to a subject at risk of developing CAA, a nucleic acid molecule encoding an antibody or antigen-binding fragment thereof that binds to GPIIIa49-66 on activated platelets, wherein the antibody or antigen-binding fragment thereof comprises a heavy chain variable region comprising a complementarity-determining region 1 (CDR-H1) comprising the amino acid sequence of SEQ ID NO: 1, a complementarity-determining region 2 (CDR-H2) comprising the amino acid sequence of SEQ ID NO: 2, and a complementarity-determining region 3 (CDR-H3) comprising the amino acid sequence of SEQ ID NO: 3, and a light chain variable region comprising a complementarity-determining region 1 (CDR-L1) comprising the amino acid sequence of SEQ ID NO: 5, a complementarity-determining region 2 (CDR-L2) comprising the amino acid sequence of SEQ ID NO: 6, and a complementarity-determining region 3 (CDR-L3) comprising the amino acid sequence of SEQ ID NO: 7, wherein said administering is effective to inhibit formation of platelet micro-clots, thereby inhibiting the onset of CAA, cerebral hemorrhage, cerebral infarction, cognitive impairment, dementia, and/or Alzheimer's disease.

8. The method of claim 7, wherein the nucleic acid molecule is an mRNA molecule.

9. The method of claim 1, wherein the subject has hereditary CAA.

10. The method of claim 9, wherein the hereditary CAA is caused by one or more mutations in a gene selected from APP, CST3, PRNP, GSN, TTR, or ITM2B.

11. The method of claim 1, wherein the subject has atherosclerosis.

12. A method of reducing cerebral vascular platelet micro-clots in a subject in need thereof, said method comprising:

administering, to the subject having cerebral vascular platelet micro-clots, an antibody or antigen-binding fragment thereof that binds to GPIIIa49-66 on activated platelets, wherein the antibody or antigen-binding fragment thereof comprises a heavy chain variable region comprising a complementarity-determining region 1 (CDR-H1) comprising the amino acid sequence of SEQ ID NO: 1, a complementarity-determining region 2 (CDR-H2) comprising the amino acid sequence of SEQ ID NO: 2, and a complementarity-determining region 3 (CDR-H3) comprising the amino acid sequence of SEQ ID NO: 3, and a light chain variable region comprising a complementarity-determining region 1 (CDR-L1) comprising the amino acid sequence of SEQ ID NO: 5, a complementarity-determining region 2 (CDR-L2) comprising the amino acid sequence of SEQ ID NO: 6, and a complementarity-determining region 3 (CDR-L3) comprising the amino acid sequence of SEQ ID NO: 7, wherein said administering is effective to dissolve and clear the cerebral vascular platelet micro-clots.

13. The method of claim 12, wherein the subject has cerebral amyloid angiopathy (CAA).

* * * * *